(12) United States Patent
Salmon et al.

(10) Patent No.: US 7,956,188 B2
(45) Date of Patent: Jun. 7, 2011

(54) ACETAMIDE COMPOUNDS AS FUNGICIDES

(75) Inventors: Roger Salmon, Bracknell (GB); David Philip Bacon, Bracknell (GB); Ewan James Turner Chrystal, Bracknell (GB); David William Langton, Bracknell (GB); Andrew Jonathan Knee, Bracknell (GB); Gordon Richard Munns, Bracknell (GB); Laura Quaranta, Basel (CH); Hans-Georg Brunner, Basel (CH); Renaud Beaudegnies, Basel (CH); Fredrik Cederbaum, Basel (CH); Fiona Murphy Kessabi, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 999 days.

(21) Appl. No.: 11/720,452

(22) PCT Filed: Nov. 29, 2005

(86) PCT No.: PCT/EP2005/012735

§ 371 (c)(1), (2), (4) Date: May 30, 2007

(87) PCT Pub. No.: WO2006/058700

PCT Pub. Date: Jun. 8, 2006

(65) Prior Publication Data

US 2008/0171767 A1    Jul. 17, 2008

(30) Foreign Application Priority Data

Dec. 1, 2004 (GB) .................................. 0426373.7

(51) Int. Cl.
*C07D 215/38* (2006.01)

(52) U.S. Cl. ........................................ 546/159; 546/163
(58) Field of Classification Search .................. 546/159, 546/163
See application file for complete search history.

(56) References Cited

U.S. PATENT DOCUMENTS

| 7,371,764 | B2 * | 5/2008 | Crowley et al. | 514/311 |
| 2007/0042996 | A1 * | 2/2007 | Crowley et al. | 514/63 |
| 2008/0096917 | A1 * | 4/2008 | Crowley et al. | 514/311 |

FOREIGN PATENT DOCUMENTS

| WO | 2004047538 | * | 6/2004 |
| WO | 2004048337 | | 6/2004 |
| WO | 2004052100 | | 6/2004 |
| WO | 2004108663 | | 12/2004 |

OTHER PUBLICATIONS

CA 135:380399, abstract only of WO 2001054481, 2001.*
Patent Abstracts of Japan, vol. 018, No. 532 (p. 1810), Oct. 7, 1994 & JP 06 186702 A (Konica Corp), Jul. 8, 1994 cited in the application abstract, compounds C-18.

* cited by examiner

*Primary Examiner* — D. Margaret Seaman
(74) *Attorney, Agent, or Firm* — James Cueva

(57) ABSTRACT

Compounds of the general formula (I); wherein the substituents are as defined in claim 1, are useful as fungicides.

(I)

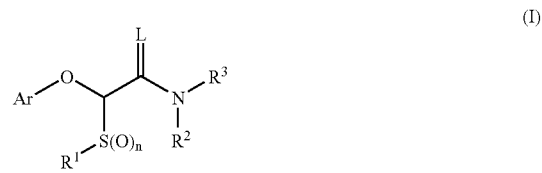

15 Claims, No Drawings

ACETAMIDE COMPOUNDS AS FUNGICIDES

This invention relates to novel N-substituted-2-alkylthio-2-(substituted aryloxy and heteroaryloxy)alkylamides and to their sulphinyl and sulphonyl derivatives. It also relates to processes for preparing them, to compositions containing them and to methods of using them to combat fungi, especially fungal infections of plants.

Certain pyridyloxy(thio)alkanoic and heteroaryloxy(thio)alkanoic acid amide derivatives and their use as agricultural and horticultural bactericides are disclosed in WO 99/33810 and JP 2001-89453. Certain substituted phenoxybutyramides and their use as mildewicides are described in EP 0,001,721. Certain phenoxy and pyridyloxy alkanoic acid amides and their use as fungicides are described in WO 04/047537, WO 04/048316, WO 04/048315 and WO 03/048128. Certain phenoxy and heteroaryloxy alkoxy acetamide derivatives and their use as fungicides are disclosed in WO 04/052100, WO 04/048337 and WO 04/047538. The use of certain substituted 2-alkylsulphonyl-2-phenoxyalkylanilides as photographic materials is disclosed in JP 61,86702 and in U.S. Pat. No. 4,286,053.

The present invention is concerned with the provision of particular N-substituted-2-alkylthio-2-(substituted aryloxy and heteroaryloxy)alkylamides and their sulphinyl and sulphonyl derivatives for use mainly as plant fungicides.

Thus according to the present invention there is provided a compound of the general formula (1):

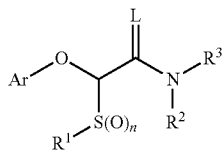

(1)

wherein

Ar is aryl (e.g. phenyl, naphthyl), heteroaryl (5-membered heteroaryl e.g. pyrrolyl, furyl, thienyl, pyrazolyl, imidazolyl, oxazolyl, isoxazolyl, thiazolyl, isothiazolyl, triazolyl, oxadiazolyl, thiadiazolyl, tetrazolyl; 6-membered heteroaryl e.g. pyridyl, pyridazinyl, pyrimidinyl, pyrazinyl, triazinyl; 5-membered heteroaryl fused to benzene e.g. indolyl, benzofuranyl, benzothienyl, benzimidazolyl, benzoxazolyl, benzisoxazolyl, benzothiazolyl, benzisothiazolyl, indazolyl, benzoxadiazolyl, benzothiadiazolyl, benzotriazolyl; 5-membered heteroaryl fused to two benzene rings e.g. dibenzofuranyl, dibenzothienyl; 5-membered heteroaryl fused to one benzene ring and one pyridine ring e.g. benzofuropyridyl, benzothienopyridyl; 6-membered heteroaryl fused to benzene e.g. quinolyl, isoquinolyl, quinazolinyl, quinoxalinyl), or a partially or fully saturated cyclyl optionally containing one or two heteroatoms independently selected from N, O or S (e.g. 9H-fluorenyl, 1,2,3,4-tetrahydronaphthyl, indanyl, 1,3-benzodioxolyl, 1,3-benzoxathiolyl, 1,3-benzodithiolyl), the aryl, heteroaryl or partially or fully saturated cyclyl being optionally substituted with one, two, three, four or five substitutents independently selected from halo (e.g. fluoro, chloro, bromo, iodo), cyano, nitro, azido, $C_{1-6}$ alkyl (e.g. methyl), halo$(C_{1-6})$alkyl (e.g. trifluoromethyl), $C_{3-6}$ cycloalkyl, $C_{3-6}$ cycloalkyl$(C_{1-4})$alkyl, $C_{2-6}$ alkenyl (e.g. allyl), halo$(C_{2-6})$alkenyl, $C_{2-6}$ alkynyl (e.g. propargyl), halo$(C_{2-6})$alkynyl, $C_{1-6}$ alkoxy (e.g. methoxy), halo$(C_{1-6})$alkoxy (e.g. trifluoromethoxy), $C_{2-6}$ alkenyloxy (e.g. allyloxy), halo-$(C_{2-6})$alkenyloxy, $C_{2-6}$ alkynyloxy (e.g. propargyloxy), halo$(C_{2-6})$alkynyloxy, aryl (e.g. phenyl), aryloxy (e.g. phenoxy), aryl$(C_{1-6})$alkyl (e.g. benzyl), aryl$(C_{1-6})$alkoxy (e.g. benzyloxy), heteroaryl (e.g. pyridyl), heteroaryloxy (e.g. pyridyloxy), heteroaryl-$(C_{1-6})$alkyl (e.g. pyridylmethyl), heteroaryl$(C_{1-6})$alkoxy (e.g. pyridylmethoxy), —SF$_5$, —S(O)$_u$$(C_{1-6})$alkyl wherein u is 0, 1 or 2 and the alkyl group is optionally substituted with halo (particularly fluoro, e.g. trifluoromethylsulphonyl), —OSO$_2$$(C_{1-4})$alkyl where the alkyl group is optionally substituted with halo (particularly fluoro, e.g. trifluoromethyl-sulphonyloxy), —CONR$^u$R$^v$, —COR$^u$, —CO$_2$R$^u$, —CR$^u$=NR$^v$, —NR$^u$R$^v$, —NR$^u$COR$^v$, —NR$^u$CO$_2$R$^v$, —SO$_2$NR$^u$R$^v$ or —NR$^u$SO$_2$R$^w$ where R$^w$ is $C_{1-6}$ alkyl optionally substituted with halogen and R$^u$ and R$^v$ are independently H or $C_{1-6}$ alkyl optionally substituted with halogen (e.g. —NH-COCF$_3$ or —N(CH$_3$)$_2$), or, in the case of —CONR$^u$R$^v$ or —SO$_2$NR$^u$R$^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted;

$R^1$ is $C_{1-4}$ alkyl (e.g. methyl, ethyl), halo$(C_{1-4})$alkyl (e.g. CF$_3$, CF$_2$H, CF$_2$Cl, CH$_2$CH$_2$F) or $C_{3-4}$ cycloalkyl;

$R^2$ is H, $C_{1-8}$ alkyl (e.g. methyl, ethyl, iso-propyl), $C_{3-4}$ cycloalkyl (e.g. cyclopropyl), $C_{2-8}$ alkenyl (e.g. allyl, 3-methyl-but-2-enyl, 4-methyl-pent-2-enyl), cyano$(C_{1-4})$ alkyl (e.g. cyanomethyl, cyanoethyl), $C_{1-4}$ alkoxy$(C_{1-4})$ alkyl (e.g. methoxymethyl, ethoxyethyl), $C_{1-4}$ alkoxy $(C_{1-4})$alkoxy$(C_{1-4})$alkyl (e.g methoxyethoxymethyl) or benzyloxy$(C_{1-4})$alkyl (e.g. benzyloxymethyl) in which the phenyl ring of the benzyl moiety is optionally substituted with $C_{1-4}$ alkoxy;

$R^3$ is —(CR$^a$R$^b$)$_p$(CR$^c$R$^d$)$_q$(X)$_r$(CR$^e$R$^f$)$_s$R$^4$, wherein R$^a$, R$^b$, R$^c$, R$^d$, R$^e$ and R$^f$ are independently H, $C_{1-4}$ alkyl (e.g. methyl), halo (e.g. chloro), cyano, hydroxy, $C_{1-4}$ alkoxy (e.g. methoxy) or $C_{1-4}$ alkoxycarbonyl (e.g. ethoxycarbonyl), or R$^a$R$^b$, R$^c$R$^d$ or R$^e$R$^f$ may join to form a 3-8 membered ring optionally containing an oxygen, sulfur or nitrogen atom, X is (CO), (CO)O, O(CO), O, S(O)$_t$ wherein t is 0, 1 or 2, NH or N($C_{1-6}$)alkyl, p, r and s are 0 or 1, q is 0, 1 or 2, $R^4$ is $C_{1-6}$ alkyl (e.g. methyl, ethyl, iso-propyl, n-butyl, tert-butyl) optionally substituted with one, two or three substituents independently selected from halo (e.g. fluoro, chloro), cyano or hydroxy, $C_{1-4}$ alkoxy$(C_{1-4})$alkyl (e.g. methoxymethyl, ethoxyethyl), $C_{1-4}$ alkoxy-$(C_{1-4})$alkoxy $(C_{1-4})$alkyl (e.g methoxyethoxymethyl), benzyloxy$(C_{1-4})$ alkyl (e.g. benzyloxymethyl), $C_{2-6}$ alkenyloxy (e.g. allyloxy), —S(O)$_x$$(C_{1-6})$alkyl wherein x is 0, 1 or 2 and the alkyl group is optionally substituted with halo (particularly fluoro, e.g. 2,2,2-trifluoroethylthio), mono- or di-$(C_{1-6})$ alkylamino (e.g. N-methylamino, N,N-dimethylamino) or tri$(C_{1-4})$alkylsilyl (e.g. trimethylsilyl), or $R^4$ is $C_{2-6}$ alkenyl (e.g. ethenyl, allyl) optionally substituted with one, two or three substituents independently selected from halo (e.g. chloro), cyano, hydroxy, $C_{1-6}$ alkoxy (e.g. methoxy), $C_{1-6}$ alkylcarbonyl (e.g. acetyl), $C_{1-6}$ alkoxycarbonyl (e.g. methoxycarbonyl), phenyl optionally substituted with $C_{1-4}$ alkoxy, or $R^4$ is —CH$_2$—C≡C—R$^5$, wherein $R^5$ is H, $C_{1-8}$ alkyl, $C_{3-6}$ cycloalkyl or $C_{3-6}$ cycloalkyl$(C_{1-4})$ alkyl in which the alkyl or cycloalkyl group is optionally substituted with halo, hydroxy, $C_{1-6}$ alkoxy, $C_{1-3}$ alkoxy- ($C_{1-3}$)alkoxy, cyano, $C_{1-4}$ alkylcarbonyloxy, aminocarbonyloxy or mono- or di($C_{1-4}$)alkyl-aminocarbonyloxy, tri ($C_{1-4}$)alkylsilyloxy, —S(O)$_g$($C_{1-6}$)alkyl where g is 0, 1 or 2, or $R^5$ is optionally substituted aryl (e.g. phenyl), optionally substituted aryl($C_{1-4}$)alkyl (e.g. benzyl), optionally substituted aryloxy($C_{1-4}$)alkyl (e.g. phenoxymethyl), optionally substituted aryl($C_{1-4}$)alkoxy($C_{1-4}$)alkyl (e.g. benzyloxymethyl), optionally substituted heteroaryl (e.g. pyridyl, thienyl, pyrazolyl, imidazolyl, triazolyl) or optionally substituted heteroaryl($C_{1-4}$)alkyl (e.g. pyridylmethyl, phthalimidoethyl), optionally substituted heteroaryloxy ($C_{1-4}$)alkyl (e.g. thienyloxymethyl) or optionally substituted heteroaryl-($C_{1-4}$)alkoxy($C_{1-4}$)alkyl (e.g. thienylmethoxymethyl), in which the optionally substituted aryl and heteroaryl rings or moieties of the $R_5$ values are optionally substituted with one, two or three substituents independently selected from halo (e.g. fluoro, chloro, bromo, iodo), cyano, nitro, azido, $C_{1-6}$ alkyl (e.g. methyl), halo ($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$) alkenyl, $C_{2-6}$ alkynyl (e.g. propargyl), halo($C_{2-6}$)alkynyl, $C_{1-6}$ alkoxy (e.g. methoxy), halo($C_{1-6}$)alkoxy (e.g. trifluoromethoxy), $C_{2-6}$ alkenyloxy (e.g. allyloxy), halo($C_{2-6}$) alkenyloxy, $C_{2-6}$ alkynyloxy (e.g. propargyloxy), halo ($C_{2-6}$)-alkynyloxy, aryl (e.g. phenyl), aryloxy (e.g. phenoxy), aryl($C_{1-6}$)alkyl (e.g. benzyl), aryl-($C_{1-6}$)alkoxy (e.g. benzyloxy), heteroaryl (e.g. pyridyl), heteroaryloxy (e.g. pyridyloxy), heteroaryl($C_{1-6}$)alkyl (e.g. pyridylmethyl), heteroaryl($C_{1-6}$)alkoxy (e.g. pyridylmethoxy), —SF$_5$, —S(O)$_g$($C_{1-4}$)alkyl wherein g is 0, 1 or 2 and the alkyl is optionally substituted with halo (particularly fluoro, e.g. trifluoromethylsulphonyl), —OSO$_2$($C_{1-4}$)alkyl where the alkyl group is optionally substituted with halo (particularly fluoro, e.g. trifluoromethylsulphonyloxy), —CONR$^g$R$^h$, —COR$^g$, —CO$_2$R$^g$, —CR$^g$=NR$^h$, —NR$^g$R$^h$, —NR$^g$COR$^h$, —NR$^g$CO$_2$R$^h$, —SO$_2$NR$^g$R$^h$ or —NR$^g$SO$_2$R$^i$ where R$^i$ is $C_{1-6}$ alkyl optionally substituted with halogen and R$^g$ and R$^h$ are independently H or $C_{1-6}$ alkyl optionally substituted with halogen (e.g. —NHCOCF$_3$ or —N(CH$_3$)$_2$), or, in the case of —CONR$^g$R$^h$ or —SO$_2$NR$^g$R$^h$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted, or $R^4$ is $C_{3-6}$ cycloalkyl (e.g. cyclopropyl, cyclopentyl, cyclohexyl), $C_{5-6}$ cycloalkenyl (e.g. cyclopentenyl, cyclohexenyl), aryl (e.g. phenyl, naphthyl), heteroaryl (5 membered heteroaryl e.g. pyrrolyl, furyl, thienyl, pyrazolyl, imidazoyl, oxazolyl, isoxazolyl, thiazolyl, isothiazolyl, triazolyl, oxadiazolyl, thiadiazolyl, tetrazolyl; 6-membered heteroaryl e.g. pyridyl, pyridazinyl, pyrimidyl, pyrazinyl, triazinyl), or a partially or fully saturated cyclyl optionally containing one or two heteroatoms independently selected from N, O or S (e.g. pyrrolidinyl, tetrahydrofuryl, tetrahydrothienyl, piperidyl, dioxolanyl, morpholino, thiadiazinyl, 1,2,3,4-tetrahydronaphthyl, 2,3-dihydrobenzo-furanyl), the aryl, heteroaryl or partially or fully saturated cyclyl being optionally substituted with one, two or three substituents independently selected from halo (e.g. fluoro, chloro, bromo, iodo), cyano, nitro, azido, $C_{1-6}$ alkyl (e.g. methyl, n-pentyl), halo($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo($C_{2-6}$)alkynyl, $C_{1-6}$ alkoxy (e.g. methoxy), halo ($C_{1-6}$)alkoxy (e.g. difluoromethoxy, trifluoromethoxy), $C_{2-6}$ alkenyloxy (e.g. allyloxy), halo($C_{2-6}$)alkenyloxy, $C_{2-6}$ alkynyloxy (e.g. propargyloxy), halo($C_{2-6}$)-alkynyloxy, —SF$_5$, —S(O)$_x$($C_{1-6}$)alkyl wherein x is 0, 1 or 2 and the alkyl group is optionally substituted with halo (particularly fluoro, e.g. trifluoromethylsulphonyl), —OSO$_2$($C_{1-4}$)alkyl where the alkyl group is optionally substituted with halo (particularly fluoro, e.g. trifluoromethylsulphonyloxy), —CONR$^x$R$^y$, —CON(OR$^x$)R$^y$, —COR$^x$, —CO$_2$R$^x$, —CR$^x$=NR$^y$, —NR$^x$R$^y$, —NR$^x$COR$^y$, —NR$^x$CO$_2$R$^y$, —SO$_2$NR$^x$R$^y$ or —NR$^x$SO$_2$R$^z$ where R$^z$ is $C_{1-8}$ alkyl optionally substituted with halogen and R$^x$ and R$^y$ are independently H or $C_{1-6}$ alkyl optionally substituted with halogen (e.g. —NHCOCF$_3$ or —N(CH$_3$)$_2$), or $R^2$ and $R^3$ may join to form a saturated or unsaturated 5- or 6-membered ring optionally containing an O or S atom (e.g. tetrahydropyrrolyl, thiazolidinyl, piperidino, morpholino, thiomorpholino, 2,5 dihydropyrrolyl) and optionally substituted with one, two or three halo (e.g. chloro), $C_{1-4}$ alkyl (e.g. methyl, ethyl) or mono- or di-($C_{1-4}$)alkylamino-carbonyl, or optionally containing an N atom (e.g. piperazinyl) which is optionally substituted on the N atom with $C_{1-4}$ alkyl optionally substituted with halo, $C_{1-6}$ alkoxy or cyano, or phenyl optionally substituted with nitro, $C_{1-4}$ alkyl, halo($C_{1-4}$)alkyl (e.g. trifluoromethyl), $C_{1-4}$ alkylcarbonyl (e.g. acetyl) or heteroaryl (e.g. pyridyl), or $R^2$ and $R^3$ may join to form a 6,6-membered saturated bicycle (e.g. decahydro-isoquinoline); wherein any of the foregoing alkyl, cycloalkyl, alkenyl, alkynyl, aryl or heteroaryl groups or moieties are optionally substituted;

L is O or S; and n is 0, 1 or 2.

The compounds of the invention contain at least one asymmetric carbon atom and may exist as enantiomers (or as pairs of diastereoisomers) or as mixtures of such. Further, when n is 1, the compounds of the invention are sulphoxides, which can exists in two enantiomeric forms, and the adjacent carbon can also exists in two enantiomeric forms. Compounds of general formula (1) can therefore exist as racemates, diastereoisomers, or single enantiomers, and the invention includes all possible isomers or isomer mixtures in all proportions. It is to be expected that for any given compound, one isomer may be more fungicidally active than another.

Except where otherwise stated, alkyl groups and alkyl moieties of alkoxy, alkylthio, etc., suitably contain from 1 to 6, typically from 1 to 4, carbon atoms in the form of straight or branched chains. Examples are methyl, ethyl, n- and isopropyl and n-, sec-, iso- and tert-butyl. Where alkyl moieties contain 5 or 6 carbon atoms, examples are n-pentyl and n-hexyl. Examples of suitable optional substituents of alkyl groups and moieties include halo, hydroxy, $C_{1-4}$ alkoxy and $C_{1-4}$ alkoxy($C_{1-4}$)alkoxy, optionally substituted aryl and optionally substituted heteroaryl. Where the optional substituent is halo, the haloalkyl group or moiety is typically trichloromethyl or trifluoromethyl.

Except where otherwise stated, alkenyl and alkynyl moieties also suitably contain from 2 to 6, typically from 2 to 4, carbon atoms in the form of straight or branched chains. Examples are allyl, ethynyl and propargyl. Optional substituents include halo.

Halo includes fluoro, chloro, bromo and iodo. Most commonly it is fluoro, chloro or bromo and usually fluoro or chloro Aryl is usually phenyl but also includes naphthyl, anthryl and phenanthryl.

Heteroaryl is typically a 5- or 6-membered aromatic ring containing one or more O, N or S heteroatoms, which may be fused to one or more other aromatic or hetero-aromatic rings, such as a benzene ring. Examples are thienyl, furyl, pyrrolyl, isoxazolyl, oxazolyl, thiazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuranyl, benzo-thienyl, dibenzofuranyl, dibenzothienyl, benzothiazolyl, benzoxazolyl, benzimidazolyl, indolyl, quinolyl, isoquinolyl, quinazolinyl and quinoxalinyl groups and, where appropriate, N-oxides and salts thereof. Any of the aryl or heteroaryl values are optionally substituted. Except where otherwise stated, substituents which may be present include one or more of the following: halo, hydroxy, mercapto, $C_{1-6}$ alkyl (especially methyl and ethyl), $C_{2-6}$ alkenyl (especially allyl), $C_{2-6}$ alkynyl (especially propargyl), $C_{1-6}$ alkoxy (especially methoxy), $C_{2-6}$ alkenyloxy (especially allyloxy), $C_{2-6}$ alkynyloxy (especially propargyloxy), halo $(C_{1-6})$alkyl (especially trifluoromethyl), halo$(C_{1-6})$alkoxy (especially trifluoromethoxy), —S(O)$_m$(C$_{1-6}$)alkyl wherein m is 0, 1 or 2 and the alkyl is optionally substituted with halo, hydroxy $(C_{1-6})$alkyl, $C_{1-4}$ alkoxy$(C_{1-4})$alkyl, $C_{1-4}$alkoxy$(C_{1-4})$alkoxy, $C_{3-6}$cycloalkyl, $C_{3-6}$ cycloalkyl$(C_{1-4})$alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted —S(O)$_m$aryl wherein m is 0, 1 or 2 (especially optionally substituted phenylthio), optionally substituted —S(O)$_m$heteroaryl wherein m is 0, 1 or 2 (especially optionally substituted pyridylthio or pyrimidinylthio), optionally substituted aryl $(C_{1-4})$alkyl (especially optionally substituted benzyl, optionally substituted phenethyl and optionally substituted phenyl n-propyl) in which the alkyl moiety is optionally substituted with hydroxy, optionally substituted heteroaryl$(C_{1-4})$alkyl (especially optionally substituted pyridyl- or pyrimidinyl $(C_{1-4})$alkyl), optionally substituted aryl$(C_{2-4})$alkenyl (especially optionally substituted phenylethenyl), optionally substituted heteroaryl$(C_{2-4})$alkenyl (especially optionally substituted pyridylethenyl or pyrimidinylethenyl), optionally substituted aryl$(C_{1-4})$alkoxy (especially optionally substituted benzyloxy and phenethyloxy), optionally substituted heteroaryl$(C_{1-4})$alkoxy (especially optionally substituted pyridyl$(C_{1-4})$alkoxy or pyrimidinyl$(C_{1-4})$alkoxy), optionally substituted aryloxy$(C_{1-4})$alkyl (especially phenoxymethyl), optionally substituted heteroaryloxy-$(C_{1-4})$alkyl (especially optionally substituted pyridyloxy or pyrimidinyloxy$(C_{1-4})$alkyl), optionally substituted —S(O)$_m$(C$_{1-4}$)alkylaryl wherein m is 0, 1 or 2 (especially optionally substituted benzylthio and phenethylthio), optionally substituted —S(O)$_m$(C$_{1-4}$)alkyl-heteroaryl wherein m is 0, 1 or 2 (especially optionally substituted pyridyl$(C_{1-4})$alkylthio or pyrimidinyl$(C_{1-4})$alkylthio), optionally substituted —(C$_{1-4}$)alkylS (O)$_m$aryl wherein m is 0, 1 or 2 (especially phenylthiomethyl), optionally substituted —(C$_{1-4}$)alkyl S(O)$_m$heteroaryl wherein m is 0, 1 or 2 (especially optionally substituted pyridylthio$(C_{1-4})$alkyl or pyrimidinylthio$(C_{1-4})$alkyl), acyloxy, including $C_{1-4}$ alkanoyloxy (especially acetyloxy) and benzoyloxy, cyano, isocyano, thiocyanato, isothiocyanato, nitro, NR$^g$R$^h$, —NHCOR$^g$, —NHCONR$^g$R$^h$, —CONR$^g$R$^h$, —CO$_2$R$^g$, —SO$_2$R$^i$, —OSO$_2$R$^i$, —COR$^g$, —CR$^g$=NR$^h$ or —N=CR$^g$R$^h$ in which R$^i$ is $C_{1-4}$ alkyl, halo $(C_{1-4})$alkyl, $C_{1-4}$ alkoxy, halo$(C_{1-4})$alkoxy, $C_{1-4}$ alkylthio, $C_{3-6}$cycloalkyl, $C_{3-6}$ cycloalkyl$(C_{1-4})$alkyl, phenyl or benzyl, the phenyl and benzyl groups being optionally substituted with halogen, $C_{1-4}$ alkyl or $C_{1-4}$ alkoxy and R$^g$ and R$^h$ are independently hydrogen, $C_{1-4}$ alkyl, halo$(C_{1-4})$alkyl, $C_{1-4}$ alkoxy, halo$(C_{1-4})$alkoxy, $C_{1-4}$ alkylthio, $C_{3-6}$ cycloalkyl, $C_{3-6}$ cycloalkyl$(C_{1-4})$alkyl, phenyl or benzyl, the phenyl and benzyl groups being optionally substituted with halogen, $C_{1-4}$ alkyl or $C_{1-4}$ alkoxy.

Of particular interest are compounds (1) where Ar is aryl (e.g. phenyl, naphthyl), heteroaryl (5-membered heteroaryl e.g. pyrrolyl, furyl, thienyl, pyrazolyl, imidazolyl, oxazolyl, isoxazolyl, thiazolyl, isothiazolyl, triazolyl, oxadiazolyl, thiadiazolyl, tetrazolyl; 6-membered heteroaryl e.g. pyridyl, pyridazinyl, pyrimidinyl, pyrazinyl, triazinyl; 5-membered heteroaryl fused to benzene e.g. indolyl, benzofuranyl, benzothienyl, benzimidazolyl, benzoxazolyl, benzisoxazolyl, benzothiazolyl, benzisothiazolyl, indazolyl, benzoxadiazolyl, benzothiadiazolyl, benzotriazolyl; 5-membered heteroaryl fused to two benzene rings e.g. dibenzofuranyl, dibenzothienyl; 5-membered heteroaryl fused to one benzene ring and one pyridine ring e.g. benzofuropyridyl, benzothienopyridyl; 6-membered heteroaryl fused to benzene e.g. quinolyl, isoquinolyl, quinazolinyl, quinoxalinyl), or a partially or fully saturated cyclyl optionally containing one or two heteroatoms independently selected from N, O or S (e.g. 9H-fluorenyl, 1,2,3,4-tetrahydronaphthyl, indanyl, 1,3-benzodioxolyl, 1,3-benzoxathiolyl, 1,3-benzodithiolyl), the aryl, heteroaryl or partially or fully saturated cyclyl being optionally substituted with one, two, three, four or five substitutents independently selected from halo (e.g. fluoro, chloro, bromo, iodo), cyano, nitro, azido, $C_{1-6}$ alkyl (e.g. methyl), halo $(C_{1-6})$alkyl (e.g. trifluoromethyl), $C_{3-6}$ cycloalkyl, $C_{3-6}$ cycloalkyl$(C_{1-4})$alkyl, $C_{2-6}$ alkenyl (e.g. allyl), halo$(C_{2-6})$alkenyl, $C_{2-6}$ alkynyl (e.g. propargyl), halo$(C_{2-6})$alkynyl, $C_{1-6}$ alkoxy (e.g. methoxy), halo$(C_{1-6})$alkoxy (e.g. trifluoromethoxy), $C_{2-6}$ alkenyloxy (e.g. allyloxy), halo-$(C_{2-6})$alkenyloxy, $C_{2-6}$ alkynyloxy (e.g. propargyloxy), halo$(C_{2-6})$ alkynyloxy, aryl (e.g. phenyl), aryloxy (e.g. phenoxy), aryl $(C_{1-6})$alkyl (e.g. benzyl), aryl$(C_{1-6})$alkoxy (e.g. benzyloxy), heteroaryl (e.g. pyridyl), heteroaryloxy (e.g. pyridyloxy), heteroaryl-$(C_{1-6})$alkyl (e.g. pyridylmethyl), heteroaryl$(C_{1-6})$ alkoxy (e.g. pyridylmethoxy), —SF$_5$, —S(O)$_u$(C$_{1-6}$)alkyl wherein u is 0, 1 or 2 and the alkyl group is optionally substituted with halo (particularly fluoro, e.g. trifluoromethylsulphonyl), —OSO$_2$(C$_{1-4}$)alkyl where the alkyl group is optionally substituted with halo (particularly fluoro, e.g. trifluoromethyl-sulphonyloxy), —CONR$^u$R$^v$, —COR$^u$, —CO$_2$R$^u$, —CR$^u$=NR$^v$, —NR$^u$R$^v$, —NR$^u$COR$^v$, —NR$^u$CO$_2$R$^v$, —SO$_2$NR$^u$R$^v$ or —NR$^u$SO$_2$R$^w$ where R$^w$ is $C_{1-6}$ alkyl optionally substituted with halogen and R$^u$ and R$^v$ are independently H or $C_{1-6}$ alkyl optionally substituted with halogen (e.g. —NHCOCF$_3$ or —N(CH$_3$)$_2$), or, in the case of —CONR$^u$R$^v$ or —SO$_2$NR$^u$R$^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted;

R$^1$ is $C_{1-4}$ alkyl (e.g. methyl, ethyl), halo$(C_{1-4})$alkyl (e.g. CF$_3$, CF$_2$H, CF$_2$Cl, CH$_2$CH$_2$F) or $C_{3-4}$ cycloalkyl;

R$^2$ is H, $C_{1-8}$ alkyl (e.g. methyl, ethyl, iso-propyl), $C_{3-4}$ cycloalkyl (e.g. cyclopropyl), $C_{2-8}$ alkenyl (e.g. allyl, 3-methyl-but-2-enyl, 4-methyl-pent-2-enyl), cyano$(C_{1-4})$ alkyl (e.g. cyanomethyl, cyanoethyl), $C_{1-4}$ alkoxy $(C_{1-4})$alkyl (e.g. methoxymethyl, ethoxyethyl), $C_{1-4}$ alkoxy$(C_{1-4})$alkoxy$(C_{1-4})$alkyl (e.g methoxyethoxymethyl) or benzyloxy$(C_{1-4})$alkyl (e.g. benzyloxymethyl) in which the phenyl ring of the benzyl moiety is optionally substituted with $C_{1-4}$ alkoxy;

$R^3$ is $(CR^aR^b)_p(CR^cR^d)_q(X)_r(CR^eR^f)_sR^4$, wherein $R^a$, $R^b$, $R^c$, $R^d$, $R^e$ and $R^f$ are independently H, $C_{1-4}$ alkyl (e.g. methyl), halo (e.g. chloro), cyano, hydroxy, $C_{1-4}$ alkoxy (e.g. methoxy) or $C_{1-4}$ alkoxycarbonyl (e.g. ethoxycarbonyl), or $R^aR^b$, $R^cR^d$ or $R^eR^f$ may join to form a 3-8 membered ring optionally containing an oxygen, sulfur or nitrogen atom, X is (CO), (CO)O, O(CO), O, $S(O)_t$ wherein t is 0, 1 or 2, NH or $N(C_{1-6})$alkyl, p, r and s are 0 or 1, q is 0, 1 or 2, $R^4$ is $C_{1-6}$ alkyl (e.g. methyl, ethyl, iso-propyl, n-butyl, tert-butyl) optionally substituted with one, two or three substituents independently selected from halo (e.g. fluoro, chloro), cyano or hydroxy, $C_{1-4}$ alkoxy($C_{1-4}$)alkyl (e.g. methoxymethyl, ethoxyethyl), $C_{1-4}$ alkoxy-($C_{1-4}$)alkoxy ($C_{1-4}$)alkyl (e.g methoxyethoxymethyl), benzyloxy($C_{1-4}$) alkyl (e.g. benzyloxymethyl), $C_{2-6}$ alkenyloxy (e.g. allyloxy), —$S(O)_x(C_{1-6})$alkyl wherein x is 0, 1 or 2 and the alkyl group is optionally substituted with halo (particularly fluoro, e.g. 2,2,2-trifluoroethylthio), mono- or di-($C_{1-6}$) alkylamino (e.g. N-methylamino, N,N-dimethylamino) or tri($C_{1-4}$)alkylsilyl (e.g. trimethylsilyl), or $R^4$ is $C_{2-6}$ alkenyl (e.g. ethenyl, allyl) optionally substituted with one, two or three substituents independently selected from halo (e.g. chloro), cyano, hydroxy, $C_{1-6}$ alkoxy (e.g. methoxy), $C_{1-6}$ alkylcarbonyl (e.g. acetyl), $C_{1-6}$ alkoxycarbonyl (e.g. methoxycarbonyl), phenyl optionally substituted with $C_{1-4}$ alkoxy, or $R^4$ is $C_{3-6}$ cycloalkyl (e.g. cyclopropyl, cyclopentyl, cyclohexyl), $C_{5-6}$ cycloalkenyl (e.g. cyclopentenyl, cyclohexenyl), aryl (e.g. phenyl, naphthyl), heteroaryl (5 membered heteroaryl e.g. pyrrolyl, furyl, thienyl, pyrazolyl, imidazoyl, oxazolyl, isoxazolyl, thiazolyl, isothiazolyl, triazolyl, oxadiazolyl, thiadiazolyl, tetrazolyl; 6-membered heteroaryl e.g. pyridyl, pyridazinyl, pyrimidyl, pyrazinyl, triazinyl), or a partially or fully saturated cyclyl optionally containing one or two heteroatoms independently selected from N, O or S (e.g. pyrrolidinyl, tetrahydrofuryl, tetrahydrothienyl, piperidyl, dioxolanyl, morpholino, thiadiazinyl, 1,2,3,4-tetrahydronaphthyl, 2,3-dihydrobenzo-furanyl), the aryl, heteroaryl or partially or fully saturated cyclyl being optionally substituted with one, two or three substituents independently selected from halo (e.g. fluoro, chloro, bromo, iodo), cyano, nitro, azido, $C_{1-6}$ alkyl (e.g. methyl, n-pentyl), halo($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo($C_{2-6}$)alkynyl, $C_{1-6}$ alkoxy (e.g. methoxy), halo ($C_{1-6}$)alkoxy (e.g. difluoromethoxy, trifluoromethoxy), $C_{2-6}$ alkenyloxy (e.g. allyloxy), halo($C_{2-6}$)alkenyloxy, $C_{2-6}$ alkynyloxy (e.g. propargyloxy), halo($C_{2-6}$)-alkynyloxy, —$SF_5$, —$S(O)_x(C_{1-6})$alkyl wherein x is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethylsulphonyloxy), —$CONR^xR^y$, —$CON(OR^x)R^y$, —$COR^x$, —$CO_2R^x$, —$CR^x$=$NR^y$, —$NR^xR^y$, —$NR^xCOR^y$, —$NR^xCO_2R^y$, —$SO_2NR^xR^y$ or —$NR^xSO_2R^z$ where $R^z$ is $C_{1-8}$ alkyl optionally substituted with halogen and $R^x$ and $R^y$ are independently H or $C_{1-6}$ alkyl optionally substituted with halogen (e.g. —$NHCOCF_3$ or —$N(CH_3)_2$), or $R^2$ and $R^3$ may join to form a saturated or unsaturated 5- or 6-membered ring optionally containing an O or S atom (e.g. tetrahydropyrrolyl, thiazolidinyl, piperidino, morpholino, thiomorpholino, 2,5 dihydropyrrolyl) and optionally substituted with one, two or three halo (e.g. chloro), $C_{1-4}$ alkyl (e.g. methyl, ethyl) or mono- or di-($C_{1-4}$)alkylamino-carbonyl, or optionally containing an N atom (e.g. piperazinyl) which is optionally substituted on the N atom with $C_{1-4}$ alkyl optionally substituted with halo, $C_{1-6}$ alkoxy or cyano, or phenyl optionally substituted with nitro, $C_{1-4}$ alkyl, halo($C_{1-4}$)alkyl (e.g. trifluoromethyl), $C_{1-4}$ alkylcarbonyl (e.g. acetyl) or heteroaryl (e.g. pyridyl), or $R^2$ and $R^3$ may join to form a 6,6-membered saturated bicycle (e.g. decahydro-isoquinoline); wherein any of the foregoing alkyl, cycloalkyl, alkenyl, alkynyl, aryl or heteroaryl groups or moieties are optionally substituted;

L is O or S; and n is 0, 1 or 2.

Of particular interest are compounds (1) where Ar is phenyl optionally substituted with one, two, three, four or five substitutents independently selected from halo (e.g. fluoro, chloro, bromo, iodo), cyano, nitro, azido, $C_{1-6}$ alkyl (e.g. methyl), halo($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo ($C_{2-6}$)alkynyl, $C_{1-6}$ alkoxy (e.g. methoxy), halo($C_{1-6}$)alkoxy (e.g. trifluoromethoxy), $C_{2-6}$ alkenyloxy (e.g. allyloxy), halo-($C_{2-6}$)alkenyloxy, $C_{2-6}$ alkynyloxy (e.g. propargyloxy), halo ($C_{2-6}$)alkynyloxy, aryl (e.g. phenyl), aryloxy (e.g. phenoxy), aryl($C_{1-6}$)alkyl (e.g. benzyl), aryl($C_{1-6}$)alkoxy (e.g. benzyloxy), heteroaryl (e.g. pyridyl), heteroaryloxy (e.g. pyridyloxy), heteroaryl-($C_{1-6}$)alkyl (e.g. pyridylmethyl), heteroaryl ($C_{1-6}$)alkoxy (e.g. pyridylmethoxy), —$SF_5$, —$S(O)_u(C_{1-6})$ alkyl wherein u is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethylsulphonyloxy), —$CONR^uR^v$, —$COR^u$, —$CO_2R^u$, —$CR^u$=$NR^v$, —$NR^uR^v$, —$NR^uCOR^v$, —$NR^uCO_2R^v$, —$SO_2NR^uR^v$ or —$NR^uSO_2R^w$ where $R^w$ is $C_{1-6}$ alkyl optionally substituted with halogen and $R^u$ and $R^v$ are independently H or $C_{1-6}$ alkyl optionally substituted with halogen (e.g. —$NHCOCF_3$ or —$N(CH_3)_2$), or, in the case of —$CONR^uR^v$ or —$SO_2NR^uR^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted.

Of more particular interest are compounds (1) where Ar is phenyl optionally substituted with one, two or three substituents independently selected from halo, in particular chloro or bromo, cyano, and $C_{1-6}$ alkyl, in particular methyl. Of especial interest are compounds where Ar is 3,5-dichlorophenyl, 3,4,5-trimethylphenyl, 4-bromo-3,5-dimethylphenyl or 4-cyano-3,5-dimethylphenyl.

Of further interest are compounds (1) where Ar is pyridyl optionally substituted with one, two, three, four or five substitutents independently selected from halo (e.g. fluoro, chloro, bromo, iodo), cyano, nitro, azido, $C_{1-6}$ alkyl (e.g. methyl), halo($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo ($C_{2-6}$)alkynyl, $C_{1-6}$ alkoxy (e.g. methoxy), halo($C_{1-6}$)alkoxy (e.g. trifluoromethoxy), $C_{2-6}$ alkenyloxy (e.g. allyloxy), halo-($C_{2-6}$)alkenyloxy, $C_{2-6}$ alkynyloxy (e.g. propargyloxy), halo ($C_{2-6}$)alkynyloxy, aryl (e.g. phenyl), aryloxy (e.g. phenoxy), aryl($C_{1-6}$)alkyl (e.g. benzyl), aryl($C_{1-6}$)alkoxy (e.g. benzyloxy), heteroaryl (e.g. pyridyl), heteroaryloxy (e.g. pyridyloxy), heteroaryl-($C_{1-6}$)alkyl (e.g. pyridylmethyl), heteroaryl ($C_{1-6}$)alkoxy (e.g. pyridylmethoxy), —$SF_5$, —$S(O)_u(C_{1-6})$alkyl wherein u is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethylsulphonyloxy), —$CONR^uR^v$, —$COR^u$, —$CO_2R^u$, —$CR^u$=$NR^v$, —$NR^uR^v$, —$NR^uCOR^v$, —$NR^uCO_2R^v$, —$SO_2NR^uR^v$ or —$NR^uSO_2R^w$ where $R^w$ is $C_{1-6}$ alkyl optionally substituted with halogen and $R^u$ and $R^v$ are independently H or $C_{1-6}$ alkyl optionally substituted with halogen (e.g. —$NHCOCF_3$ or —$N(CH_3)_2$), or, in the case of —$CONR^uR^v$ or —$SO_2NR^uR^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted.

Of yet further interest are compounds (1) where Ar is pyridyl optionally substituted with halo, in particular chloro. Of special interest are compounds in which the pyridyl is attached via the 3-position, such as 5-chloropyrid-3-yl.

Of further interest are compounds (1) where Ar is benzothiazolyl optionally substituted with one, two, three, four or five substituents independently selected from halo (e.g. fluoro, chloro, bromo, iodo), cyano, nitro, azido, $C_{1-6}$ alkyl (e.g. methyl), halo-($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo($C_{2-6}$)alkynyl, $C_{1-6}$ alkoxy (e.g. methoxy), halo($C_{1-6}$)alkoxy (e.g. trifluoromethoxy), $C_{2-6}$ alkenyloxy (e.g. allyloxy), halo($C_{2-6}$)alkenyloxy, $C_{2-6}$ alkynyloxy (e.g. propargyloxy), halo($C_{2-6}$)alkynyloxy, aryl (e.g. phenyl), aryloxy (e.g. phenoxy), aryl($C_{1-6}$)alkyl (e.g. benzyl), aryl($C_{1-6}$)alkoxy (e.g. benzyloxy), heteroaryl (e.g. pyridyl), heteroaryloxy (e.g. pyridyloxy), heteroaryl-($C_{1-6}$)alkyl (e.g. pyridylmethyl), heteroaryl ($C_{1-6}$)alkoxy (e.g. pyridylmethoxy), —$SF_5$, —$S(O)_u(C_{1-6})$alkyl wherein u is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethylsulphonyloxy), —$CONR^uR^v$, —$COR^u$, —$CO_2R^u$, —$CR^u$=$NR^v$, —$NR^uR^v$, —$NR^uCOR^v$, —$NR^uCO_2R^v$, —$SO_2NR^uR^v$ or —$NR^uSO_2R^w$ where $R^w$ is $C_{1-6}$ alkyl optionally substituted with halogen and $R^u$ and $R^v$ are independently H or $C_{1-6}$ alkyl optionally substituted with halogen (e.g. —$NHCOCF_3$ or —$N(CH_3)_2$), or, in the case of —$CONR^uR^v$ or —$SO_2NR^uR^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted.

Of yet further interest are compounds (1) where Ar is benzothiazolyl optionally substituted with halo, in particular chloro. Of special interest are compounds in which the benzothiazolyl is attached via the 6-position, such as benzothiazol-6-yl.

Of particular interest are compounds (1) where Ar is dibenzofuranyl optionally substituted with one, two, three, four or five substituents independently selected from halo (e.g. fluoro, chloro, bromo, iodo), cyano, nitro, azido, $C_{1-6}$ alkyl (e.g. methyl), halo-($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo($C_{2-6}$)alkynyl, $C_{1-6}$ alkoxy (e.g. methoxy), halo($C_{1-6}$)alkoxy (e.g. trifluoromethoxy), $C_{2-6}$ alkenyloxy (e.g. allyloxy), halo($C_{2-6}$)alkenyloxy, $C_{2-6}$ alkynyloxy (e.g. propargyloxy), halo($C_{2-6}$)alkynyloxy, aryl (e.g. phenyl), aryloxy (e.g. phenoxy), aryl($C_{1-6}$)alkyl (e.g. benzyl), aryl($C_{1-6}$)alkoxy (e.g. benzyloxy), heteroaryl (e.g. pyridyl), heteroaryloxy (e.g. pyridyloxy), heteroaryl-($C_{1-6}$)alkyl (e.g. pyridylmethyl), heteroaryl ($C_{1-6}$)alkoxy (e.g. pyridylmethoxy), —$SF_5$, —$S(O)_u(C_{1-6})$alkyl wherein u is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethyl-sulphonyloxy), —$CONR^uR^v$, —$COR^u$, —$CO_2R^u$, —$CR^u$=$NR^v$, —$NR^uR^v$, —$NR^uCOR^v$, —$NR^uCO_2R^v$, —$SO_2NR^uR^v$ or —$NR^uSO_2R^w$ where $R^w$ is $C_{1-6}$ alkyl optionally substituted with halogen and $R^u$ and $R^v$ are independently H or $C_{1-6}$ alkyl optionally substituted with halogen (e.g. —$NHCOCF_3$ or —$N(CH_3)_2$), or, in the case of —$CONR^uR^v$ or —$SO_2NR^uR^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted.

Of more particular interest are compounds (1) where Ar is dibenzofuranyl optionally substituted with one, two or three substituents independently selected from halo, in particular chloro or bromo, and $C_{1-6}$ alkyl, in particular methyl. Of special interest are compounds in which the dibenzofuranyl is attached via the 2-position, such as dibenzofuran-2-yl.

Of special interest are compounds (1) where Ar is quinolinyl optionally substituted with one, two, three, four or five substituents independently selected from halo (e.g. fluoro, chloro, bromo, iodo), cyano, nitro, azido, $C_{1-6}$ alkyl (e.g. methyl), halo-($C_{1-6}$)alkyl (e.g. trifluoromethyl), $C_{3-6}$ cycloalkyl, $C_{3-6}$ cycloalkyl($C_{1-4}$)alkyl, $C_{2-6}$ alkenyl (e.g. allyl), halo($C_{2-6}$)alkenyl, $C_{2-6}$ alkynyl (e.g. propargyl), halo($C_{2-6}$)alkynyl, $C_{1-6}$ alkoxy (e.g. methoxy), halo($C_{1-6}$)alkoxy (e.g. trifluoromethoxy), $C_{2-6}$ alkenyloxy (e.g. allyloxy), halo($C_{2-6}$)alkenyloxy, $C_{2-6}$ alkynyloxy (e.g. propargyloxy), halo($C_{2-6}$)alkynyloxy, aryl (e.g. phenyl), aryloxy (e.g. phenoxy), aryl($C_{1-6}$)alkyl (e.g. benzyl), aryl($C_{1-6}$)alkoxy (e.g. benzyloxy), heteroaryl (e.g. pyridyl), heteroaryloxy (e.g. pyridyloxy), heteroaryl-($C_{1-6}$)alkyl (e.g. pyridylmethyl), heteroaryl ($C_{1-6}$)alkoxy (e.g. pyridylmethoxy), —$SF_5$, —$S(O)_u(C_{1-6})$alkyl wherein u is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethyl-sulphonyloxy), —$CONR^uR^v$, —$COR^u$, —$CO_2R^u$, —$CR^u$=$NR^v$, —$NR^uR^v$, —$NR^uCOR^v$, —$NR^uCO_2R^v$, —$SO_2NR^uR^v$ or —$NR^uSO_2R^w$ where $R^w$ is $C_{1-6}$ alkyl optionally substituted with halogen and $R^u$ and $R^v$ are independently H or $C_{1-6}$ alkyl optionally substituted with halogen (e.g. —$NHCOCF_3$ or —$N(CH_3)_2$), or, in the case of —$CONR^uR^v$ or —$SO_2NR^uR^v$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted.

Of special interest are compounds (1) where Ar is quinolinyl optionally substituted with one, two or three substituents independently selected from halo, in particular fluoro, chloro or bromo, $C_{1-4}$ alkyl, in particular methyl, halo($C_{1-4}$)alkyl, in particular trifluoromethyl, aryl, in particular phenyl, and heteroaryl, in particular pyridyl. Preferred are compounds (1) where the quinolinyl is attached via the 6 position, e.g. 3-bromoquinolin-6-yl, 3-chloroquinolin-6-yl, 3-fluoroquinolin-6-yl, 3,8-dibromoquinolin-6-yl, 3-bromo-8-chloroquinolin-6- yl, 3-bromo-8-methylquinolin-6-yl, 3-phenylquinolin-6-yl or 3-pyrid-4-ylquinolin-6-yl. Most preferred are compounds (1) where Ar is 3-bromoquinolin-6-yl, 3,8-dibromoquinolin-6-yl, 3-bromo-8-chloroquinolin-6-yl or 3-bromo-8-methylquinolin-6-yl.

Another group of preferred compounds (1) are those wherein Ar is 3,8-difluoroquinolin-6-yl, 3-fluoro-8-chloroquinolin-6-yl, 3-fluoro-8-bromoquinolin-6-yl, 3-fluoro-8-iodoquinolin-6-yl, 3-fluoro-8-methylquinolin-6-yl, 3,8-dichloroquinolin-6-yl, 3-chloro-8-fluoroquinolin-6-yl, 3-chloro-8-bromoquinolin-6-yl, 3-chloro-8-iodoquinolin-6-yl, 3-chloro-8-methylquinolin-6-yl, 3,8-bromoquinolin-6-yl, 3-bromo-8-chloroquinolin-6-yl, 3-bromo-8-fluoroquinolin-6-yl, 3-bromo-8-iodoquinolin-6-yl, 3-bromo-8-methylquinolin-6-yl, 3,8-iodoquinolin-6-yl, 3-iodo-8-chloroquinolin-6-yl, 3-iodo-8-bromoquinolin-6-yl, 3-iodo-8-fluoroquinolin-6-yl or 3-iodo-8-methylquinolin-6-yl.

Another group of particularly preferred compounds (1) are those wherein Ar is 8-haloquinolin-6-yl or 8-methylquinolin-6-yl.

$R^1$ is typically methyl.

$R^2$ is typically H or methyl, most preferably H.

Preferred values of $R^2$ also includes $C_{1-8}$ alkyl, $C_{3-4}$ cycloalkyl, $C_{2-8}$ alkenyl and cyano($C_{1-4}$)alkyl.

$R^2$ also includes $C_{1-4}$ alkoxy($C_{1-4}$)alkyl, especially $C_{1-4}$ alkoxymethyl, and benzyloxymethyl in which the phenyl ring of the benzyl group optionally carries an alkoxy substituent, e.g. a methoxy substituent.

Of particular interest are compounds (1) where in the definition of $R^3$ p is 1, q, r and s are 0, and $R^a$ and $R^b$ are both methyl or $R^a$ is methyl and $R^b$ is cyano. Of more particular interest are compounds (1) where $R^3$ is tert-butyl, 1,1,1-trifluoro-2-methyl-prop-2-yl, 2-cyanoprop-2-yl, 1-methoxy-2-methylprop-2-yl, 1-methylthio-2-methylprop-2-yl, 1-methoxy-3-methylbut-3-yl, 2-cyano-1-methoxyprop-2-yl, 2-methoxycarbonyl-prop-2-yl or 2-methylaminocarbonyl-prop-2-yl. The most preferred are compounds (1) where $R^3$ is tert-butyl, 1-methoxy-2-methylprop-2-yl or 2-cyano-1-methoxyprop-2-yl.

Of further interest are compounds (1) where $R^3$ is 2-hydroxymethyl-1-methoxy-prop-2-yl or 1-methoxy-2-methoxymethylprop-2-yl.

L is typically O; n is typically 0.

Compounds that form part of the invention are illustrated in Tables 1 to 366 below.

Melting points (mp) and/or diagnostic molecular ion (eg $M^+$, $[M+1]^+$) values are provided in part for compounds in the following tables. Additional spectroscopic (1H NMR) data are provided in Examples 1-13E while biological activities are provided in Example 14.

TABLE 1

The compounds in Table 1 are of the general formula (1) where Ar is 3,5-dichlorophenyl, n is 0, L is O, $R^1$ is methyl, and $R^2$ and $R^3$ have the values given in the table.

| Compound No. | $R^2$ | $R^3$ |
|---|---|---|
| 1 | H | $CH_3$ |
| 2 | $CH_3$ | $CH_3$ |
| 3 | H | $C_2H_5$ |
| 4 | $C_2H_5$ | $C_2H_5$ |
| 5 | H | prop-2-yl |
| 6 | $CH_3$ | prop-2-yl |
| 7 | prop-2-yl | prop-2-yl |
| 8 | $CH_3$ | n-butyl |
| 9 | H | but-2-yl |
| 10 | H | 2-methyl-prop-1-yl |
| 11 | 2-methyl-prop-1-yl | 2-methyl-prop-1-yl |
| 12 | H | tert-$C_4H_9$ |
| 13 | $CH_3$ | tert-$C_4H_9$ |
| 14 | H | pent-2-yl |
| 15 | H | pent-3-yl |
| 16 | H | 2-methyl-but-2-yl |
| 17 | H | 3-methyl-but-1-yl |
| 18 | H | 3-methyl-pent-2-yl |
| 19 | H | 4-methyl-pent-2-yl |
| 20 | H | 3,3-dimethyl-but-2-yl |
| 21 | H | 2-methyl-hex-2-yl |
| 22 | H | 2,4-dimethyl-pent-2-yl |
| 23 | H | 2,4,4-trimethyl-but-2-yl |
| 24 | H | 2,4,4-trimethyl-pent-2-yl |
| 25 | H | Cl-n-$C_3H_6$— |
| 26 | H | Cl—$CH_2(CH_3)_2$C— |
| 27 | H | $F_3C(CH_3)_2$C— |
| 28 | H | NC—$CH_2$— |
| 29 | $CH_3$ | NC—$CH_2$— |
| 30 | NC—$CH_2$— | NC—$CH_2$— |
| 31 | H | $(NC)_2$CH— |
| 32 | H | NC—$C_2H_4$— |
| 33 | $CH_3$ | NC—$C_2H_4$— |
| 34 | NC—$C_2H_4$— | NC—$C_2H_4$— |
| 35 | H | $(CH_3)_2$C(CN)— |
| 36 | H | $C_2H_5(CH_3)$C(CN)— |
| 37 | H | $(C_2H_5)_2$C(CN)— |
| 38 | H | $(CH_3)_2$CH($CH_3$)C(CN)— |
| 39 | H | HO—$CH_2(CH_3)_2$C— |
| 40 | H | HO—$C_2H_4(CH_3)_2$C— |
| 41 | H | 1-hydroxy-2-(hydroxymethyl)-prop-2-yl |

TABLE 1-continued

The compounds in Table 1 are of the general formula (1) where Ar is 3,5-dichlorophenyl, n is 0, L is O, $R^1$ is methyl, and $R^2$ and $R^3$ have the values given in the table.

| Compound No. | $R^2$ | $R^3$ | |
|---|---|---|---|
| 42 | H | 1-hydroxy-2-(methoxymethyl)prop-2-yl | |
| 43 | H | 1-methoxy-2-(methoxymethyl)prop-2-yl | |
| 44 | H | 1-hydroxy-2-(hydroxymethyl)-but-2-yl | |
| 45 | $C_2H_5OC_2H_4$— | $C_2H_5OC_2H_4$— | |
| 46 | $CH_3$ | $(CH_3O)_2CHCH_2$— | |
| 47 | H | $CH_3O$—$CH_2(CH_3)_2C$— | |
| 48 | H | $CH_3O$—$C_2H_4(CH_3)_2C$— | |
| 49 | H | $C_2H_5O$—$C_2H_4(CH_3)_2C$— | |
| 50 | H | $CH_3S$—$CH_2(CH_3)_2C$— | |
| 51 | H | NC—$(CH_3O)CH$— | |
| 52 | H | $CH_3OCH_2(CH_3)C(CN)$— | $M^+$ 363 |
| 53 | H | $CH_3SCH_2(CH_3)C(CN)$— | $M^+$ 379 |
| 54 | H | $CH_3(CO)(CH_3)_2C$— | |
| 55 | H | $CH_3CHBr(CO)(CH_3)_2C$— | |
| 56 | H | $CH_3(CO)(OH)CH(CH_3)_2C$— | |
| 57 | H | $CH_3OC_2H_4(CO)(CH_3)_2C$— | |
| 58 | H | $CH_3(CO)CH_2(CH_3)_2C$— | |
| 59 | H | $CH_3O(CO)(CH_3)CH$— | |
| 60 | H | $CH_3O(CO)(CH_3)_2C$— | |
| 61 | H | $C_2H_5O(CO)C_2H_4$— | |
| 62 | H | $CH_3NH(CO)(CH_3)_2C$— | |
| 63 | H | $(CH_3)_2N(CO)(CH_3)_2C$— | |
| 64 | H | $(CH_3)_3SiCH_2$— | |
| 65 | H | tert-$C_4H_9(CH_3)_2SiO$—$CH_2(CH_3)_2C$— | |
| 66 | H | tert-$C_4H_9(CH_3)_2SiO$—$C_2H_4(CH_3)_2C$— | |
| 67 | H | 4-$FPhCH_2OCH_2(CH_3)_2C$— | |
| 68 | H | $C_2H_5OCH_2(CH_3)_2C$— | |
| 69 | H | $CH_3OCH_2CH_2O(CH_3)_2C$— | |
| 70 | H | $CH_2$=$CHCH_2$— | |
| 71 | $CH_2$=$CHCH_2$— | $CH_2$=$CHCH_2$— | |
| 72 | H | $CH_2$=$C(CH_3)CH_2$— | |
| 73 | H | $CH_2$=$CH(CH_3)CH$— | |
| 74 | H | $CH_2$=$CH(CH_3)_2C$— | |
| 75 | H | $CH_3(CO)CH$=$CH$— | |
| 76 | $CH_3$ | $CH_3(CO)CH$=$CH$— | |
| 77 | H | pent-3-en-2-yl | |
| 78 | H | 2-methyl-hex-3-en-2-yl (E) | |
| 79 | H | 2-methyl-hex-3-en-2-yl (Z) | |
| 80 | H | 2-methyl-pent-4-en-3-on-2-yl | |
| 81 | H | $CH_3O(CO)CH$=$(Cl)C(CH_3)_2C$— | |
| 82 | H | $C_6H_5$—$C(CH_3)$=$CH(CH_3)_2C$— | |
| 83 | $CH_2$=$CHCH_2$— | $CH_2$=$CHCH_2OC_2H_4$— | |
| 84 | H | $CH$≡$CCH_2$— | |
| 85 | $CH_3$ | $CH$≡$CCH_2$— | |
| 86 | H | cycloprop-1-yl | |
| 87 | NC—$C_2H_4$— | cycloprop-1-yl | |
| 88 | cycloprop-1-yl | cycloprop-1-yl | |
| 89 | H | 1-cyano-cycloprop-1-yl | |
| 90 | H | 2-cyano-cycloprop-1-yl | |
| 91 | H | 1-methoxycarbonyl-cycloprop-1-yl | |
| 92 | H | 1-[N,N-dimethylaminocarbonyl]-cycloprop-1-yl | |
| 93 | H | 1-[N-methyl-N-methoxy-aminocarbonyl]-cycloprop-1-yl | |
| 94 | H | 1-cyano-1-cyclopropyl-eth-1-yl | |
| 95 | H | cyclopent-1-yl | |
| 96 | H | 1-cyano-cyclopent-1-yl | |
| 97 | H | cyclohex-1-yl | |
| 98 | $CH_2$=$CHCH_2$— | cyclohex-1-yl | |
| 99 | H | 4-cyano-cyclohex-1-yl | |
| 100 | H | 1-cyano-4-methyl-cyclohex-1-yl | |
| 101 | H | 4-tert-butyl-1-cyano-cyclohex-1-yl | |
| 102 | H | 2-methyl-3-cyanotetrahydrofuran-3-yl | |
| 103 | H | 5-methyl-1,3-dioxolan-5-yl | |
| 104 | H | 5-ethyl-1,3-dioxolan-5-yl | |

TABLE 1-continued

The compounds in Table 1 are of the general formula (1) where Ar is 3,5-dichlorophenyl, n is 0, L is O, $R^1$ is methyl, and $R^2$ and $R^3$ have the values given in the table.

| Compound No. | $R^2$ | $R^3$ |
|---|---|---|
| 105 | H | 3,5-dimethyl-1,3-dioxolan-5-yl |
| 106 | H | N-ethoxycarbonyl-piperid-4-yl |
| 107 | H | morpholino |
| 108 | H | cyclohex-1-yl-methyl |
| 109 | H | 4-cyano-cyclopenten-3-yl |
| 110 | H | 5-tert-butyl-2H-1,3,4-thiadiazin-2-yl |
| 111 | H | 2-(cyclohexen-1-yl)-eth-1-yl |
| 112 | H | fur-2-yl |
| 113 | H | 5-methoxycarbonyl-fur-2-yl |
| 114 | H | thien-2-yl |
| 115 | H | 2-methoxycarbonyl-thien-3-yl |
| 116 | H | 4-methoxycarbonyl-thien-3-yl |
| 117 | H | oxazol-2-yl |
| 118 | H | 5-methyl-isoxazol-3-yl |
| 119 | H | 4-cyano-3-methyl-isoxazol-5-yl |
| 120 | H | thiazol-2-yl |
| 121 | H | 5-ethylthio-1,3,4-thiadiazol-2- |
| 122 | H | fur-2-ylmethyl |
| 123 | H | cyanofur-1-ylmethyl |
| 124 | H | thien-2-ylmethyl |
| 125 | H | $C_6H_5$— |
| 126 | H | 2-Cl—$C_6H_4$— |
| 127 | H | 2-I—$C_6H_4$— |
| 128 | H | 2-NC—$C_6H_4$— |
| 129 | H | 3-$CF_3$—$C_6H_4$— |
| 130 | H | 3-$CH_3S$—$C_6H_4$— |
| 131 | H | 3-$CH_3O(CO)$—$C_6H_4$— |
| 132 | H | 4-Cl—$C_6H_4$— |
| 133 | H | 4-F—$C_6H_4$— |
| 134 | H | 4-$CF_3O$—$C_6H_4$— |
| 135 | H | 4-$(C_2H_5)_2N$—$C_6H_4$— |
| 136 | H | 4-(N-methyl-N-acetyl-amino)-phenyl |
| 137 | H | 2,4-dichlorophenyl |
| 138 | H | 4-methoxy-2-methylphenyl |
| 139 | H | 3,4-dichlorophenyl |
| 140 | H | 3-chloro-4-fluorophenyl |
| 141 | H | 2,5-difluorophenyl |
| 142 | H | 5-fluoro-2-methylphenyl |
| 143 | H | 5,6,7,8-tetrahydronaphth-2-yl |
| 144 | H | 2,3-dihydrobenzofuran-5-yl-methyl |
| 145 | H | 5-cyano-4,6-dimethoxy-pyrid-2-yl |
| 146 | H | 2,6-dimethoxy-pyrid-3-yl |
| 147 | H | 6-chloro-pyridazin-3-yl |
| 148 | H | 4,6-dimethoxy-pyrimid-2-yl |
| 149 | H | 2-chloro-5-fluoro-pyrimid-6-yl |
| 150 | H | $C_6H_5CH_2$— |
| 151 | $CH_3$ | $C_6H_5CH_2$— |
| 152 | H | 2-F—$C_6H_4CH_2$— |
| 153 | H | 2-Cl—$C_6H_4CH_2$— |
| 154 | $CH_3$ | 2-Cl—$C_6H_4CH_2$— |
| 155 | H | 2-$NO_2$—$C_6H_4CH_2$— |
| 156 | H | 2-$CH_3$—$C_6H_4CH_2$— |
| 157 | H | 2-$CH_3O$—$C_6H_4CH_2$— |
| 158 | H | 2-$CHF_2O$—$C_6H_4CH_2$— |
| 159 | H | 2-$CH_3S$—$C_6H_4CH_2$— |
| 160 | H | 2-$CF_3S$—$C_6H_4CH_2$— |
| 161 | H | 3-Cl—$C_6H_4CH_2$— |
| 162 | H | 3-I—$C_6H_4CH_2$— |
| 163 | H | 3-$CH_3$—$C_6H_4CH_2$— |
| 164 | H | 3-$CH_3O$—$C_6H_4CH_2$— |
| 165 | H | 4-F—$C_6H_4CH_2$— |
| 166 | H | 4-Cl—$C_6H_4CH_2$— |
| 167 | H | 4-$CH_3$—$C_6H_4CH_2$— |
| 168 | H | 4-$CF_3$—$C_6H_4CH_2$— |
| 169 | H | 4-$CH_3O$—$C_6H_4CH_2$— |
| 170 | H | 4-$CF_3O$—$C_6H_4CH_2$— |
| 171 | H | 2,6-di-F—$C_6H_3CH_2$— |
| 172 | 3-methyl-but-2-en-1-yl | 2,5-di-F—$C_6H_3CH_2$— |

TABLE 1-continued

The compounds in Table 1 are of the general formula (1) where Ar is 3,5-dichlorophenyl, n is 0, L is O, $R^1$ is methyl, and $R^2$ and $R^3$ have the values given in the table.

| Compound No. | $R^2$ | $R^3$ | |
|---|---|---|---|
| 173 | H | 2-F-4-Cl—$C_6H_3CH_2$— | |
| 174 | H | 2-F-6-Cl—$C_6H_3CH_2$— | |
| 175 | H | 2,6-di-Cl—$C_6H_3CH_2$— | |
| 176 | 4-methyl-pent-2-en-1-yl | 3,4-di-Cl—$C_6H_3CH_2$— | |
| 177 | H | 2-F-6-$CH_3O$—$C_6H_3CH_2$— | |
| 178 | H | 2,4,5-tri-F—$C_6H_2CH_2$— | |
| 179 | H | 2,4-di-Cl-6-$CH_3$—$C_6H_2CH_2$— | |
| 180 | H | 3,4,5-tri-$CH_3O$—$C_6H_2CH_2$— | |
| 181 | H | $C_6H_5$—$CH(CH_3)$— | |
| 182 | H | 4-F—$C_6H_4$—$CH(CH_3)$— | |
| 183 | H | 4-$NO_2$—$C_6H_4$—$CH(CH_3)$— | |
| 184 | H | 4-n-pentyl-$C_6H_4$—$CH(CH_3)$— | |
| 185 | H | 4-$CH_3SO_2$—$C_6H_4$—$CH(CH_3)$— | |
| 186 | H | $C_6H_5(CO)CH_2$— | |
| 187 | H | $C_6H_5$—CH(CN)— | |
| 188 | H | $C_6H_5$—$(CH_3O)CH$— | |
| 189 | H | $C_6H_5$—$(CH_3)_2C$— | |
| 190 | H | m-Cl—$C_6H_5$—$(CH_3)_2C$— | |
| 191 | H | 3,5-di-Cl—$C_6H_3$—$(CH_3)_2C$— | |
| 192 | H | $C_6H_5$—$(C_2H_5O(CO))CH$— | |
| 193 | H | phenethyl | |
| 194 | H | 3-methoxy-4-propargyloxy-phenethyl | |
| 195 | H | 3-methoxy-4-(pent-2-yn-1-yloxy)-phenethyl | |
| 196 | H | 2-methyl-3-phenyl-prop-2-yl | |
| 197 | H | $C_6H_5O$—$C_2H_4$— | |
| 198 | H | 4-F—$C_6H_4$—$CH_2OCH_2(CH_3)_2C$— | |
| 199 | H | $C_6H_5$—$CH_2O(CO)C_2H_4$— | |
| 200 | H | naphth-2-yl-$(CH_3)CH$— | |
| 201 | NC—$C_2H_4$— | pyrid-3-ylmethyl | |
| 202 | $CH_3$ | 2-pyrid-2-yleth-1-yl | |
| 203 | H | 2-(3-chloro-5-trifluoromethyl-pyrid-2-yl)oxyeth-1-yl | |
| 204 | H | 2-methyl-4-pyrazin-2-yl-but-3-on-2-yl | |
| 205 | —$(CH_2)_4$— | | |
| 206 | —$(CH_2)_5$— | | |
| 207 | —$(CH_2)_4CH(C_2H_5)$— | | |
| 208 | —$C_3H_6CH[(CO)N(C_2H_5)_2]CH_2$— | | |
| 209 | —$CH(CH_3)CH=CHCH(CH_3)$— | | |
| 210 | —$CH_2$—[cyclohexyl]—$C_2H_4$— | | |
| 211 | —$C_2H_4OC_2H_4$— | | |
| 212 | —$CH_2CH(CH_3)OCH(CH_3)CH_2$— | | |
| 213 | —$C_2H_4SCH_2$— | | |
| 214 | —$C_2H_4SC_2H_4$— | | |
| 215 | —$(CH_2)_2NH(CH_2)_2$— | | |
| 216 | —$(CH_2)_2N(p-NO_2—C_6H_4)(CH_2)_2$— | | |
| 217 | —$(CH_2)_2N(m-CF_3—C_6H_4)(CH_2)_2$— | | |
| 218 | —$(CH_2)_2N(p-CH_3CO—C_6H_4)(CH_2)_2$— | | |
| 219 | —$(CH_2)_2N(pyrid-2-yl)(CH_2)_2$— | | |
| 220 | H | $(H_2C=CHCH_2OCH_2)(CH_3)_2C$— | |
| 221 | H | $(HCCHCH_2OCH_2)(CH_3)_2C$— | |
| 222 | H | $(CH_3CH_2OCH_2)(CH_3)_2C$— | |
| 223 | H | $((CH_3)_2CHOCH_2)(CH_3)_2C$— | |
| 224 | H | $C_6H_5CH_2OCH_2(CH_3)_2C$— | |
| 225 | H | $(CH_3CH_2OCH_2)(CH_3)_2C$— | |
| 226 | H | 4-F—$C_6H_4$—$CH_2(CH_3)C(CN)$— | $M^+$ 427 |
| 227 | H | 4-Cl—$C_6H_4$—$CH_2(CH_3)C(CN)$— | $[M + 2]^+$ 445 |
| 228 | H | 4-$CH_3O$—$C_6H_4$—$CH_2CH(C_2H_5)C(CN)$— | $M^+$ 453 |
| 229 | H | 2-Cl—$C_6H_4$—$CH_2(CH_3)C(CN)$— | $[M + 2]^+$ 445 |
| 230 | H | $(CH_3)_2CH$—$CH_2(CH_3)C(CN)$— | $M^+$ 375 |
| 231 | H | 1-methoxymethyl-cycloprop-1-yl | |
| 232 | H | 1-benzyloxymethyl-cycloprop-1-yl | $M^+$ 426 |
| 233 | H | 1-methoxymethoxy-2-methyl- | |

TABLE 1-continued

The compounds in Table 1 are of the general formula (1) where Ar is 3,5-dichlorophenyl, n is 0, L is O, $R^1$ is methyl, and $R^2$ and $R^3$ have the values given in the table.

| Compound No. | $R^2$ | $R^3$ |
|---|---|---|
| | | prop-2-yl |
| 234 | H | 1-(2-methoxy-ethoxymethoxy)-2-methyl-prop-2-yl |
| 235 | H | 1-cyclopropyl-eth-1-yl |
| 236 | H | 2-fluoro-eth-1-yl |
| 237 | H | 2,2,2-trifluoro-1-methyl-eth-1-yl |

Table 2

The compounds in Table 2 are of the general formula (1) where Ar is 3,5-dibromophenyl, n is 0, L is O, $R^1$ is methyl, and $R^2$ and $R^3$ have the values listed in Table 1. Thus compound 1 of Table 2 is the same as compound 1 of Table 1 except that in compound 1 of Table 2 Ar is 3,5-dibromophenyl instead of 3,5-dichlorophenyl. Similarly, compounds 2 to 237 of Table 2 are the same as compounds 2 to 237 of Table 1, respectively, except that in the compounds of Table 2 Ar is 3,5-dibromophenyl instead of 3,5-dichlorophenyl.

Table 3

The compounds in Table 3 are of the general formula (1) where Ar is 3,5-difluorophenyl, n is 0, L is O, $R^1$ is methyl, and $R^2$ and $R^3$ have the values listed in Table 1. Thus compound 1 of Table 3 is the same as compound 1 of Table 1 except that in compound 1 of Table 3 Ar is 3,5-difluorophenyl instead of 3,5-dichlorophenyl. Similarly, compounds 2 to 237 of Table 3 are the same as compounds 2 to 237 of Table 1, respectively, except that in the compounds of Table 3 Ar is 3,5-difluorophenyl instead of 3,5-dichlorophenyl.

Table 4

The compounds in Table 4 are of the general formula (1) where Ar is 3,5-dimethylphenyl, n is 0, L is O, $R^1$ is methyl, and $R^2$ and $R^3$ have the values listed in Table 1. Thus compound 1 of Table 4 is the same as compound 1 of Table 1 except that in compound 1 of Table 4 Ar is 3,5-dimethylphenyl instead of 3,5-dichlorophenyl. Similarly, compounds 2 to 237 of Table 4 are the same as compounds 2 to 237 of Table 1, respectively, except that in the compounds of Table 4 Ar is 3,5-dimethylphenyl instead of 3,5-dichlorophenyl.

Table 5

The compounds in Table 5 are of the general formula (1) where Ar is 3-chloro-5-methylphenyl, n is 0, L is O, $R^1$ is methyl, and $R^2$ and $R^3$ have the values listed in Table 1. Thus compound 1 of Table 5 is the same as compound 1 of Table 1 except that in compound 1 of Table 5 Ar is 3-chloro-5-methylphenyl instead of 3,5-dichlorophenyl. Similarly, compounds 2 to 237 of Table 5 are the same as compounds 2 to 237 of Table 1, respectively, except that in the compounds of Table 5 Ar is 3-chloro-5-methylphenyl instead of 3,5-dichlorophenyl.

Table 6

The compounds in Table 6 are of the general formula (1) where Ar is 3,5-bis(trifluoromethyl)phenyl, n is 0, L is O, $R^1$ is methyl, and $R^2$ and $R^3$ have the values listed in Table 1. Thus compound 1 of Table 6 is the same as compound 1 of Table 1 except that in compound 1 of Table 6 Ar is 3,5-bis(trifluoromethyl)phenyl instead of 3,5-dichlorophenyl. Similarly, compounds 2 to 237 of Table 6 are the same as compounds 2 to 237 of Table 1, respectively, except that in the compounds of Table 6 Ar is 3,5-bis(trifluoromethyl)phenyl instead of 3,5-dichlorophenyl.

Table 7

The compounds in Table 7 are of the general formula (1) where Ar is 3-ethyl-5-methylphenyl, n is 0, L is O, $R^1$ is methyl, and $R^2$ and $R^3$ have the values listed in Table 1. Thus compound 1 of Table 7 is the same as compound 1 of Table 1 except that in compound 1 of Table 7 Ar is 3-ethyl-5-methylphenyl instead of 3,5-dichlorophenyl. Similarly, compounds 2 to 237 of Table 7 are the same as compounds 2 to 237 of Table 1, respectively, except that in the compounds of Table 7 Ar is 3-ethyl-5-methylphenyl instead of 3,5-dichlorophenyl.

Table 8

The compounds in Table 8 are of the general formula (1), where Ar is 3,5-dimethoxy-phenyl, n is 0, L is O, $R^1$ is methyl, and $R^2$ and $R^3$ have the values listed in Table 1. Thus compound 1 of Table 8 is the same as compound 1 of Table 1 except that in compound 1 of Table 8 Ar is 3,5-dimethoxyphenyl instead of 3,5-dichlorophenyl. Similarly, compounds 2 to 237 of Table 8 are the same as compounds 2 to 237 of Table 1, respectively, except that in the compounds of Table 8 Ar is 3,5-dimethoxyphenyl instead of 3,5-dichlorophenyl.

Table 9

The compounds in Table 9 are of the general formula (1) where Ar is 3-chloro-5-methoxyphenyl, n is 0, L is O, $R^1$ is methyl, and $R^2$ and $R^3$ have the values listed in Table 1. Thus compound 1 of Table 9 is the same as compound 1 of Table 1 except that in compound 1 of Table 9 Ar is 3-chloro-5-methoxyphenyl instead of 3,5-dichlorophenyl. Similarly, compounds 2 to 237 of Table 9 are the same as compounds 2 to 237 of Table 1, respectively, except that in the compounds of Table 9 Ar is 3-chloro-5-methoxyphenyl instead of 3,5-dichlorophenyl.

Table 10

The compounds in Table 10 are of the general formula (1) where Ar is 3-cyano-5-methoxyphenyl, n is 0, L is O, $R^1$ is methyl, and $R^2$ and $R^3$ have the values listed in Table 1. Thus compound 1 of Table 10 is the same as compound 1 of Table 1 except that in compound 1 of Table 10 Ar is 3-cyano-5-methoxyphenyl instead of 3,5-dichlorophenyl. Similarly, compounds 2 to 237 of Table 10 are the same as compounds 2 to 237 of Table 1, respectively, except that in the compounds of Table 10 Ar is 3-cyano-5-methoxyphenyl instead of 3,5-dichlorophenyl.

Table 11

The compounds in Table 11 are of the general formula (1) where Ar is 3,4,5-trichlorophenyl, n is 0, L is O, $R^1$ is methyl, and $R^2$ and $R^3$ have the values listed in Table 1. Thus compound 1 of Table 11 is the same as compound 1 of Table 1 Ar is 3,4,5-trichlorophenyl instead of 3,5-dichlorophenyl. Similarly, compounds 2 to 237 of Table 11 are the same as compounds 2 to 237 of Table 1, respectively, except that in the compounds of Table 11 Ar is 3,4,5-trichlorophenyl instead of 3,5-dichlorophenyl.

Table 12
The compounds in Table 12 are of the general formula (1) where Ar is 3,5-dibromo-4-methylphenyl, n is 0, L is O, $R^1$ is methyl, and $R^2$ and $R^3$ have the values listed in Table 1. Thus compound 1 of Table 12 is the same as compound 1 of Table 1 except that in compound 1 of Table 12 Ar is 3,5-dibromo-4-methylphenyl instead of 3,5-dichlorophenyl. Similarly, compounds 2 to 237 of Table 12 are the same as compounds 2 to 237 of Table 1, respectively, except that in the compounds of Table 12 Ar is 3,5-dibromo-4-methylphenyl instead of 3,5-dichlorophenyl.

Table 13
The compounds in Table 13 are of the general formula (1) where Ar is 3,4,5-trimethylphenyl, n is 0, L is O, $R^1$ is methyl, and $R^2$ and $R^3$ have the values listed in Table 1. Thus compound 1 of Table 13 is the same as compound 1 of Table 1 except that in compound 1 of Table 13 Ar is 3,4,5-trimethylphenyl instead of 3,5-dichlorophenyl. Similarly, compounds 2 to 237 of Table 13 are the same as compounds 2 to 237 of Table 1, respectively, except that in the compounds of Table 13 Ar is 3,4,5-trimethylphenyl instead of 3,5-dichlorophenyl.

The preparation of 2-(3,4,5-trimethylphenoxy)-2-methylthio-N-(2-methyl-prop-2-yl)acetamide (Compound No. 12 of Table 13), is described in Example 2, page 73.

$^1$H NMR characterisation of compound No.s 12, 52, 70, 120, 124 and 150 of Table 13 is provided on page 76.

Table 14
The compounds in Table 14 are of the general formula (1) where Ar is 3,5-dimethyl-4-chlorophenyl, n is 0, L is O, $R^1$ is methyl, and $R^2$ and $R^3$ have the values listed in Table 1. Thus compound 1 of Table 14 is the same as compound 1 of Table 1 except that in compound 1 of Table 14 Ar is 3,5-dimethyl-4-chlorophenyl instead of 3,5-dichlorophenyl. Similarly, compounds 2 to 237 of Table 14 are the same as compounds 2 to 237 of Table 1, respectively, except that in the compounds of Table 14 Ar is 3,5-dimethyl-4-chlorophenyl instead of 3,5-dichlorophenyl.

Table 15
The compounds in Table 15 are of the general formula (1) where Ar 3,5-dimethyl-4-bromophenyl, n is 0, L is O, $R^1$ is methyl, and $R^2$ and $R^3$ have the values listed in Table 1. Thus compound 1 of Table 15 is the same as compound 1 of Table 1 except that in compound 1 of Table 15 Ar is 3,5-dimethyl-4-bromophenyl instead of 3,5-dichlorophenyl. Similarly, compounds 2 to 237 of Table 15 are the same as compounds 2 to 237 of Table 1, respectively, except that in the compounds of Table 15 Ar is 3,5-dimethyl-4-bromophenyl instead of 3,5-dichlorophenyl.

| Compound No. | $R^2$ | $R^3$ | |
|---|---|---|---|
| 52 | H | $CH_3OCH_2(CH_3)C(CN)$— | $[M + 2]^+$ 403 |

Table 16
The compounds in Table 16 are of the general formula (1) where Ar is 3,5-dimethyl-4-methylthiophenyl, n is 0, L is O, $R^1$ is methyl, and $R^2$ and $R^3$ have the values listed in Table 1. Thus compound 1 of Table 16 is the same as compound 1 of Table 1 except that in compound 1 of Table 16 Ar is 3,5-dimethyl-4-methylthiophenyl instead of 3,5-dichlorophenyl. Similarly, compounds 2 to 237 of Table 16 are the same as compounds 2 to 237 of Table 1, respectively, except that in the compounds of Table 16 Ar is 3,5-dimethyl-4-methylthiophenyl instead of 3,5-dichlorophenyl.

Table 17
The compounds in Table 17 are of the general formula (1) where Ar is 4-cyano-3,5-dimethylphenyl, n is 0, L is O, $R^1$ is methyl, and $R^2$ and $R^3$ have the values listed in Table 1. Thus compound 1 of Table 17 is the same as compound 1 of Table 1 except that in compound 1 of Table 17 Ar is 4-cyano-3,5-dimethylphenyl instead of 3,5-dichlorophenyl. Similarly, compounds 2 to 237 of Table 17 are the same as compounds 2 to 237 of Table 1, respectively, except that in the compounds of Table 17 Ar is 4-cyano-3,5-dimethylphenyl instead of 3,5-dichlorophenyl.

Table 18
The compounds in Table 18 are of the general formula (1) where Ar is 3,4-dichlorophenyl, n is 0, L is O, $R^1$ is methyl, and $R^2$ and $R^3$ have the values listed in Table 1. Thus compound 1 of Table 18 is the same as compound 1 of Table 1 except that in compound 1 of Table 18 Ar is 3,4-dichlorophenyl instead of 3,5-dichlorophenyl. Similarly, compounds 2 to 237 of Table 18 are the same as compounds 2 to 237 of Table 1, respectively, except that in the compounds of Table 18 Ar is 3,4-dichlorophenyl instead of 3,5-dichlorophenyl.

Table 19
The compounds in Table 19 are of the general formula (1) where Ar is 3-chloro-4-methylphenyl, n is 0, L is O, $R^1$ is methyl, and $R^2$ and $R^3$ have the values listed in Table 1. Thus compound 1 of Table 19 is the same as compound 1 of Table 1 except that in compound 1 of Table 19 Ar is 3-chloro-4-methylphenyl instead of 3,5-dichlorophenyl. Similarly, compounds 2 to 237 of Table 19 are the same as compounds 2 to 237 of Table 1, respectively, except that in the compounds of Table 19 Ar is 3-chloro-4-methylphenyl instead of 3,5-dichlorophenyl.

Table 20
The compounds in Table 20 are of the general formula (1) where Ar 3-methyl-4-chlorophenyl, n is 0, L is O, $R^1$ is methyl, and $R^2$ and $R^3$ have the values listed in Table 1. Thus compound 1 of Table 20 is the same as compound 1 of Table 1 except that in compound 1 of Table 20 Ar is 3-methyl-4-chlorophenyl instead of 3,5-dichlorophenyl. Similarly, compounds 2 to 237 of Table 20 are the same as compounds 2 to 237 of Table 1, respectively, except that in the compounds of Table 20 Ar is 3-methyl-4-chlorophenyl instead of 3,5-dichlorophenyl.

Table 21
The compounds in Table 21 are of the general formula (1) where Ar is 3-chloro-4-cyanophenyl, n is 0, L is O, $R^1$ is methyl, and $R^2$ and $R^3$ have the values listed in Table 1. Thus compound 1 of Table 21 is the same as compound 1 of Table 1 except that in compound 1 of Table 21 Ar is 3-chloro-4-cyanophenyl instead of 3,5-dichlorophenyl. Similarly, compounds 2 to 237 of Table 21 are the same as compounds 2 to 237 of Table 1, respectively, except that in the compounds of Table 21 Ar is 3-chloro-4-cyanophenyl instead of 3,5-dichlorophenyl.

Table 22
The compounds in Table 22 are of the general formula (1) where Ar is 3-methyl-4-methylthiophenyl, n is 0, L is O, $R^1$ is methyl, and $R^2$ and $R^3$ have the values listed in Table 1. Thus compound 1 of Table 22 is the same as compound 1 of Table 1 except that in compound 1 of Table 22 Ar is 3-methyl-4-methylthiophenyl instead of 3,5-dichlorophenyl. Similarly, compounds 2 to 237 of Table 22 are the same as compounds 2 to 237 of Table 1, respectively, except that in the compounds of Table 22 Ar is 3-methyl-4-methylthiophenyl instead of 3,5-dichlorophenyl.

Table 23

The compounds in Table 23 are of the general formula (1) where Ar is 3-chlorophenyl, n is 0, L is O, $R^1$ is methyl, and $R^2$ and $R^3$ have the values listed in Table 1. Thus compound 1 of Table 23 is the same as compound 1 of Table 1 except that in compound 1 of Table 23 Ar is 3-chlorophenyl instead of 3,5-dichlorophenyl. Similarly, compounds 2 to 237 of Table 23 are the same as compounds 2 to 237 of Table 1, respectively, except that in the compounds of Table 23 3-chlorophenyl instead of 3,5-dichlorophenyl.

Table 24

The compounds in Table 24 are of the general formula (1) where Ar is 3-trifluoromethylphenyl, n is 0, L is O, $R^1$ is methyl, and $R^2$ and $R^3$ have the values listed in Table 1. Thus compound 1 of Table 24 is the same as compound 1 of Table 1 except that in compound 1 of Table 24 Ar is 3-trifluoromethylphenyl instead of 3,5-dichlorophenyl. Similarly, compounds 2 to 237 of Table 24 are the same as compounds 2 to 237 of Table 1, respectively, except that in the compounds of Table 24 Ar is 3-trifluoromethylphenyl instead of 3,5-dichlorophenyl.

Table 25

The compounds in Table 25 are of the general formula (1) where Ar is 3-trifluoromethoxyphenyl, n is 0, L is O, $R^1$ is methyl, and $R^2$ and $R^3$ have the values listed in Table 1. Thus compound 1 of Table 25 is the same as compound 1 of Table 1 except that in compound 1 of Table 25 Ar is 3-trifluoromethoxyphenyl instead of 3,5-dichlorophenyl. Similarly, compounds 2 to 237 of Table 25 are the same as compounds 2 to 237 of Table 1, respectively, except that in the compounds of Table 25 Ar is 3-trifluoromethoxyphenyl instead of 3,5-dichlorophenyl.

Table 26

The compounds in Table 26 are of the general formula (1) where Ar is 3-nitrophenyl, n is 0, L is O, $R^1$ is methyl, and $R^2$ and $R^3$ have the values listed in Table 1. Thus compound 1 of Table 26 is the same as compound 1 of Table 1 except that in compound 1 of Table 26 Ar is 3-nitrophenyl instead of 3,5-dichlorophenyl. Similarly, compounds 2 to 237 of Table 26 are the same as compounds 2 to 237 of Table 1, respectively, except that in the compounds of Table 26 Ar is 3-nitrophenyl instead of 3,5-dichlorophenyl.

Table 27

The compounds in Table 27 are of the general formula (1) where Ar is 3-acetylphenyl, n is 0, L is O, $R^1$ is methyl, and $R^2$ and $R^3$ have the values listed in Table 1. Thus compound 1 of Table 27 is the same as compound 1 of Table 1 except that in compound 1 of Table 27 Ar is 3-acetylphenyl instead of 3,5-dichlorophenyl. Similarly, compounds 2 to 237 of Table 27 are the same as compounds 2 to 237 of Table 1, respectively, except that in the compounds of Table 27 Ar is 3-acetylphenyl instead of 3,5-dichlorophenyl.

Table 28

The compounds in Table 28 are of the general formula (1) where Ar is 4-chlorophenyl, n is 0, L is O, $R^1$ is methyl, and $R^2$ and $R^3$ have the values listed in Table 1. Thus compound 1 of Table 28 is the same as compound 1 of Table 1 except that in compound 1 of Table 28 Ar is 4-chlorophenyl instead of 3,5-dichlorophenyl. Similarly, compounds 2 to 237 of Table 28 are the same as compounds 2 to 237 of Table 1, respectively, except that in the compounds of Table 28 Ar is 4-chlorophenyl instead of 3,5-dichlorophenyl.

Table 29

The compounds in Table 29 are of the general formula (1) where Ar is 4-bromophenyl, n is 0, L is O, $R^1$ is methyl, and $R^2$ and $R^3$ have the values listed in Table 1. Thus compound 1 of Table 29 is the same as compound 1 of Table 1 except that in compound 1 of Table 29 Ar is 4-bromophenyl instead of 3,5-dichlorophenyl. Similarly, compounds 2 to 237 of Table 29 are the same as compounds 2 to 237 of Table 1, respectively, except that in the compounds of Table 29 Ar is 4-bromophenyl instead of 3,5-dichlorophenyl.

Table 30

The compounds in Table 30 are of the general formula (1) where Ar is p-tolyl, n is 0, L is O, $R^1$ is methyl, and $R^2$ and $R^3$ have the values listed in Table 1. Thus compound 1 of Table 30 is the same as compound 1 of Table 1 except that in compound 1 of Table 30 Ar is p-tolyl instead of 3,5-dichlorophenyl. Similarly, compounds 2 to 237 of Table 30 are the same as compounds 2 to 237 of Table 1, respectively, except that in the compounds of Table 30 Ar is p-tolyl instead of 3,5-dichlorophenyl.

Table 31

The compounds in Table 31 are of the general formula (1) where Ar is 4-trifluoromethylphenyl, n is 0, L is O, $R^1$ is methyl, and $R^2$ and $R^3$ have the values listed in Table 1. Thus compound 1 of Table 31 is the same as compound 1 of Table 1 except that in compound 1 of Table 31 Ar is 4-trifluoromethylphenyl instead of 3,5-dichlorophenyl. Similarly, compounds 2 to 237 of Table 31 are the same as compounds 2 to 237 of Table 1, respectively, except that in the compounds of Table 31 Ar is 4-trifluoromethylphenyl instead of 3,5-dichlorophenyl.

Table 32

The compounds in Table 32 are of the general formula (1) where Ar is 4-tert-butyl-phenyl, n is 0, L is O, $R^1$ is methyl, and $R^2$ and $R^3$ have the values listed in Table 1. Thus compound 1 of Table 32 is the same as compound 1 of Table 1 except that in compound 1 of Table 32 Ar is 4-tert-butylphenyl instead of 3,5-dichlorophenyl. Similarly, compounds 2 to 237 of Table 32 are the same as compounds 2 to 237 of Table 1, respectively, except that in the compounds of Table 32 Ar is 4-tert-butylphenyl instead of 3,5-dichlorophenyl.

Table 33

The compounds in Table 33 are of the general formula (1) where Ar is 4-cyanophenyl, n is 0, L is O, $R^1$ is methyl, and $R^2$ and $R^3$ have the values listed in Table 1. Thus compound 1 of Table 33 is the same as compound 1 of Table 1 except that in compound 1 of Table 33 Ar is 4-cyanophenyl instead of 3,5-dichlorophenyl. Similarly, compounds 2 to 237 of Table 33 are the same as compounds 2 to 237 of Table 1, respectively, except that in the compounds of Table 33 Ar is 4-cyanophenyl instead of 3,5-dichlorophenyl.

Table 34

The compounds in Table 34 are of the general formula (1) where Ar is 4-pentafluorosulphanylphenyl, n is 0, L is O, $R^1$ is methyl, and $R^2$ and $R^3$ have the values listed in Table 1. Thus compound 1 of Table 34 is the same as compound 1 of Table 1 except that in compound 1 of Table 34 Ar is 4-pentafluorosulphanylphenyl instead of 3,5-dichlorophenyl. Similarly, compounds 2 to 237 of Table 34 are the same as compounds 2 to 237 of Table 1, respectively, except that in the compounds of Table 34 Ar is 4-pentafluorosulphanylphenyl instead of 3,5-dichlorophenyl.

Table 35

The compounds in Table 35 are of the general formula (1) where Ar is 4-nitrophenyl, n is 0, L is O, $R^1$ is methyl, and $R^2$ and $R^3$ have the values listed in Table 1. Thus compound 1 of Table 35 is the same as compound 1 of Table 1 except that in compound 1 of Table 35 Ar is 4-nitrophenyl instead of 3,5-dichlorophenyl. Similarly, compounds 2 to 237 of Table 35 are the same as compounds 2 to 237 of Table 1, respectively, except that in the compounds of Table 35 Ar is 4-nitrophenyl instead of 3,5-dichlorophenyl.

Table 36

The compounds in Table 36 are of the general formula (1) where Ar is indan-5-yl, n is 0, L is O, $R^1$ is methyl, and $R^2$ and $R^3$ have the values given in Table 1. Thus compound 1 of Table 36 is the same as compound 1 of Table 1 except that in compound 1 of Table 36 Ar is indan-5-yl instead of 3,5-dichlorophenyl. Similarly, compounds 2 to 237 of Table 36 are the same as compounds 2 to 237 of Table 1, respectively, except that in the compounds of Table 36 Ar is indan-5-yl instead of 3,5-dichlorophenyl.

| Compound No. | $R^2$ | $R^3$ | |
|---|---|---|---|
| 12 | H | tert-$C_4H_9$ | oil |

Table 37

The compounds in Table 37 are of the general formula (1) where Ar is 1,3-benzodioxol-5-yl, n is 0, L is O, $R^1$ is methyl, and $R^2$ and $R^3$ have the values given in Table 1. Thus compound 1 of Table 37 is the same as compound 1 of Table 1 except that in compound 1 of Table 37 Ar is 1,3-benzodioxol-5-yl instead of 3,5-dichlorophenyl. Similarly, compounds 2 to 237 of Table 37 are the same as compounds 2 to 237 of Table 1, respectively, except that in the compounds of Table 37 Ar is 1,3-benzodioxol-5-yl instead of 3,5-dichlorophenyl.

Table 38

The compounds in Table 38 are of the general formula (1) where Ar is 2-oxo-1,3-benzodioxol-5-yl, n is 0, L is O, $R^1$ is methyl, and $R^2$ and $R^3$ have the values given in Table 1. Thus compound 1 of Table 38 is the same as compound 1 of Table 1 except that in compound 1 of Table 38 Ar is 2-oxo-1,3-benzodioxol-5-yl instead of 3,5-dichlorophenyl. Similarly, compounds 2 to 237 of Table 38 are the same as compounds 2 to 237 of Table 1, respectively, except that in the compounds of Table 38 Ar is 2-oxo-1,3-benzodioxol-5-yl instead of 3,5-dichlorophenyl.

Table 39

The compounds in Table 39 are of the general formula (1) where Ar is 2-thioxo-1,3-benzodioxol-5-yl, n is 0, L is O, $R^1$ is methyl, and $R^2$ and $R^3$ have the values given in Table 1. Thus compound 1 of Table 39 is the same as compound 1 of Table 1 except that in compound 1 of Table 39 Ar is 2-thioxo-1,3-benzodioxol-5-yl instead of 3,5-dichlorophenyl. Similarly, compounds 2 to 237 of Table 39 are the same as compounds 2 to 237 of Table 1, respectively, except that in the compounds of Table 39 Ar is 2-thioxo-1,3-benzodioxol-5-yl instead of 3,5-dichlorophenyl.

Table 40

The compounds in Table 40 are of the general formula (1) where Ar is 1,3-benzoxathiol-5-yl, n is 0, L is O, $R^1$ is methyl, and $R^2$ and $R^3$ have the values given in Table 1. Thus compound 1 of Table 40 is the same as compound 1 of Table 1 except that in compound 1 of Table 40 Ar is 1,3-benzoxathiol-5-yl instead of 3,5-dichlorophenyl. Similarly, compounds 2 to 237 of Table 40 are the same as compounds 2 to 237 of Table 1, respectively, except that in the compounds of Table 40 Ar is 1,3-benzoxathiol-5-yl instead of 3,5-dichlorophenyl.

Table 41

The compounds in Table 41 are of the general formula (1) where Ar is 2-oxo-1,3-benzoxathiol-5-yl, n is 0, L is O, $R^1$ is methyl, and $R^2$ and $R^3$ have the values given in Table 1. Thus compound 1 of Table 41 is the same as compound 1 of Table 1 except that in compound 1 of Table 41 Ar is 2-oxo-1,3-benzoxathiol-5-yl instead of 3,5-dichlorophenyl. Similarly, compounds 2 to 237 of Table 41 are the same as compounds 2 to 237 of Table 1, respectively, except that in the compounds of Table 41 Ar is 2-oxo-1,3-benzoxathiol-5-yl instead of 3,5-dichlorophenyl.

Table 42

The compounds in Table 42 are of the general formula (1) where Ar is 1,3-benzodithiol-5-yl, n is 0, L is O, $R^1$ is methyl, and $R^2$ and $R^3$ have the values given in Table 1. Thus compound 1 of Table 42 is the same as compound 1 of Table 1 except that in compound 1 of Table 42 Ar is 1,3-benzodithiol-5-yl instead of 3,5-dichlorophenyl. Similarly, compounds 2 to 237 of Table 42 are the same as compounds 2 to 237 of Table 1, respectively, except that in the compounds of Table 42 Ar is 1,3-benzodithiol-5-yl instead of 3,5-dichlorophenyl.

Table 43

The compounds in Table 43 are of the general formula (1) where Ar is inden-5-yl, n is 0, L is O, $R^1$ is methyl, and $R^2$ and $R^3$ have the values given in Table 1. Thus compound 1 of Table 43 is the same as compound 1 of Table 1 except that in compound 1 of Table 43 Ar is inden-5-yl instead of 3,5-dichlorophenyl. Similarly, compounds 2 to 237 of Table 43 are the same as compounds 2 to 237 of Table 1, respectively, except that in the compounds of Table 43 Ar is inden-5-yl instead of 3,5-dichlorophenyl.

Table 44

The compounds in Table 44 are of the general formula (1) where Ar is benzofuran-5-yl, n is 0, L is O, $R^1$ is methyl, and $R^2$ and $R^3$ have the values given in Table 1. Thus compound 1 of Table 44 is the same as compound 1 of Table 1 except that in compound 1 of Table 44 Ar is benzofuran-5-yl instead of 3,5-dichlorophenyl. Similarly, compounds 2 to 237 of Table 44 are the same as compounds 2 to 237 of Table 1, respectively, except that in the compounds of Table 44 Ar is benzofuran-5-yl instead of 3,5-dichlorophenyl.

| Compound No. | $R^2$ | $R^3$ | |
|---|---|---|---|
| 12 | H | tert-$C_4H_9$ | oil |
| 189 | H | $C_6H_5$—$(CH_3)_2$C— | 111-113° C. |

Table 45

The compounds in Table 45 are of the general formula (1) where Ar is 2-phenylbenzofuran-5-yl, n is 0, L is O, $R^1$ is methyl, and $R^2$ and $R^3$ have the values given in Table 1. Thus compound 1 of Table 45 is the same as compound 1 of Table 1 except that in compound 1 of Table 45 Ar is 2-phenylbenzofuran-5-yl instead of 3,5-dichlorophenyl. Similarly, compounds 2 to 237 of Table 45 are the same as compounds 2 to 237 of Table 1, respectively, except that in the compounds of Table 45 Ar is 2-phenylbenzofuran-5-yl instead of 3,5-dichlorophenyl.

Table 46

The compounds in Table 46 are of the general formula (1) where Ar is 3-methylbenzo-furan-5-yl, n is 0, L is O, $R^1$ is methyl, and $R^2$ and $R^3$ have the values given in Table 1. Thus compound 1 of Table 46 is the same as compound 1 of Table 1 except that in compound 1 of Table 46 Ar is 3-methylbenzofuran-5-yl instead of 3,5-dichlorophenyl. Similarly, compounds 2 to 237 of Table 46 are the same as compounds 2 to 237 of Table 1, respectively, except that in the compounds of Table 46 Ar is 3-methylbenzofuran-5-yl instead of 3,5-dichlorophenyl.

Table 47

The compounds in Table 47 are of the general formula (1) where Ar is benzothien-5-yl of the formula (A), n is 0, L is O, $R^1$ is methyl, and $R^2$ and $R^3$ have the values given in Table 1.

Thus compound 1 of Table 47 is the same as compound 1 of Table 1 except that in compound 1 of Table 47 Ar is benzothien-5-yl instead of 3,5-dichlorophenyl. Similarly, compounds 2 to 237 of Table 47 are the same as compounds 2 to 237 of Table 1, respectively, except that in the compounds of Table 47 Ar is benzothien-5-yl instead of 3,5-dichlorophenyl.

| Compound No. | $R^2$ | $R^3$ | |
|---|---|---|---|
| 12 | H | tert-$C_4H_9$ | oil |

Table 48

The compounds in Table 48 are of the general formula (1) where Ar is 9H-fluoren-3-yl of the formula (A), n is 0, L is O, $R^1$ is methyl, and $R^2$ and $R^3$ have the values given in Table 1. Thus compound 1 of Table 48 is the same as compound 1 of Table 1 except that in compound 1 of Table 48 Ar is 9H-fluoren-3-yl instead of 3,5-dichlorophenyl. Similarly, compounds 2 to 237 of Table 48 are the same as compounds 2 to 237 of Table 1, respectively, except that in the compounds of Table 48 Ar is 9H-fluoren-3-yl instead of 3,5-dichlorophenyl.

Table 49

The compounds in Table 49 are of the general formula (1) where Ar is 9-oxo-9H-fluoren-3-yl of the formula (A), n is 0, L is O, $R^1$ is methyl, and $R^2$ and $R^3$ have the values given in Table 1. Thus compound 1 of Table 49 is the same as compound 1 of Table 1 except that in compound 1 of Table 49 Ar is 9-oxo-9H-fluoren-3-yl instead of 3,5-dichlorophenyl. Similarly, compounds 2 to 237 of Table 49 are the same as compounds 2 to 237 of Table 1, respectively, except that in the compounds of Table 49 Ar is 9-oxo-H-fluoren-3-yl instead of 3,5-dichlorophenyl.

Table 50

The compounds in Table 50 are of the general formula (1) where Ar is dibenzofuran-2-yl of the formula (A), n is 0, L is O, $R^1$ is methyl, and $R^2$ and $R^3$ have the values given in Table 1. Thus compound 1 of Table 50 is the same as compound 1 of Table 1 except that in compound 1 of Table 50 Ar is dibenzofuran-2-yl instead of 3,5-dichlorophenyl. Similarly, compounds 2 to 237 of Table 50 are the same as compounds 2 to 237 of Table 1, respectively, except that in the compounds of Table 50 Ar is dibenzofuran-2-yl instead of 3,5-dichlorophenyl.

Table 51

The compounds in Table 51 are of the general formula (1) where Ar is 7-methyldibenzofuran-2-yl of the formula (A), n is 0, L is O, $R^1$ is methyl, and $R^2$ and $R^3$ have the values given in Table 1. Thus compound 1 of Table 51 is the same as compound 1 of Table 1 except that in compound 1 of Table 51 Ar is 7-methyldibenzofuran-2-yl instead of 3,5-dichlorophenyl. Similarly, compounds 2 to 237 of Table 51 are the same as compounds 2 to 237 of Table 1, respectively, except that in the compounds of Table 51 Ar is 7-methyl-dibenzofuran-2-yl instead of 3,5-dichlorophenyl.

Table 52

The compounds in Table 52 are of the general formula (1) where Ar is 8-chlorodibenzofuran-2-yl of the formula (A), n is 0, L is O, $R^1$ is methyl, and $R^2$ and $R^3$ have the values given in Table 1. Thus compound 1 of Table 52 is the same as compound 1 of Table 1 except that in compound 1 of Table 52 Ar is 8-chlorodibenzofuran-2-yl instead of 3,5-dichlorophenyl. Similarly, compounds 2 to 237 of Table 52 are the same as compounds 2 to 237 of Table 1, respectively, except that in the compounds of Table 52 Ar is 8-chloro-dibenzofuran-2-yl instead of 3,5-dichlorophenyl.

Table 53

The compounds in Table 53 are of the general formula (1) where Ar is 9-chlorodibenzofuran-2-yl of the formula (A), n is 0, L is O, $R^1$ is methyl, and $R^2$ and $R^3$ have the values given in Table 1. Thus compound 1 of Table 53 is the same as compound 1 of Table 1 except that in compound 1 of Table 53 Ar is 9-chlorodibenzofuran-2-yl instead of 3,5-dichlorophenyl. Similarly, compounds 2 to 237 of Table 53 are the same as compounds 2 to 237 of Table 1, respectively, except that in the compounds of Table 53 Ar is 9-chlorodibenzofuran-2-yl instead of 3,5-dichlorophenyl.

Table 54

The compounds in Table 54 are of the general formula (1) where Ar is dibenzothien-2-yl of the formula (A), n is 0, L is O, $R^1$ is methyl, and $R^2$ and $R^3$ have the values given in Table 1. Thus compound 1 of Table 54 is the same as compound 1 of Table 1 except that in compound 1 of Table 54 Ar is dibenzothien-2-yl instead of 3,5-dichlorophenyl. Similarly, compounds 2 to 237 of Table 54 are the same as compounds 2 to 237 of Table 1, respectively, except that in the compounds of Table 54 Ar is dibenzothien-2-yl instead of 3,5-dichlorophenyl.

Table 55

The compounds in Table 55 are of the general formula (1) where Ar is 5,6,7,8-tetrahydronaphth-2-yl of the formula (A), n is 0, L is O, $R^1$ is methyl, and $R^2$ and $R^3$ have the values given in Table 1. Thus compound 1 of Table 55 is the same as compound 1 of Table 1 except that in compound 1 of Table 55

| Compound no. | $R^2$ | $R^3$ | |
|---|---|---|---|
| 232 | H | 1-benzyloxymethyl-cycloprop-1-yl | $[M + 1]^+$ 449 |
| 230 | H | $(CH_3)_2CH-CH_2(CH_3)C(CN)-$ | $[M + 1]^+$ 398 |
| 228 | H | $4-CH_3O-C_6H_4-CH_2CH_2(CH_3)C(CN)-$ | $[M + 2]^+$ 477 |
| 227 | H | $4-Cl-C_6H_4-CH_2(CH_3)C(CN)-$ | $[M + 1]^+$ 466 |

The preparation of 2-(dibenzofuranyl-2-oxy)-2-methylthio-N-(2-methylprop-2-yl)acetamide (Compound No. 12 of Table 50) is described in Example 12, page 93. $^1$H NMR characterisation of compound No.s 12, 35, 38, 52, 70, 84, 120, 122, 128, 133 and 189 of Table 50 is provided on pages 94 and 95.

Ar is 5,6,7,8-tetrahydronaphth-2-yl instead of 3,5-dichlorophenyl. Similarly, compounds 2 to 237 of Table 55 are the same as compounds 2 to 237 of Table 1, respectively, except that in the compounds of Table 55 Ar is 5,6,7,8-tetrahydronaphth-2-yl instead of 3,5-dichlorophenyl.

| Compound No. | $R^2$ | $R^3$ | |
|---|---|---|---|
| 12 | H | tert-$C_4H_9$ | oil |

Table 56

The compounds in Table 56 are of the general formula (1) where Ar is quinolin-6-yl, n is 0, L is O, $R^1$ is methyl, and $R^2$ and $R^3$ have the values given in Table 1. Thus compound 1 of Table 56 is the same as compound 1 of Table 1 except that in compound 1 of Table 56 Ar is quinolin-6-yl instead of 3,5-dichlorophenyl. Similarly, compounds 2 to 237 of Table 56 are the same as compounds 2 to 237 of Table 1, respectively, except that in the compounds of Table 56 Ar is quinolin-6-yl instead of 3,5-dichlorophenyl.

Table 57

The compounds in Table 57 are of the general formula (1) where Ar is 3-bromoquinolin-6-yl, n is 0, L is O, $R^1$ is methyl, and $R^2$ and $R^3$ have the values listed in Table 1. Thus compound 1 of Table 57 is the same as compound 1 of Table 1 except that in compound 1 of Table 57 Ar is 3-bromoquinolin-6-yl instead of 3,5-dichlorophenyl. Similarly, compounds 2 to 237 of Table 57 are the same as compounds 2 to 237 of Table 1, respectively, except that in the compounds of Table 57 Ar is 3-bromoquinolin-6-yl instead of 3,5-dichlorophenyl.

| Compound no. | $R^2$ | $R^3$ | | Mp/° C. |
|---|---|---|---|---|
| 68 | H | $C_2H_5OCH_2(CH_3)_2C$— | $[M + 2]^+$ 429 | 75-76.5 |
| 220 | H | $(H_2C=CHCH_2OCH_2)(CH_3)_2C$— | $[M + 2]^+$ 441 | 80-82 |
| 224 | H | $C_6H_5CH_2OCH_2(CH_3)_2C$— | $[M + 2]^+$ 491 | 90-91 |
| 16 | H | 2-methyl-but-2-yl | $[M + 2]^+$ 399 | 103-104 |
| 229 | H | 2-Cl—$C_6H_4$—$CH_2(CH_3)C(CN)$— | / | 138-140 |
| 227 | H | 4-Cl—$C_6H_4$—$CH_2(CH_3)C(CN)$— | / | 77-79 |
| 226 | H | 4-F—$C_6H_4$—$CH_2(CH_3)C(CN)$— | [M+] 488 | / |
| 230 | H | $(CH_3)_2CH$—$CH_2(CH_3)C(CN)$— | $[M + 2]^+$ 438 | / |
| 235 | H | 1-cyclopropyl-eth-1-yl | / | 106-108 |
| 236 | H | 2-fluoro-eth-1-yl | / | 104-106 |
| 237 | H | 2,2,2-trifluoro-1-methyl-eth-1-yl | / | 163-166 |

The preparation of Compound No. 48 of Table 57, 2-(3-bromoquinolinyl-6-oxy)-2-methylthio-N-(1-methoxy-3-methylbut-3-yl)acetamide is described in Example 7, page 85.

$^1$H NMR characterisation of compound No.s 4, 12, 24, 27, 35, 38, 40, 47, 48, 49, 50, 52, 60, 64, 65, 70, 84, 88, 89, 111, 120, 122, 124, 133, 150, 189 and 198 of Table 57 is provided on pages 86 to 89.

The preparation of compound Compound No. 82 of Table 57, 2-(methylthio)-2-(3-bromoquinolinyl-6-oxy)-N-E-(4-phenyl-2-methylpent-3-ene-2-yl)acetamide, is described in Example 9, page 91.

The preparation of compound No. 39 of Table 57, 2-(3-bromoquinolinyl-6-oxy)-2-(methylthio)-N-(1-hydroxy-2-methylprop-2-yl) acetamide, is described in Example 11, page 93 along with $^1$H NMR characterisation.

Table 58

The compounds in Table 58 are of the general formula (1) where Ar is 3-chloroquinolin-6-yl, n is 0, L is O, $R^1$ is methyl, and $R^2$ and $R^3$ have the values listed in Table 1. Thus compound 1 of Table 58 is the same as compound 1 of Table 1 except that in compound 1 of Table 58 Ar is 3-chloroquinolin-6-yl instead of 3,5-dichlorophenyl. Similarly, compounds 2 to 237 of Table 58 are the same as compounds 2 to 237 of Table 1, respectively, except that in the compounds of Table 58 Ar is 3-chloroquinolin-6-yl instead of 3,5-dichlorophenyl.

The preparation of Compound No. 12 of Table 58, 2-(3-chloroquinolinyl-6-oxy)-2-methylthio-N-(2-methylprop-2-yl)acetamide is described in Example 5, page 80. $^1$H NMR characterisation of compound No.s 12, 35, 38, 52, 64, 70, 84, 120, 122, 124, 128, 133, 150, 189, and of Table 58 is provided on pages 82 to 83.

Table 58A

The compounds in Table 58A are of the general formula (1) where Ar is 3-iodoquinolin-6-yl, n is 0, L is O, $R^1$ is methyl, and $R^2$ and $R^3$ have the values listed in Table 1. Thus compound 1 of Table 58A is the same as compound 1 of Table 1 except that in compound 1 of Table 58A Ar is 3-iodoquinolin-6-yl instead of 3,5-dichlorophenyl. Similarly, compounds 2 to 237 of Table 58A are the same as compounds 2 to 237 of Table 1, respectively, except that in the compounds of Table 58A Ar is 3-iodoquinolin-6-yl instead of 3,5-dichlorophenyl.

| Compound No. | $R^2$ | $R^3$ | | Mp/° C. |
|---|---|---|---|---|
| 12 | H | tert-$C_4H_9$ | $[M + 1]^+$ 431 | 151-153 |
| 52 | H | $CH_3OCH_2(CH_3)C(CN)$— | $[M + 1]^+$ 472 | / |

Table 59

The compounds in Table 59 are of the general formula (1) where Ar is 3-fluoroquinolin-6-yl, n is 0, L is O, $R^1$ is methyl, and $R^2$ and $R^3$ have the values listed in Table 1. Thus compound 1 of Table 59 is the same as compound 1 of Table 1 except that in compound 1 of Table 59 Ar is 3-fluoroquinolin-6-yl instead of 3,5-dichlorophenyl. Similarly, compounds 2 to 237 of Table 59 are the same as compounds 2 to 237 of Table 1, respectively, except that in the compounds of Table 59 Ar is 3-fluoroquinolin-6-yl instead of 3,5-dichlorophenyl.

The preparation of 2-(3-fluoroquinolinyl-6-oxy)-2-methylthio-N-(2-methylprop-2-yl)acetamide (Compound No. 12 of Table 59) is described in Example 8, page 89-91 along with $^1$H NMR characterisation for compounds 12 and 52.

Table 60

The compounds in Table 60 are of the general formula (1) where Ar is 8-bromoquinolin-6-yl, n is 0, L is O, $R^1$ is methyl, and $R^2$ and $R^3$ have the values listed in Table 1. Thus compound 1 of Table 60 is the same as compound 1 of Table 1 except that in compound 1 of Table 60 Ar is 8-bromoquinolin-6-yl instead of 3,5-dichlorophenyl. Similarly, compounds 2 to 237 of Table 60 are the same as compounds 2 to 237 of Table 1, respectively, except that in the compounds of Table 60 Ar is 8-bromoquinolin-6-yl instead of 3,5-dichlorophenyl.

| Compound No. | $R^2$ | $R^3$ | Mp/° C. |
|---|---|---|---|
| 12 | H | tert-$C_4H_9$ | 122-125 |
| 52 | H | $CH_3OCH_2(CH_3)C(CN)$— | 139-141 |

Table 60A

The compounds in Table 60A are of the general formula (1) where Ar is 8-chloroquinolin-6-yl, n is 0, L is O, $R^1$ is methyl, and $R^2$ and $R^3$ have the values listed in Table 1. Thus compound 1 of Table 60A is the same as compound 1 of Table 1 except that in compound 1 of Table 60A Ar is 8-chloroquinolin-6-yl instead of 3,5-dichlorophenyl. Similarly, compounds 2 to 237 of Table 60A are the same as compounds 2 to 237 of Table 1, respectively, except that in the compounds of Table 60A Ar is 8-chloroquinolin-6-yl instead of 3,5-dichlorophenyl.

Table 60B

The compounds in Table 60B are of the general formula (1) where Ar is 8-fluoroquinolin-6-yl, n is 0, L is O, $R^1$ is methyl, and $R^2$ and $R^3$ have the values listed in Table 1. Thus compound 1 of Table 60B is the same as compound 1 of Table 1 except that in compound 1 of Table 60B Ar is 8-fluoroquinolin-6-yl instead of 3,5-dichlorophenyl. Similarly, compounds 2 to 237 of Table 60B are the same as compounds 2 to 237 of Table 1, respectively, except that in the compounds of Table 60B Ar is 8-fluoroquinolin-6-yl instead of 3,5-dichlorophenyl.

Table 60C

The compounds in Table 60C are of the general formula (1) where Ar is 8-iodoquinolin-6-yl, n is 0, L is O, $R^1$ is methyl, and $R^2$ and $R^3$ have the values listed in Table 1. Thus compound 1 of Table 60C is the same as compound 1 of Table 1 except that in compound 1 of Table 60C Ar is 8-iodoquinolin-6-yl instead of 3,5-dichlorophenyl. Similarly, compounds 2 to 237 of Table 60C are the same as compounds 2 to 237 of Table 1, respectively, except that in the compounds of Table 60C Ar is 8-iodoquinolin-6-yl instead of 3,5-dichlorophenyl.

Table 61

The compounds in Table 61 are of the general formula (1) where Ar is 3,8-dibromoquinolin-6-yl, n is 0, L is O, $R^1$ is methyl, and $R^2$ and $R^3$ have the values listed in Table 1. Thus compound 1 of Table 61 is the same as compound 1 of Table 1 except that in compound 1 of Table 61 Ar is 3,8-dibromoquinolin-6-yl instead of 3,5-dichlorophenyl. Similarly, compounds 2 to 237 of Table 61 are the same as compounds 2 to 237 of Table 1, respectively, except that in the compounds of Table 61 Ar is 3,8-dibromoquinolin-6-yl instead of 3,5-dichlorophenyl.

| Compound No. | $R^2$ | $R^3$ | Mp/° C. |
|---|---|---|---|
| 16 | H | 2-methyl-but-2-yl | 132-133 |
| 52 | H | $CH_3OCH_2(CH_3)C(CN)$— | 139-142 |
| 50 | H | $CH_3S$—$CH_2(CH_3)_2C$— | 141-143 |
| 68 | H | $C_2H_5OCH_2(CH_3)_2C$— | 128.5-131.5 |
| 220 | H | $(H_2C$=$CHCH_2OCH_2)(CH_3)_2C$— | 97.5-101 |
| 224 | H | $C_6H_5CH_2OCH_2(CH_3)_2C$— | 126-127 |

The preparation of 2-(3,8-dibromoquinolinyl-6-oxy)-2-methylthio-N-(2-thienylmethyl)acetamide (Compound No. 124 of Table 61) is described in Example 6, page 83. $^1$H NMR characterisation of compound No.s 12, 38, 52, 150 and 211 of Table 61 is provided on pages 85 and 85.

Table 62

The compounds in Table 62 are of the general formula (1) where Ar is 3-bromo-8-chloroquinolin-6-yl, n is 0, L is O, $R^1$ is methyl, and $R^2$ and $R^3$ have the values listed in Table 1. Thus compound 1 of Table 62 is the same as compound 1 of Table 1 except that in compound 1 of Table 62 Ar is 3-bromo-8-chloroquinolin-6-yl instead of 3,5-dichlorophenyl. Similarly, compounds 2 to 237 of Table 62 are the same as compounds 2 to 237 of Table 1, respectively, except that in the compounds of Table 62 Ar is 3-bromo-8-chloroquinolin-6-yl instead of 3,5-dichlorophenyl.

| Compound No. | $R^2$ | $R^3$ |  | Mp/° C. |
|---|---|---|---|---|
| 47 | H | $CH_3O$—$CH_2(CH_3)_2C$— | [M + 1]$^+$ 449 | 125.5-127 |
| 12 | H | tert-$C_4H_9$ | [M + 1]$^+$ 419 | 160-161 |
| 16 | H | 2-methyl-but-2-yl | [M + 1]$^+$ 433 | / |
| 50 | H | $CH_3S$—$CH_2(CH_3)_2C$— | [M + 1]$^+$ 465 | 148-149 |
| 68 | H | $C_2H_5OCH_2(CH_3)_2C$— | [M + 1]$^+$ 463 | 143-146 |
| 220 | H | $(H_2C$=$CHCH_2OCH_2)(CH_3)_2C$— | [M + 1]$^+$ 475 | 104-106 |
| 224 | H | $C_6H_5CH_2OCH_2(CH_3)_2C$— | [M + 1]$^+$ 525 | 118-121 |

Table 62A

The compounds in Table 62A are of the general formula (1) where Ar is 3-bromo-8-iodoquinolin-6-yl, n is 0, L is O, $R^1$ is methyl, and $R^2$ and $R^3$ have the values listed in Table 1. Thus compound 1 of Table 62A is the same as compound 1 of Table 1 except that in compound 1 of Table 62A Ar is 3-bromo-8-iodoquinolin-6-yl instead of 3,5-dichlorophenyl. Similarly, compounds 2 to 237 of Table 62A are the same as compounds 2 to 237 of Table 1, respectively, except that in the compounds of Table 62A Ar is 3-bromo-8-iodoquinolin-6-yl instead of 3,5-dichlorophenyl.

| Compound no. | $R^2$ | $R^3$ | Mp/° C. |
|---|---|---|---|
| 12 | H | tert-$C_4H_9$ | 171-172 |

Table 62B

The compounds in Table 62B are of the general formula (1) where Ar is 3-bromo-8-fluoroquinolin-6-yl, n is 0, L is O, $R^1$ is methyl, and $R^2$ and $R^3$ have the values listed in Table 1. Thus compound 1 of Table 62B is the same as compound 1 of Table 1 except that in compound 1 of Table 62B Ar is 3-bromo-8-fluoroquinolin-6-yl instead of 3,5-dichlorophenyl. Similarly, compounds 2 to 237 of Table 62B are the same as compounds 2 to 237 of Table 1, respectively, except that in the compounds of Table 62B Ar is 3-bromo-8-fluoroquinolin-6-yl instead of 3,5-dichlorophenyl.

| Compound No. | R² | R³ | Mp/° C. |
|---|---|---|---|
| 12 | H | tert-C₄H₉ | 158.5-159.5° C. |
| 52 | H | CH₃OCH₂(CH₃)C(CN)— | gum |
| 230 | H | (CH₃)₂CH—CH₂(CH₃)C(CN)— | gum |

Table 62C

The compounds in Table 62C are of the general formula (1) where Ar is 3-chloro-8-bromoquinolin-6-yl, n is 0, L is O, $R^1$ is methyl, and $R^2$ and $R^3$ have the values listed in Table 1. Thus compound 1 of Table 62C is the same as compound 1 of Table 1 except that in compound 1 of Table 62C Ar is 3-chloro-8-bromoquinolin-6-yl instead of 3,5-dichlorophenyl. Similarly, compounds 2 to 237 of Table 62C are the same as compounds 2 to 237 of Table 1, respectively, except that in the compounds of Table 62C Ar is 3-chloro-8-bromoquinolin-6-yl instead of 3,5-dichlorophenyl.

Table 62D

The compounds in Table 62D are of the general formula (1) where Ar is 3,8-dichloroquinolin-6-yl, n is 0, L is O, $R^1$ is methyl, and $R^2$ and $R^3$ have the values listed in Table 1. Thus compound 1 of Table 62D is the same as compound 1 of Table 1 except that in compound 1 of Table 62D Ar is 3,8-dichloroquinolin-6-yl instead of 3,5-dichlorophenyl. Similarly, compounds 2 to 237 of Table 62D are the same as compounds 2 to 237 of Table 1, respectively, except that in the compounds of Table 62D Ar is 3,8-dichloro-quinolin-6-yl instead of 3,5-dichlorophenyl.

Table 62E

The compounds in Table 62E are of the general formula (1) where Ar is 3-chloro-8-iodoquinolin-6-yl, n is 0, L is O, $R^1$ is methyl, and $R^2$ and $R^3$ have the values listed in Table 1. Thus compound 1 of Table 62E is the same as compound 1 of Table 1 except that in compound 1 of Table 62E Ar is 3-chloro-8-iodoquinolin-6-yl instead of 3,5-dichlorophenyl. Similarly, compounds 2 to 237 of Table 62E are the same as compounds 2 to 237 of Table 1, respectively, except that in the compounds of Table 62E Ar is 3-chloro-8-iodoquinolin-6-yl instead of 3,5-dichlorophenyl.

Table 62F

The compounds in Table 62F are of the general formula (1) where Ar is 3-chloro-8-fluoroquinolin-6-yl, n is 0, L is O, $R^1$ is methyl, and $R^2$ and $R^3$ have the values listed in Table 1. Thus compound 1 of Table 62F is the same as compound 1 of Table 1 except that in compound 1 of Table 62F Ar is 3-chloro-8-fluoroquinolin-6-yl instead of 3,5-dichlorophenyl. Similarly, compounds 2 to 237 of Table 62F are the same as compounds 2 to 237 of Table 1, respectively, except that in the compounds of Table 62F Ar is 3-chloro-8-fluoroquinolin-6-yl instead of 3,5-dichlorophenyl.

Table 62G

The compounds in Table 62G are of the general formula (1) where Ar is 3-fluoro-8-bromoquinolin-6-yl, n is 0, L is O, $R^1$ is methyl, and $R^2$ and $R^3$ have the values listed in Table 1. Thus compound 1 of Table 62G is the same as compound 1 of Table 1 except that in compound 1 of Table 62G Ar is 3-fluoro-8-bromoquinolin-6-yl instead of 3,5-dichlorophenyl. Similarly, compounds 2 to 237 of Table 62G are the same as compounds 2 to 237 of Table 1, respectively, except that in the compounds of Table 62G Ar is 3-fluoro-8-bromoquinolin-6-yl instead of 3,5-dichlorophenyl.

Table 62H

The compounds in Table 62H are of the general formula (1) where Ar is 3-fluoro-8-chloro-quinolin-6-yl, n is 0, L is O, $R^1$ is methyl, and $R^2$ and $R^3$ have the values listed in Table 1. Thus compound 1 of Table 62H is the same as compound 1 of Table 1 except that in compound 1 of Table 62H Ar is 3-fluoro-8-chloro-quinolin-6-yl instead of 3,5-dichlorophenyl. Similarly, compounds 2 to 237 of Table 62H are the same as compounds 2 to 237 of Table 1, respectively, except that in the compounds of Table 62H Ar is 3-fluoro-8-chloro-quinolin-6-yl instead of 3,5-dichlorophenyl.

Table 62I

The compounds in Table 62I are of the general formula (1) where Ar is 3-fluoro-8-iodoquinolin-6-yl, n is 0, L is O, $R^1$ is methyl, and $R^2$ and $R^3$ have the values listed in Table 1. Thus compound 1 of Table 62I is the same as compound 1 of Table 1 except that in compound 1 of Table 62I Ar is 3-fluoro-8-iodoquinolin-6-yl instead of 3,5-dichlorophenyl. Similarly, compounds 2 to 237 of Table 62I are the same as compounds 2 to 237 of Table 1, respectively, except that in the compounds of Table 62I Ar is 3-fluoro-8-iodoquinolin-6-yl instead of 3,5-dichlorophenyl.

Table 62J

The compounds in Table 62J are of the general formula (1) where Ar is 3,8-difluoroquinolin-6-yl, n is 0, L is O, $R^1$ is methyl, and $R^2$ and $R^3$ have the values listed in Table 1. Thus compound 1 of Table 62J is the same as compound 1 of Table 1 except that in compound 1 of Table 62J Ar is 3-chloro-8-fluoroquinolin-6-yl instead of 3,5-dichlorophenyl. Similarly, compounds 2 to 237 of Table 62J are the same as compounds 2 to 237 of Table 1, respectively, except that in the compounds of Table 62J Ar is 3-chloro-8-fluoroquinolin-6-yl instead of 3,5-dichlorophenyl.

Table 62K

The compounds in Table 62K are of the general formula (1) where Ar is 3-iodo-8-bromo-quinolin-6-yl, n is 0, L is O, $R^1$ is methyl, and $R^2$ and $R^3$ have the values listed in Table 1. Thus compound 1 of Table 62K is the same as compound 1 of Table 1 except that in compound 1 of Table 62K Ar is 3-iodo-8-bromoquinolin-6-yl instead of 3,5-dichlorophenyl. Similarly, compounds 2 to 237 of Table 62K are the same as compounds 2 to 237 of Table 1, respectively, except that in the compounds of Table 62K Ar is 3-iodo-8-bromoquinolin-6-yl instead of 3,5-dichlorophenyl.

Table 62L

The compounds in Table 62L are of the general formula (1) where Ar is 3-iodo-8-chloro-quinolin-6-yl, n is 0, L is O, $R^1$ is methyl, and $R^2$ and $R^3$ have the values listed in Table 1. Thus compound 1 of Table 62L is the same as compound 1 of Table 1 except that in compound 1 of Table 62L Ar is 3-iodo-8-chloro-quinolin-6-yl instead of 3,5-dichlorophenyl. Similarly, compounds 2 to 237 of Table 62L are the same as compounds 2 to 237 of Table 1, respectively, except that in the compounds of Table 62L Ar is 3-iodo-8-chloro-quinolin-6-yl instead of 3,5-dichlorophenyl.

Table 62M

The compounds in Table 62M are of the general formula (1) where Ar is 3,8-di-iodoquinolin-6-yl, n is 0, L is O, $R^1$ is methyl, and $R^2$ and $R^3$ have the values listed in Table 1. Thus compound 1 of Table 62M is the same as compound 1 of Table 1 except that in compound 1 of Table 62M Ar is 3,8-di-iodoquinolin-6-yl instead of 3,5-dichlorophenyl. Similarly, compounds 2 to 237 of Table 62M are the same as compounds 2 to 237 of Table 1, respectively, except that in the compounds of Table 62M Ar is 3,8-di-iodoquinolin-6-yl instead of 3,5-dichlorophenyl.

Table 62N

The compounds in Table 62N are of the general formula (1) where Ar is 3-iodo-8-fluoroquinolin-6-yl, n is 0, L is O, $R^1$ is methyl, and $R^2$ and $R^3$ have the values listed in Table 1. Thus compound 1 of Table 62N is the same as compound 1 of Table 1 except that in compound 1 of Table 62N Ar is 3-chloro-8-fluoroquinolin-6-yl instead of 3,5-dichlorophenyl. Similarly, compounds 2 to 237 of Table 62N are the same as compounds 2 to 237 of Table 1, respectively, except that in the compounds of Table 62N Ar is 3-chloro-8-fluoroquinolin-6-yl instead of 3,5-dichlorophenyl.

Table 62P

The compounds in Table 62P are of the general formula (1) where Ar is 8-methylquinolin-6-yl, n is 0, L is O, $R^1$ is methyl, and $R^2$ and $R^3$ have the values listed in Table 1. Thus compound 1 of Table 62P is the same as compound 1 of Table 1 except that in compound 1 of Table 62P Ar is 8-methylquinolin-6-yl instead of 3,5-dichlorophenyl. Similarly, compounds 2 to 237 of Table 62P are the same as compounds 2 to 237 of Table 1, respectively, except that in the compounds of Table 62P Ar is 8-methylquinolin-6-yl instead of 3,5-dichlorophenyl.

Table 63

The compounds in Table 63 are of the general formula (1) where Ar is quinazolin-6-yl, n is 0, L is O, $R^1$ is methyl, and $R^2$ and $R^3$ have the values listed in Table 1. Thus compound 1 of Table 63 is the same as compound 1 of Table 1 except that in compound 1 of Table 63 Ar is quinazolin-6-yl instead of 3,5-dichlorophenyl. Similarly, compounds 2 to 237 of Table 63 are the same as compounds 2 to 237 of Table 1, respectively, except that in the compounds of Table 63 Ar is quinazolin-6-yl instead of 3,5-dichlorophenyl.

Table 64

The compounds in Table 64 are of the general formula (1) where Ar is isoquinolin-7-yl, n is 0, L is O, $R^1$ is methyl, and $R^2$ and $R^3$ have the values listed in Table 1. Thus compound 1 of Table 64 is the same as compound 1 of Table 1 except that in compound 1 of Table 64 Ar is isoquinolin-7-yl instead of 3,5-dichlorophenyl. Similarly, compounds 2 to 237 of Table 64 are the same as compounds 2 to 237 of Table 1, respectively, except that in the compounds of Table 64 Ar is isoquinolin-7-yl instead of 3,5-dichlorophenyl.

Table 65

The compounds in Table 65 are of the general formula (1) where Ar is 3-phenylquinolin-6-yl, n is 0, L is O, $R^1$ is methyl, and $R^2$ and $R^3$ have the values given in Table 1. Thus compound 1 of Table 65 is the same as compound 1 of Table 1 except that in compound 1 of Table 65 Ar is 3-phenylquinolin-6-yl instead of 3,5-dichlorophenyl. Similarly, compounds 2 to 237 of Table 65 are the same as compounds 2 to 237 of Table 1, respectively, except that in the compounds of Table 65 Ar is 3-phenylquinolin-6-yl instead of 3,5-dichlorophenyl.

Mp and $^1$H NMR characterisation of compound No. 12 of Table 65 is provided on page 93.

Table 66

The compounds in Table 66 are of the general formula (1) where Ar is 3-benzylquinolin-6-yl, n is 0, L is O, $R^1$ is methyl, and $R^2$ and $R^3$ have the values given in Table 1. Thus compound 1 of Table 66 is the same as compound 1 of Table 1 except that in compound 1 of Table 66 Ar is 3-benzylquinolin-6-yl instead of 3,5-dichlorophenyl. Similarly, compounds 2 to 237 of Table 66 are the same as compounds 2 to 237 of Table 1, respectively, except that in the compounds of Table 66 Ar is 3-benzylquinolin-6-yl instead of 3,5-dichlorophenyl.

Table 67

The compounds in Table 67 are of the general formula (1) where Ar is 7-bromo-naphth-2-yl, n is 0, L is O, $R^1$ is methyl, and $R^2$ and $R^3$ have the values given in Table 1. Thus compound 1 of Table 67 is the same as compound 1 of Table 1 except that in compound 1 of Table 67 Ar is 7-bromo-naphth-2-yl instead of 3,5-dichlorophenyl. Similarly, compounds 2 to 237 of Table 67 are the same as compounds 2 to 237 of Table 1, respectively, except that in the compounds of Table 67 Ar is 7-bromo-naphth-2-yl instead of 3,5-dichlorophenyl.

Table 68

The compounds in Table 68 are of the general formula (1) where Ar is 3-pyrid-4-yl-quinolin-6-yl, n is 0, L is O, $R^1$ is methyl, and $R^2$ and $R^3$ have the values given in Table 1. Thus compound 1 of Table 68 is the same as compound 1 of Table 1 except that in compound 1 of Table 68 Ar is 3-pyrid-4-ylquinolin-6-yl instead of 3,5-dichlorophenyl. Similarly, compounds 2 to 237 of Table 68 are the same as compounds 2 to 237 of Table 1, respectively, except that in the compounds of Table 68 Ar is 3-pyrid-4-ylquinolin-6-yl instead of 3,5-dichlorophenyl.

The preparation of compound No. 12 of Table 68, 2-(methylthio)-2-(3-[4 pyridyl]-quinolinyl-6-oxy)-N-(2-methylprop-2-yl) acetamide, is described in Example 10, page 92.

Table 69

The compounds in Table 69 are of the general formula (1) where Ar is isoquinolin-6-yl, n is 0, L is O, $R^1$ is methyl, and $R^2$ and $R^3$ have the values given in Table 1. Thus compound 1 of Table 69 is the same as compound 1 of Table 1 except that in compound 1 of Table 69 Ar is isoquinolin-6-yl instead of 3,5-dichlorophenyl. Similarly, compounds 2 to 237 of Table 69 are the same as compounds 2 to 237 of Table 1, respectively, except that in the compounds of Table 69 Ar is isoquinolin-6-yl instead of 3,5-dichlorophenyl.

Table 70

The compounds in Table 70 are of the general formula (1) where Ar is 5-chloropyrid-3-yl, n is 0, L is O, $R^1$ is methyl, and $R^2$ and $R^3$ have the values given in Table 1. Thus compound 1 of Table 70 is the same as compound 1 of Table 1 except that in compound 1 of Table 70 Ar is 5-chloropyrid-3-yl instead of 3,5-dichlorophenyl. Similarly, compounds 2 to 237 of Table 70 are the same as compounds 2 to 237 of Table 1, respectively, except that in the compounds of Table 70 Ar is 5-chloropyrid-3-yl instead of 3,5-dichlorophenyl.

The preparation of compound No. 12 of Table 70, 2-(5-chloropyridyl-3-oxy)-2-(methylthio)-N-(2-methylprop-2-yl) acetamide, is described in Example 3, page 77.

$^1$H NMR characterisation of compound numbers 12, 50 and 72 of Table 70 is provided on page 78.

Table 71

The compounds in Table 71 are of the general formula (1) where Ar is 5-bromopyrid-3-yl, n is 0, L is O, $R^1$ is methyl, and $R^2$ and $R^3$ have the values listed in Table 1. Thus compound 1 of Table 71 is the same as compound 1 of Table 1 except that in compound 1 of Table 71 Ar is 5-bromopyrid-3-yl instead of 3,5-dichlorophenyl. Similarly, compounds 2 to 237 of Table 71 are the same as compounds 2 to 237 of Table 1, respectively, except that in the compounds of Table 71 Ar is 5-bromopyrid-3-yl instead of 3,5-dichlorophenyl.

Table 72

The compounds in Table 72 are of the general formula (1) where Ar is 3-bromo-8-methylquinolin-6-yl, n is 0, L is O, $R^1$ is methyl, and $R^2$ and $R^3$ have the values listed in Table 1. Thus compound 1 of Table 72 is the same as compound 1 of Table 1 except that in compound 1 of Table 72 Ar is 3-bromo-8-methylquinolin-6-yl instead of 3,5-dichlorophenyl. Similarly, compounds 2 to 237 of Table 72 are the same as compounds 2 to 237 of Table 1, respectively, except that in the compounds of Table 72 Ar is 3-bromo-8-methylquinolin-6-yl instead of 3,5-dichlorophenyl.

| Compound No. | $R^2$ | $R^3$ | | Mp/°C. |
|---|---|---|---|---|
| 12 | H | tert-$C_4H_9$ | $[M + 2]^+$ 399 | 146-147 |
| 16 | H | 2-methyl-but-2-yl | $[M + 2]^+$ 413 | 129-132 |
| 47 | H | $CH_3O$—$CH_2(CH_3)_2C$— | $[M + 2]^+$ 429 | 127-128.5 |
| 50 | H | $CH_3S$—$CH_2(CH_3)_2C$— | $[M + 2]^+$ 445 | 130-131 |
| 52 | H | $CH_3OCH_2(CH_3)C(CN)$— | $[M + 2]^+$ 440 | 116-118 |
| 68 | H | $C_2H_5OCH_2(CH_3)_2C$— | $[M + 2]^+$ 443 | / |
| 220 | H | $(H_2C$=$CHCH_2OCH_2)(CH_3)_2C$— | $[M + 2]^+$ 455 | / |
| 224 | H | $C_6H_5CH_2OCH_2(CH_3)_2C$— | $[M + 2]^+$ 505 | 112-113 |

Table 72A

The compounds in Table 72A are of the general formula (1) where Ar is 3-iodo-8-methylquinolin-6-yl, n is 0, L is O, $R^1$ is methyl, and $R^2$ and $R^3$ have the values listed in Table 1. Thus compound 1 of Table 72A is the same as compound 1 of Table 1 except that in compound 1 of Table 72A Ar is 3-iodo-8-methylquinolin-6-yl instead of 3,5-dichlorophenyl. Similarly, compounds 2 to 237 of Table 72A are the same as compounds 2 to 237 of Table 1, respectively, except that in the compounds of Table 72A Ar is 3-iodo-8-methylquinolin-6-yl instead of 3,5-dichlorophenyl.

| Compound No. | $R^2$ | $R^3$ | Mp/°C. |
|---|---|---|---|
| 12 | H | tert-$C_4H_9$ | 148-150 |
| 52 | H | $CH_3OCH_2(CH_3)C(CN)$— | 57-59 |

Table 72B

The compounds in Table 72B are of the general formula (1) where Ar is 3-chloro-8-methylquinolin-6-yl, n is 0, L is O, $R^1$ is methyl, and $R^2$ and $R^3$ have the values listed in Table 1. Thus compound 1 of Table 72B is the same as compound 1 of Table 1 except that in compound 1 of Table 72A Ar is 3-chloro-8-methylquinolin-6-yl instead of 3,5-dichlorophenyl. Similarly, compounds 2 to 237 of Table 72B are the same as compounds 2 to 237 of Table 1, respectively, except that in the compounds of Table 72B Ar is 3-chloro-8-methylquinolin-6-yl instead of 3,5-dichlorophenyl.

Table 72C

The compounds in Table 72C are of the general formula (1) where Ar is 3-fluoro-8-methylquinolin-6-yl, n is 0, L is O, $R^1$ is methyl, and $R^2$ and $R^3$ have the values listed in Table 1. Thus compound 1 of Table 72C is the same as compound 1 of Table 1 except that in compound 1 of Table 72C Ar is 3-fluoro-8-methylquinolin-6-yl instead of 3,5-dichlorophenyl. Similarly, compounds 2 to 237 of Table 72C are the same as compounds 2 to 237 of Table 1, respectively, except that in the compounds of Table 72C Ar is 3-fluoro-8-methylquinolin-6-yl instead of 3,5-dichlorophenyl.

Table 73

The compounds in Table 73 are of the general formula (1) where Ar is 5,6-dichloropyrid-3-yl, n is 0, L is O, $R^1$ is methyl, and $R^2$ and $R^3$ have the values listed in Table 1. Thus compound 1 of Table 73 is the same as compound 1 of Table 1 except that in compound 1 of Table 73 Ar is 5,6-dichloropyrid-3-yl instead of 3,5-dichlorophenyl. Similarly, compounds 2 to 237 of Table 73 are the same as compounds 2 to 237 of Table 1, respectively, except that in the compounds of Table 73 Ar is 5,6-dichloropyrid-3-yl instead of 3,5-dichlorophenyl.

Table 74

The compounds in Table 74 are of the general formula (1) where Ar is 5-cyanopyrid-3-yl, n is 0, L is O, $R^1$ is methyl, and $R^2$ and $R^3$ have the values listed in Table 1. Thus compound 1 of Table 74 is the same as compound 1 of Table 1 except that in compound 1 of Table 74 Ar is 5-cyanopyrid-3-yl instead of 3,5-dichlorophenyl. Similarly, compounds 2 to 237 of Table 74 are the same as compounds 2 to 237 of Table 1, respectively, except that in the compounds of Table 74 Ar is 5-cyanopyrid-3-yl instead of 3,5-dichlorophenyl.

Table 75

The compounds in Table 75 are of the general formula (1) where Ar is 5-ethynylpyrid-3-yl, n is 0, L is O, $R^1$ is methyl, and $R^2$ and $R^3$ have the values listed in Table 1. Thus compound 1 of Table 75 is the same as compound 1 of Table 1 except that in compound 1 of Table 75 Ar is 5-ethynylpyrid-3-yl instead of 3,5-dichlorophenyl. Similarly, compounds 2 to 237 of Table 75 are the same as compounds 2 to 237 of Table 1, respectively, except that in the compounds of Table 75 Ar is 5-ethynylpyrid-3-yl instead of 3,5-dichlorophenyl.

Table 76

The compounds in Table 76 are of the general formula (1) where Ar is 5-ethenylpyrid-3-yl, n is 0, L is O, $R^1$ is methyl, and $R^2$ and $R^3$ have the values listed in Table 1. Thus compound 1 of Table 76 is the same as compound 1 of Table 1 except that in compound 1 of Table 76 Ar is 5-ethynylpyrid-3-yl instead of 3,5-dichlorophenyl. Similarly, compounds 2 to 237 of Table 76 are the same as compounds 2 to 237 of Table 1, respectively, except that in the compounds of Table 76 Ar is 5-ethynylpyrid-3-yl instead of 3,5-dichlorophenyl.

Table 77

The compounds in Table 77 are of the general formula (1) where Ar is a 2,6-dichloro-pyrid-4-yl, n is 0, L is O, $R^1$ is methyl, and $R^2$ and $R^3$ have the values given in Table 1. Thus compound 1 of Table 77 is the same as compound 1 of Table 1 except that in compound 1 of Table 77 Ar is 2,6-dichloro-pyrid-4-yl instead of 3,5-dichlorophenyl. Similarly, compounds 2 to 237 of Table 77 are the same as compounds 2 to 237 of Table 1, respectively, except that in the compounds of Table 77 Ar is 2,6-dichloro-pyrid-4-yl instead of 3,5-dichlorophenyl.

Table 78

The compounds in Table 78 are of the general formula (1) where Ar is benzothiazol-6-yl, n is 0, L is O, $R^1$ is methyl, and $R^2$ and $R^3$ have the values given in Table 1. Thus compound 1 of Table 78 is the same as compound 1 of Table 1 except that in compound 1 of Table 78 Ar is benzothiazol-6-yl instead of 3,5-dichlorophenyl. Similarly, compounds 2 to 237 of Table 78 are the same as compounds 2 to 237 of Table 1, respectively, except that in the compounds of Table 78 Ar is benzothiazol-6-yl instead of 3,5-dichlorophenyl.

The preparation of 2-(benzothiazolyl-6-oxy)-2-(methylthio)-N-(2-methylprop-2-yl)acetamide (Compound No. 12 of Table 78), is described in Example 4, page 78 along with $^1$H NMR characterisation for compounds 12, 35, 52, 70, 133, 189 on pages 79 to 80.

Table 79

The compounds in Table 79 are of the general formula (1) where Ar is benzothiazol-6-yl, n is 0, L is O, $R^1$ is ethyl, and $R^2$ and $R^3$ have the values listed in Table 1. Thus compound 1 of Table 79 is the same as compound 1 of Table 78 except that in compound 1 of Table 79 $R^1$ is ethyl instead of methyl. Similarly, compounds 2 to 237 of Table 79 are the same as compounds 2 to 237 of Table 78, respectively, except that in the compounds of Table 79 $R^1$ is ethyl instead of methyl.

Table 80

The compounds in Table 80 are of the general formula (1) where Ar is 2-bromo-benzothiazol-6-yl, n is 0, L is O, $R^1$ is methyl, and $R^2$ and $R^3$ have the values given in Table 1. Thus compound 1 of Table 80 is the same as compound 1 of Table 1 except that in compound 1 of Table 80 Ar is 2-bromobenzothiazol-6-yl instead of 3,5-dichlorophenyl. Similarly, compounds 2 to 237 of Table 80 are the same as compounds 2 to 237 of Table 1, respectively, except that in the compounds of Table 80 Ar is 2-bromo-benzothiazol-6-yl instead of 3,5-dichlorophenyl.

Table 81

The compounds in Table 81 are of the general formula (1) where Ar is 2-chloro-benzothiazol-6-yl, n is 0, L is O, $R^1$ is methyl, and $R^2$ and $R^3$ have the values given in Table 1. Thus compound 1 of Table 81 is the same as compound 1 of Table 1 except that in compound 1 of Table 81 Ar is 2-chlorobenzothiazol-6-yl instead of 3,5-dichlorophenyl. Similarly, compounds 2 to 237 of Table 81 are the same as compounds 2 to 237 of Table 1, respectively, except that in the compounds of Table 81 Ar is 2-chloro-benzothiazol-6-yl instead of 3,5-dichlorophenyl.

Table 82

The compounds in Table 82 are of the general formula (1) where Ar is 2-methylamino-benzothiazol-6-yl, n is 0, L is O, $R^1$ is methyl, and $R^2$ and $R^3$ have the values given in Table 1. Thus compound 1 of Table 82 is the same as compound 1 of Table 1 except that in compound 1 of Table 82 Ar is 2-methylaminobenzothiazol-6-yl instead of 3,5-dichlorophenyl. Similarly, compounds 2 to 237 of Table 82 are the same as compounds 2 to 237 of Table 1, respectively, except that in the compounds of Table 82 Ar is 2-methylaminobenzothiazol-6-yl instead of 3,5-dichlorophenyl.

Table 83

The compounds in Table 83 are of the general formula (1) where Ar is benzoxazol-6-yl, n is 0, L is O, $R^1$ is methyl, and $R^2$ and $R^3$ have the values given in Table 1. Thus compound 1 of Table 83 is the same as compound 1 of Table 1 except that in compound 1 of Table 83 Ar is benzoxazol-6-yl instead of 3,5-dichlorophenyl. Similarly, compounds 2 to 237 of Table 83 are the same as compounds 2 to 237 of Table 1, respectively, except that in the compounds of Table 83 Ar is benzoxazol-6-yl instead of 3,5-dichlorophenyl.

Table 83A

The compounds in Table 83A are of the general formula (1) where Ar is benzo[b]thiophene-6-yl, n is 0, L is O, $R^1$ is methyl, and $R^2$ and $R^3$ have the values given in Table 1. Thus compound 1 of Table 83A is the same as compound 1 of Table 1 except that in compound 1 of Table 83A Ar is benzo[b]thiophene-6-yl instead of 3,5-dichlorophenyl. Similarly, compounds 2 to 237 of Table 83A are the same as compounds 2 to 237 of Table 1, respectively, except that in the compounds of Table 83A Ar is benzo[b]thiophene-6-yl instead of 3,5-dichlorophenyl.

| Compound No. | $R^2$ | $R^3$ | |
|---|---|---|---|
| 12 | H | tert-$C_4H_9$ | oil |

Table 83B

The compounds in Table 83B are of the general formula (1) where Ar is benzofuran-6-yl, n is 0, L is O, $R^1$ is methyl, and $R^2$ and $R^3$ have the values given in Table 1. Thus compound 1 of Table 83B is the same as compound 1 of Table 1 except that in compound 1 of Table 83B Ar is benzofuran-6-yl instead of 3,5-dichlorophenyl. Similarly, compounds 2 to 237 of Table 83B are the same as compounds 2 to 237 of Table 1, respectively, except that in the compounds of Table 83B Ar is benzofuran-6-yl instead of 3,5-dichlorophenyl.

| Compound No. | $R^2$ | $R^3$ | |
|---|---|---|---|
| 12 | H | tert-$C_4H_9$ | oil |

Table 84

The compounds in Table 84 are of the general formula (1) where Ar is benzoxazol-6-yl, n is 0, L is O, $R^1$ is ethyl, and $R^2$ and $R^3$ have the values listed in Table 1. Thus compound 1 of Table 84 is the same as compound 1 of Table 84 except that in compound 1 of Table 84 $R^1$ is ethyl instead of methyl. Similarly, compounds 2 to 237 of Table 84 are the same as compounds 2 to 237 of Table 83, respectively, except that in the compounds of Table 84 $R^1$ is ethyl instead of methyl.

Table 85

The compounds in Table 85 are of the general formula (1) where Ar is 2,1-benzoisoxazol-5-yl, n is 0, L is O, $R^1$ is methyl, and $R^2$ and $R^3$ have the values given in Table 1. Thus compound 1 of Table 85 is the same as compound 1 of Table 1 except that in compound 1 of Table 85 Ar is 2,1-benzoisoxazol-5-yl instead of 3,5-dichlorophenyl. Similarly, compounds 2 to 237 of Table 85 are the same as compounds 2 to 237 of Table 1, respectively, except that in the compounds of Table 85 Ar is 2,1-benzoisoxazol-5-yl instead of 3,5-dichlorophenyl.

Table 86

The compounds in Table 86 are of the general formula (1) where Ar is benzothiazol-5-yl, n is 0, L is O, $R^1$ is methyl, and $R^2$ and $R^3$ have the values given in Table 1. Thus compound 1 of Table 86 is the same as compound 1 of Table 1 except that in compound 1 of Table 86 Ar is benzothiazol-5-yl instead of 3,5-dichlorophenyl. Similarly, compounds 2 to 237 of Table 86 are the same as compounds 2 to 237 of Table 1, respectively, except that in the compounds of Table 86 Ar is benzothiazol-5-yl instead of 3,5-dichlorophenyl.

Table 87

The compounds in Table 87 are of the general formula (1) where Ar is benzothiazol-5-yl, n is 0, L is O, $R^1$ is ethyl, and $R^2$ and $R^3$ have the values listed in Table 1. Thus compound 1 of Table 87 is the same as compound 1 of Table 87 except that in compound 1 of Table 87 $R^1$ is ethyl instead of methyl. Similarly, compounds 2 to 237 of Table 87 are the same as compounds 2 to 237 of Table 87, respectively, except that in the compounds of Table 87 $R^1$ is ethyl instead of methyl.

Tables 88 to 122

Tables 88 to 122 correspond exactly to Tables 1 to 35 (i.e. Table 88 corresponds exactly to Table 1, Table 89 corresponds exactly to Table 2, and so on) the only difference being that in each of Tables 88 to 122 L is S instead of O.

Tables 123 to 268

Tables 123 to 268 correspond exactly to Tables 1 to 122 (i.e. Table 123 corresponds exactly to Table 1, Table 124 corresponds exactly to Table 2, Table and so on) the only difference being that in each of Tables 123 to 268 n is 1 instead of 0.

Table 166

The compounds in Table 166 are of the general formula (1) where Ar is benzofuran-5-yl, n is 1, L is O, $R^1$ is methyl, and $R^2$ and $R^3$ have the values given in Table 1. Thus compound 1 of Table 166 is the same as compound 1 of Table 1 except that in compound 1 of Table 166 Ar is benzofuran-5-yl instead of 3,5-dichlorophenyl and n is 1 instead of 0. Similarly, compounds 2 to 237 of Table 166 are the same as compounds 2 to 237 of Table 1, respectively, except that in the compounds of Table 166 Ar is benzofuran-5-yl instead of 3,5-dichlorophenyl and n is 1 instead of 0.

| Compound No. | $R^2$ | $R^3$ | |
|---|---|---|---|
| 12 | H | tert-$C_4H_9$ | oil |
| 189 | H | $C_6H_5$—$(CH_3)_2$C— | oil |

Tables 269 to 414

Tables 269 to 414 correspond exactly to Tables 1 to 122 (i.e. Table 245 corresponds exactly to Table 1, Table 246 corresponds exactly to Table 2, and so on) the only difference being that in each of Tables 269 to 414, n is 2 instead of 0.

Table 312

The compounds in Table 312 are of the general formula (1) where Ar is benzofuran-5-yl, n is 2, L is O, $R^1$ is methyl, and $R^2$ and $R^3$ have the values given in Table 1. Thus compound 1 of Table 312 is the same as compound 1 of Table 1 except that in compound 1 of Table 312 Ar is benzofuran-5-yl instead of 3,5-dichlorophenyl and n is 2 instead of 0. Similarly, compounds 2 to 237 of Table 312 are the same as compounds 2 to 237 of Table 1, respectively, except that in the compounds of Table 312 Ar is benzofuran-5-yl instead of 3,5-dichlorophenyl and n is 2 instead of 0.

| Compound No. | $R^2$ | $R^3$ | |
|---|---|---|---|
| 12 | H | tert-$C_4H_9$ | 140-143° C. |
| 189 | H | $C_6H_5$—$(CH_3)_2$C— | 140-142° C. |

The compounds of general formula (1) may be prepared as outlined in Schemes 1 to 4 below, in which Ar, $R^1$, $R^2$ and $R^3$ have the meanings given above, $R^5$ is H or $C_{1-4}$ alkyl, as indicated, $R^{10}$ is $C_{1-6}$ alkyl, optionally substituted benzyl or optionally substituted thienylmethyl, $R^6$, $R^7$, $R^1$, $R^9$, $R^{12}$ and $R^{13}$ are independently H or $C_{1-3}$ alkyl, provided that when $R^{12}$ and $R^{13}$ are both alkyl their total number of carbon atoms does not exceed 3, m is 0, 1 or 2, DMF is N,N-dimethylformamide, NBS is N-bromosuccinimide, NCS is N-chlorosuccinimide and MCPBA is m-chloroperbenzoic acid. Other abbreviations are defined in the text.

Compounds of formula (1), where n is 0 and L is O, may be prepared as shown in Scheme 1. Esters of formula (2), where $R^5$ is $C_{1-4}$ alkyl, may be halogenated to give haloesters of formula (3), where Hal is a halogen atom such as bromine, chlorine or iodine, by reaction with a halogenating agent such as N-bromosuccinimide, in a suitable solvent such as carbon tetrachloride or acetonitrile, in the presence of a radical initiator such as AIBN (azo-isobutyronitrile), and a light source, at between ambient temperature and the reflux temperature of the solvent. Compounds of general formula (3) are then reacted with alkanethiols of general formula $R^1SH$, in the presence of a base such as sodium hydride, in a suitable solvent such as DMF, to give compounds of general formula (6), or are reacted with alkanethiol salts $R^1S^-M^+$, where M is a metal such as sodium or lithium, in a suitable solvent such as DMF, to give compounds of general formula (6).

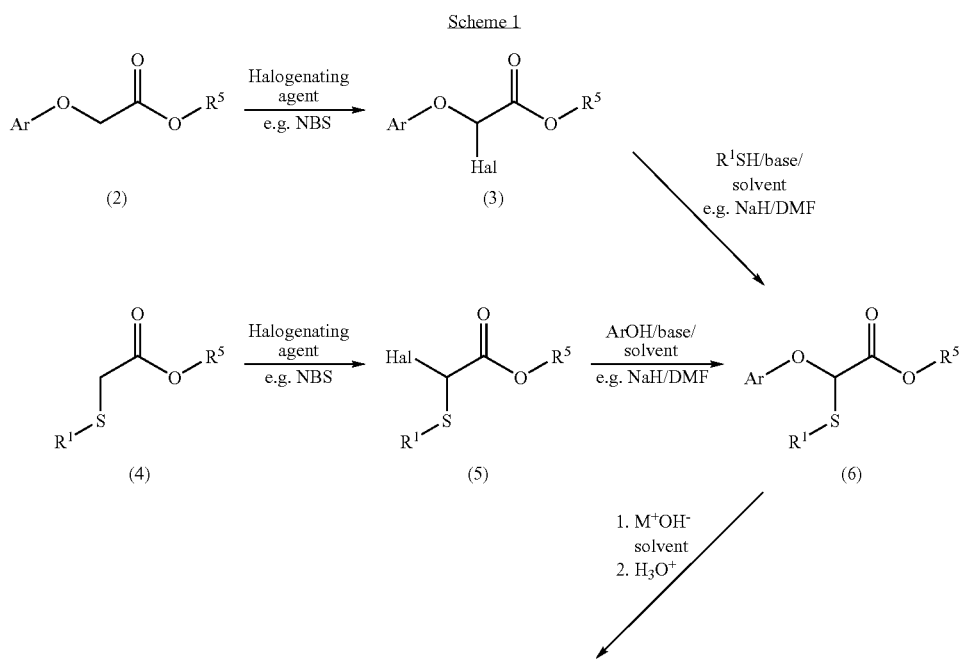

Scheme 1

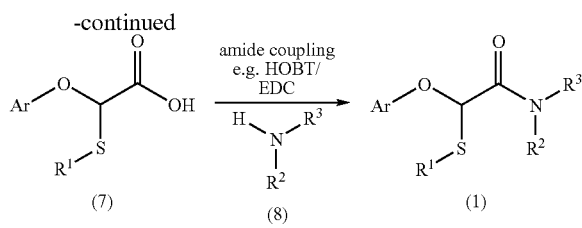

where n = 0

Alternatively esters of general formula (4) are halogenated to give haloesters of formula (5), where Hal is a halogen atom such as bromine, chlorine or iodine, by reaction with a halogenating agent such as N-chlorosuccinimide or N-bromosuccinimide or sulphuryl chloride, in a suitable solvent such as carbon tetrachloride or acetonitrile or dichloromethane, at between 0° C. and the reflux temperature of the solvent. Haloesters of formula (5) are reacted with hydroxy(hetero)aryls ArOH, where Ar is as defined above, in the presence of a base such as potassium t-butoxide, potassium carbonate, or sodium hydride in a suitable solvent such as t-butanol, 1,4-dioxane or DMF, at between ambient temperature and the reflux temperature of the solvent, to give compounds of formula (6). Compounds of formula (6) are hydrolysed to acids of formula (7) by reaction with an alkali metal hydroxide $M^+OH^-$, in a suitable solvent such as aqueous methanol, ethanol, or THF (tetrahydrofuran) at between ambient temperature and the reflux temperature of the solvent followed by acidification. Acids of formula (7) can be condensed with amines of formula (8), using suitable activating agents such as HOBT (1-hydroxybenzotriazole) and EDC (1-ethyl-3-N,N-dimethylaminopropylcarbodiimide hydrochloride), at between 0° C. and ambient temperature in a suitable solvent such as DMF, to give compounds of general formula (1) where n is 0 and L is O.

Compounds of general formula (1), where n is 1 or 2, are prepared by oxidation of compounds (1) where n=0 to the sulphoxide (n is 1) or sulphone (n is 2) oxidation state, as shown in Scheme 2. For example, esters of the general formula (6) where $R^5$ is $C_{1-4}$ alkyl can be oxidised to sulphoxides of formula (9) with an oxidising agent such as sodium periodate in a suitable solvent such ethanol, between 0° C. and ambient temperature. Sulphones of formula (10) can be made either directly from compounds of formula (6) with two or more equivalents of an oxidising agent such as m-chloroperbenzoic acid (MCPBA), in a suitable solvent such as dichloromethane between 0° C. and the reflux temperature of the solvent, or from sulphoxides of formula (9) with one or more equivalents of m-chloroperbenzoic acid. Sulphides of formula (6), sulphoxides of formula (9) or sulphones of formula (10) can be hydrolysed to the corresponding acids (7), (11) or (12) by reaction with an alkali metal hydroxide in a suitable solvent such as ethanol at between 0° C. and the reflux temperature of the solvent followed by acidification. The acids of formula (7), (11) or (12) can be condensed with amines of formula (8), using suitable activating agents such as HOBT and EDC, at between 0° C. and ambient temperature, to give compounds of general formula (1) where n is 0, 1 or 2.

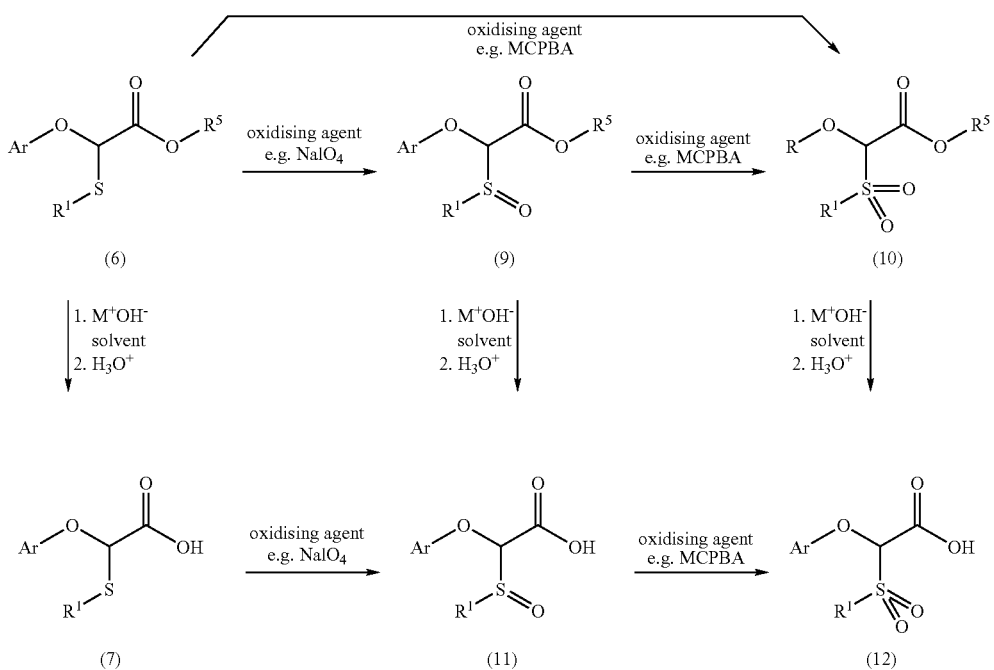

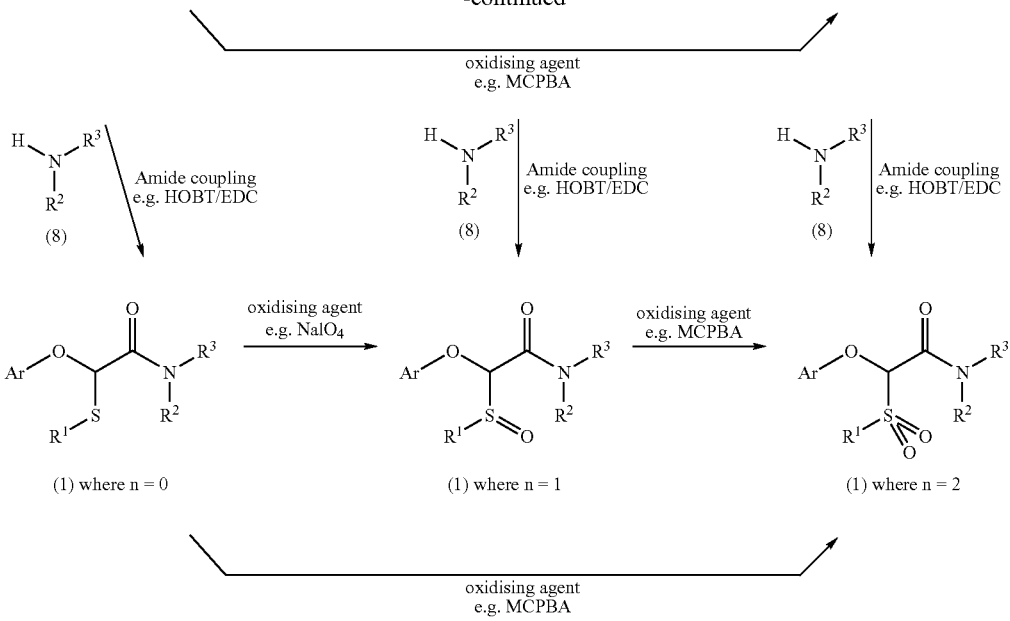

Similarly, sulphoxides of formula (11) and of formula (1) where n is 1 can be prepared from sulphides of formula (7) and of formula (1) where n is 0 respectively, using oxidising agents such as sodium metaperiodate or m-chloroperbenzoic acid as described above. Sulphones of formula (12) and of formula (1) where n is 2, can be prepared either from sulphides of formula (7) and of formula (1) where n is 0, by using at least two equivalents of oxidising agents such as m-chloroperbenzoic acid, or from sulphoxides of formula (11) and of formula (1) where n is 1, using one or more equivalents of oxidising agents such as m-chloroperbenzoic acid, as described above.

Compounds of formula (1) can also be prepared as shown in Scheme 3. Acids of formula (13) can be condensed with amines of formula (8), using suitable activating agents such as HOBT and EDC, at between 0° C. and ambient temperature, to give compounds of formula (14). Compounds of formula (14) can be halogenated to compounds of formula (16) using a halogenating agent such as N-chlorosuccinimide, in a suitable solvent such as carbon tetrachloride or acetonitrile, at between 0° C. and ambient temperature. Amides of formula (16) can also be prepared from acid halides of formula (15) by reaction with amines of formula (8) in the presence of a base such as triethyl-amine in a suitable solvent such as dichloromethane, at between 0° C. and ambient temperature.

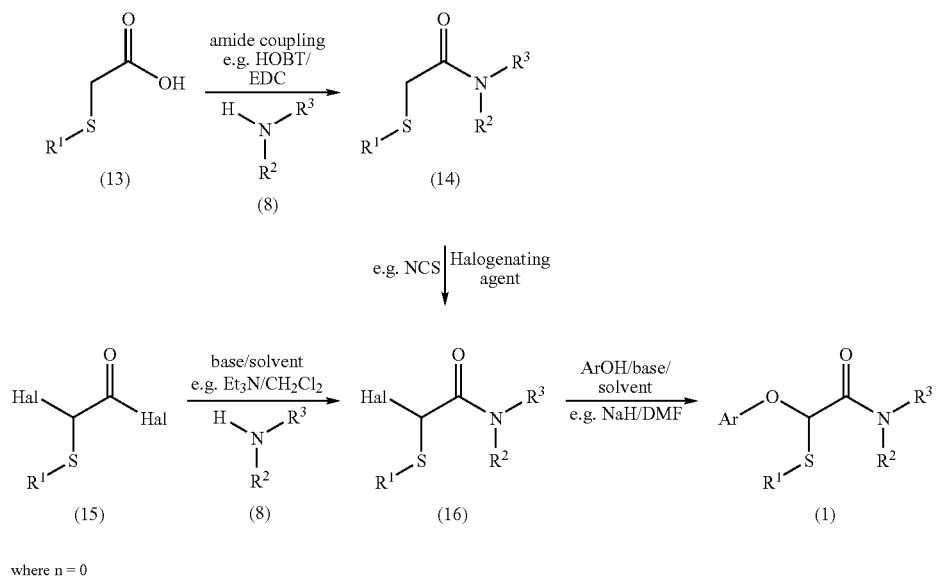

Halosulphides of formula (16) can be reacted with hydroxy (hetero)aryls ArOH, in the presence of a base such as potassium carbonate or sodium hydride, in a suitable solvent such as DMF, at between 0° C. and 80° C., to give compounds of formula (1) where n is 0.

As shown in Scheme 4, amines of the general formula (18) or (20), which are examples of amines of the general formula (8) wherein $R^2$ is H, may be prepared by alkylation of an aminoalcohol of the general formula (17) or (19) using a suitable base, such as n-butyl lithium or sodium hydride, followed by reaction with a suitable alkylating reagent $R^{10}LG$, such as an alkyl iodide, for example, methyl iodide, to form an alkylated compound of the general formula (18) or (20), respectively. A carbonyl derivative $R^{12}COR^{13}$ (21), for example formaldehyde, can be reacted with ammonia, usually in form of ammonium chloride, and cyanide, conveniently in form of an aqueous solution sodium cyanide, to provide an α-aminoalkyne (22) (Strecker synthesis).

Scheme 4

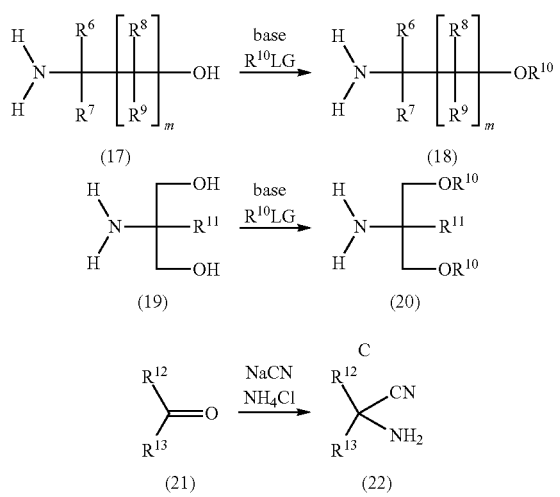

Other amines of the general formula (8) are either commercially available or may be prepared by standard literature methods or standard modifications.

Thioamides (Compounds of the general formula (1) where L=S (such as 2-(3-bromo-quinolin-6-yloxy)-N-tert-butyl-2-methylsulfanyl-thioacetamide {13C NMR (CDCl$_3$) δ (C=S) 193.3 ppm} derived from compound number 12 of Table 72) may be prepared from the corresponding amides using thionating agents such as phosphorus pentasulphide, Lawesson's or Davy's reagents or prepared from the corresponding thionoacids or thionoesters using standard literature methods or standard modifications.

Hydroxy (hetero)aryls ArOH are either commercially available or may be prepared by standard literature methods (see, for example, Ann. Chem., Justus Liebigs (1966), 98-106 for the synthesis of 3-bromo-6-hydroxy-quinoline used for the preparation of compounds in Table 57; Journal of the Chemical Society, Perkin Transactions 1: Organic and Bio-Organic Chemistry (1972-1999) (1982), (3), 815-21 for the synthesis of benzo[b]thiophen-6-ol used for the preparation of compounds in Table 83A: Journal of Medicinal Chemistry 2004, 47(20), 4829-4837 for the synthesis of benzofuran-6-ol used for the preparation of compounds in Table 83B and European Journal of Organic Chemistry (2000), (3), 491-497 for the synthesis of 7-bromo-naphthalen-2-ol used for the preparation of compounds in Table 67).

The compounds of formula (1) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei*, *Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveilluia taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Altentaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoina* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphyliuni* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothytium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultinium*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale*, *Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodernium seditiosum*) or lumber, notably *Cephaloascus fragrans, Ceratocystis* spp., *Ophiostoma piceae, Penicillium* spp., *Trichodenna pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octyl-pyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (1) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefin sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) propionamide), acibenzolar-5-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-5-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxy-carbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

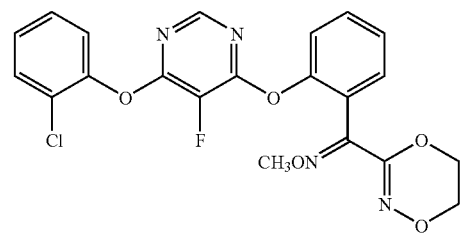

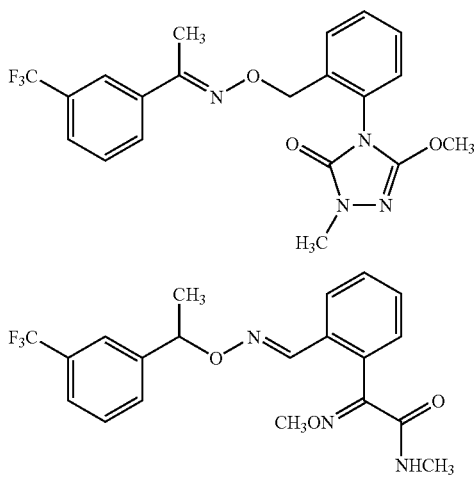

The compounds of formula (1) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:

| | |
|---|---|
| ml = | millilitres |
| m.p. = | melting point (uncorrected) |
| g = | grammes |
| b.p. = | boiling point |
| THF = | tetrahydrofuran |
| DMSO = | dimethylsulphoxide |
| M$^+$ = | mass ion |
| DMF = | N,N-dimethylformamide |
| s = | singlet |
| d = | doublet |
| HOBT = | 1-hydroxybenzotriazole |
| HOAT = | 7-aza-1-hydroxybenzotriazole |
| bs = | broad singlet |
| NMR = | nuclear magnetic resonance |
| t = | triplet |
| HPLC = | high performance liquid chromatography |
| q = | quartet |
| TLC = | thin layer chromatography |
| m = | multiplet |
| glc = | gas-liquid chromatography |
| ppm = | parts per million |
| EDC = | 1-ethyl-3-N,N-dimethylamino propylcarbodiimide hydrochloride |
| M = | molar |

EXAMPLE 1

This Example illustrates the preparation of 2-(3,5-dichlorophenoxy)-2-methylthio-N-2-methylprop-2-yl acetamide (Compound No. 12 of Table 1)

Stage 1: Preparation of 2-methylthio-2-(3,5-dichlorophenoxy)acetic acid

Step 1 t-Butyl 2-bromo-2-(3,5-dichlorophenoxy)acetate (1.0 g) was dissolved in 1,4-dioxane (3 ml), and sodium thiomethoxide (0.218 g) was added to the mixture. The resulting pale yellow suspension was stirred at ambient temperature for 5 hours and then stored for 18 hours. The solvent was evaporated, water was added and the aqueous layer was extracted twice with ethyl acetate (100 ml). The organic layers were combined, washed with brine, dried over magnesium sulphate, filtered and evaporated to give t-butyl 2-methylthio-2-(3,5-dichlorophenoxy)acetate as a pale yellow solid (0.80 g) which was used in the next step without further purification.

$^1$H NMR (CDCl$_3$) δ ppm: 1.52 (9H, s); 2.19 (3H, s), 5.39 (1H, s); 6.92 (2H, d); 7.04 (1H, t).

Step 2

To the product of Step 1 (0.2 g) in methanol (3 ml) at ambient temperature was added a solution of sodium hydroxide (0.050 g) in water (1 ml). The reaction was stirred for 2 hours, the solvent evaporated then water and ethyl acetate were added. The aqueous phase was separated, acidified with dilute aqueous hydrochloric acid then extracted with ethyl acetate. The organic phases were combined, dried over magnesium sulphate, filtered and evaporated to give 2-methylthio-2-(3,5-dichlorophenoxy)acetic acid as a pale yellow gum (0.153 g).

$^1$H NMR (CDCl$_3$) δ ppm: 2.21 (3H, s); 5.59 (1H, s); 6.95 (2H, s); 7.08 (1H, s).

Stage 2

2-Methylthio-2-(3,5-dichlorophenoxy)acetic acid (0.27 g), in dry N,N-dimethylformamide (6 ml) was treated with t-butylamine (0.077 g), N-(3-dimethylaminopropyl)-N'-ethyl carbodiimide hydrochloride (0.211 g), HOAt (0.15 g) and triethylamine (0.28 ml) at ambient temperature with stirring for 10 hours. The mixture was poured into water, extracted with ethyl acetate (three times) and the extracts combined, washed with saturated aqueous sodium carbonate solution, water (three times) then dried over magnesium sulfate, filtered and evaporated under reduced pressure to give an oil. The oil was fractionated by chromatography (silica; hexane/ethyl acetate, 95:5 by volume) to give the required product, 0.03 g, as a pale yellow solid, m.p. 125-126° C.

$^1$H NMR (CDCl$_3$) δ ppm: 1.36 (9H, s); 2.08 (3H, s); 5.34 (1H, s); 6.24 (1H, bs); 6.86 (2H, d); 9.02 (1H, t).

The following amides were prepared using a similar procedure.

Compound No. 122 of Table 1: using 2-aminomethylfuran, $^1$H NMR (CDCl$_3$) δ ppm: 2.10 (3H, s); 4.48-4.66 (2H, 2×dd); 5.56 (1H, s); 6.29 (1H, d); 6.33 (1H, m); 6.88 (1H, bs); 6.92 (2H, d); 7.09 (1H, t); 7.38 (1H, m).

Compound No. 150 of Table 1: using benzylamine, $^1$H NMR (CDCl$_3$) δ ppm: 2.13 (3H, s); 4.48-4.64 (2H, 4×d); 5.57 (1H, s); 6.86 (1H, s); 6.92 (1H, s); 7.08 (1H, t); 7.30-7.38 (5H, m).

EXAMPLE 2

This Example illustrates the preparation of 2-(3,4,5-trimethylphenoxy)-2-methylthio-N-(2-methyl-prop-2-yl)acetamide (Compound No. 12 of Table 13) and 2-(4-bromo-3,5-dimethylphenoxy)-2-methylthio-N-(2-methyl-prop-2-yl)acetamide (Compound No. 12 of Table 15)

Stage 1: Preparation of 2-methylthio-2-(3,4,5-trimethylphenoxy)acetic acid

Step 1: Preparation of ethyl 2-chloro-2-methylthioacetate

To a stirred solution of ethyl 2-methylthioacetate (10.0 g) in dry acetonitrile (50 ml) at 0° C. was added in portions N-chlorosuccinimide (NCS, 9.8 g), maintaining the reaction temperature below 5° C. during the addition. The mixture was stirred for 0.5 hours then further NCS (0.5 g) was added to complete the reaction and the suspension stirred for a further 0.5 hours. The mixture was treated with saturated aqueous sodium hydrogen carbonate, the organic phase separated and the aqueous phase extracted with diethyl ether (twice). The organic fractions were combined, washed with aqueous sodium hydrogen carbonate (twice), brine (twice) then dried over magnesium sulfate, filtered and the solvent evaporated under reduced pressure to give ethyl 2-chloro-2-methylthioacetate, (9.2 g), as a colourless liquid. The product was used in the next Stage without further purification.

$^1$H NMR (CDCl$_3$) δ ppm: 1.32-1.36 (3H, t); 2.32 (3H, s); 4.26-4.32 (2H, q); 5.36 (1H, s).

Step 2: Preparation of ethyl 2-methylthio-2-(3,4,5-trimethylphenoxy)acetate

To a stirred suspension of sodium hydride (0.33 g, 60% in mineral oils) in dry N,N-dimethylformamide (2 ml) under an atmosphere of nitrogen was added 3,4,5-trimethylphenol (11.0 g) in N,N-dimethylformamide (20 ml) over 5 minutes at ambient temperature. The mixture was stirred for 1 hour and diluted with further N,N-dimethylformamide (40 ml) then added dropwise simultaneously with a solution of ethyl 2-chloro-2-thioacetate (1.87 g) in N,N-dimethylformamide (10 ml) to a stirred suspension of anhydrous potassium carbonate (1.5 g) in dry DMF (10 ml) heated to 50° C. with stirring for 0.75 hours. The mixture was cooled to ambient temperature, poured into water then extracted with ethyl acetate (three times). The extracts were combined, washed with water (three times), dried over magnesium sulphate then evaporated to give a yellow oil, 2.15 g, containing ethyl 2-methylthio-2-(3,4,5-trimethylphenoxy)acetate and some unreacted trimethylphenol. A portion of the oil was fractionated by chromatography (silica; hexane:ethyl acetate) to give a pure sample of ethyl 2-methylthio-2-(3,4,5-trimethylphenoxy)acetate as a pale yellow oil. The remainder of the oil was used in Step 3 without further purification.

$^1$H NMR (CDCl$_3$) δ ppm: 1.30-1.34 (3H, t); 2.10 (3H, s); 2.20 (3H, s); 2.26 (6H, s); 4.28-4.36 (2H, m); 5.56 (1H, s); 6.70 (2H, s).

Step 3

The product from Step 2 (2.0 g) in THF (10 ml) and water (3 ml) containing sodium hydroxide (0.4 g) were stirred at 60° C. for 2 hours then cooled to ambient temperature, evaporated under reduced pressure, diluted with water and washed with diethyl ether. The aqueous fraction was acidified with dilute hydrochloric acid and extracted with ethyl acetate (three times). The extracts were combined, washed with brine, dried over magnesium sulphate, then evaporated to give 2-methylthio-2-(3,4,5-trimethylphenoxy)acetic acid, 1.05 g, as a yellow gum. A portion of the gum was fractionated by chromatography (silica; ethyl acetate then methanol) to provided an analytical sample and the remainder used in the next stage without further purification.

$^1$H NMR (CDCl$_3$) δ ppm: 2.12 (3H, s); 2.24 (3H, s); 2.26 (6H, s); 5.64 (1H, s); 6.72 (2H, s).

Stage 2

In a similar procedure to Stage 2 of Example 1, 2-methylthio-2-(3,4,5-trimethyl-phenoxy)acetic was condensed with tert-butylamine to give 2-methylthio-2-(3,4,5-trimethylphenoxy)-2-methylthio-N-(2-methylprop-2-yl)acetamide.

$^1$H NMR (CDCl$_3$) δ ppm: 1.34 (9H, s); 2.04 (3H, s); 2.08 (3H, s); 2.20 (6H, s); 5.34 (1H, s); 6.44 (1H, s); 6.60 (2H, s).

In a similar procedure to Stage 1, Step 1 of Example 2, 4-bromo-3,5-dimethylphenol was reacted with ethyl 2-bromo-2-methylthioacetate to give ethyl 2-methylthio-2-(4-bromo-3,5-dimethylphenoxy)acetate as a pale yellow liquid.

$^1$H NMR (CDCl$_3$) δ ppm: 1.33 (3H, t); 2.20 (3H, s); 2.39 (6H, s); 4.31 (2H, m); 5.53 (1H, s); 6.77 (2H, s).

In a similar procedure to Stage 1, Step 1 of Example 2, 4-cyano-3,5-dimethylphenol was reacted with ethyl 2-chloro-2-methylthioacetate to give ethyl 2-methylthio-2-(4-cyano-3,5-dimethylphenoxy)acetate as a pale yellow liquid.

$^1$H NMR (CDCl$_3$) δ ppm: 1.34 (3H, t); 2.20 (3H, s); 2.51 (6H, s); 4.32 (2H, q); 5.49 (1H, s); 6.75 (2H, s).

In a similar procedure to Stage 1, Step 2 of Example 1, ethyl 2-methylthio-2-(4-bromo-3,5-dimethylphenoxy)acetate was hydrolysed to give 2-methylthio-2-(4-bromo-3,5-dimethylphenoxy)acetic acid as an off-white solid.

$^1$H NMR (CDCl$_3$) δ ppm: 2.23 (3H, s); 2.40 (6H, s); 5.61 (1H, s); 6.79 (2H, s).

In a similar procedure to Stage 1, Step 2 of Example 1, ethyl 2-methylthio-2-(4-cyano-3,5-dimethylphenoxy)acetate was hydrolysed to give 2-methylthio-2-(4-cyano-3,5-dimethylphenoxy)acetic acid as a colourless solid.

$^1$H NMR (CDCl$_3$) δ ppm: 2.24 (3H, s); 2.52 (6H, s); 5.67 (1H, s); 6.78 (2H, s).

In a similar procedure to Stage 2 of Example 1, 2-methylthio-2(4-bromo-3,5-dimethylphenoxy)acetic acid was condensed with tert-butylamine to give 2-(4-bromo-3,5-dimethylphenoxy)-2-methylthio-N-(2-methyl-prop-2-yl)acetamide as a colourless solid, m.p. 123-125° C.

$^1$H NMR (CDCl$_3$) δ ppm: 1.41 (9H, s); 2.14 (3H, s); 2.39 (6H, s); 5.39 (1H, s); 6.41 (1H, s); 6.74 (2H, s).

The following amides were prepared using a similar procedure.

Compound No. 52 of Table 13: using 2-cyano-1-methoxy-prop-2-ylamine, $^1$H NMR (CH$_3$CN) δ ppm: 3.40 (3H, 2×s); 3.66 (2H, m); 5.58 (1H, 2×s); 6.68 (2H, s); 7.25 (1H, 2×s).

Compound No. 120 of Table 13: using thiazol-2-ylamine, $^1$H NMR (CH$_3$CN) δ ppm: 5.85 (1H, s); 6.76 (2H, s); 7.10 (1H, d); 7.45 (1H, d).

Compound No. 70 of Table 13: using allylamine, $^1$H NMR (CH$_3$CN) δ ppm: 3.83 (2H, t); 5.10 (2H, m); 5.55 (1H, s); 5.82 (1H, m); 6.68 (2H, s); 7.23 (1H, s).

Compound No. 150 of Table 13: using benzylamine, $^1$H NMR (CH$_3$CN) δ ppm: 5.57 (1H, s); 6.67 (2H, s); 7.26 (5H, m); 7.58 (1H, s).

Compound No. 124 of Table 13: using thienylmethylamine, $^1$H NMR (CH$_3$CN) δ ppm: 4.56 (2H, t); 5.54 (1H, s); 6.66 (2H, s); 6.92 (2H, m); 7.24 (1H, d); 7.64 (1H, s).

Compound No. 47 of Table 17: using 1-methoxy-2-methylprop-2-ylamine and 2-methylthio-2-(4-cyano-3,5-dimethylphenoxy)acetic acid, $^1$H NMR (CDCl$_3$) δ ppm: 1.36 (3H, s); 1.40 (3H, s); 2.15 (3H, s); 2.51 (6H, s); 3.38 (3H, s); 3.39 (2H, q); 5.49 (1H, s); 6.63 (1H, s); 6.73 (2H, s), colourless solid m.p. 123-125° C.

EXAMPLE 3

This Example illustrates the preparation of 2-(5-chloropyridyl-3-oxy)-2-(methylthio)-N-(2-methylprop-2-yl) acetamide (Compound No. 12 of Table 70)

Stage 1: Preparation of ethyl 2-bromo-2-methylthioacetate

To a stirred solution of ethyl 2-methylthioacetate (40.2 g) in carbon tetrachloride (250 ml) at 15° C. was added in portions N-bromosuccinimide (NBS, 54 g) maintaining the reaction temperature below 20° C. during the addition. The mixture was stirred for 5 hours then further NBS (10 g) was added in portions and the reaction stirred for a further 18 hours. The mixture was washed with aqueous sodium carbonate then brine, dried over magnesium sulfate, filtered and the solvent evaporated under reduced pressure to give (56 g) as an orange liquid containing 10% of unreacted ethyl 2-methylthioacetate. The product was used in the next Stage without further purification. An analytical sample of ethyl 2-bromo-2-methylthioacetate was obtained by vacuum distillation, b.p. 54-56° C. at 0.1 mmHg.

$^1$H NMR (CDCl$_3$) δ ppm: 1.30 (3H, s); 2.34 (3H, s); 4.26 (2H, q); 5.39 (1H, s).

Stage 2: Preparation of 2-(5-chloropyridyl-3-oxy)-2-(methylthio)-N-(2-methylprop-2-yl)acetamide Step 1
5-Chloro-3-hydroxypyridine (1.30 g), ethyl 2-bromo-2-methylthioacetate (2.43 g, 70% pure) and anhydrous potassium carbonate (1.38 g) were stirred in dry DMF (15 ml) and heated to 80° C. with stirring for 1 hour. The mixture was cooled to ambient temperature, poured into water then extracted with diethyl ether (three times). The extracts were combined, washed with water, dried over magnesium sulphate then evaporated to give an oil, which was purified by flash chromatography on silica gel (40-60 mesh) eluting with hexane/ethyl acetate (1:1 by volume), to give ethyl 2-(5-chloropyridyl-3-oxy)-2-(methylthio)acetate as an orange oil (0.65 g).

$^1$H NMR (CDCl$_3$) δ ppm: 1.34-1.38 (3H, t); 2.20 (3H, s); 4.30-4.38 (2H, m); 5.58 (1H, s); 7.38 (1H, m); 8.30-8.32 (2H, d).

Step 2
The product from Step 1 (0.62 g) in THF (10 ml) and water (3 ml) containing sodium hydroxide (0.19 g) were stirred at 60° C. for 1.5 hours then cooled to ambient temperature and stored for 18 hours. The mixture was evaporated and the residue was diluted with water then washed with diethyl ether. The aqueous fraction was acidified with dilute hydrochloric acid and extracted with ethyl acetate. The extracts were combined, washed with water, dried over magnesium sulphate, then evaporated to give 2-(5-chloropyridyl-3-oxy)-2-(methylthio)acetic acid, 0.48 g, as a dark yellow gum.

$^1$H NMR (CDCl$_3$) δ ppm: 2.24 (3H, s); 5.72 (1H, s); 7.54 (1H, m); 8.34 (1H, s); 8.40 (1H, s); 9.52 (1H, bs).

Step 3
In a similar procedure to Stage 2 of Example 1, 2-(5-chloropyridyl-3-oxy)-2-(methylthio)acetic acid was condensed with tert-butylamine to give the required product as a colourless oil.

$^1$H NMR (CDCl$_3$) δ ppm: 1.41 (9H, s); 2.14 (3H, s); 5.47 (1H, s); 6.35 (1H, bs); 7.36 (1H, t); 8.28 (1H, d); 8.30 (1H, d).

The following amides were made in a similar procedure:
Compound No. 50 of Table 70: using 1-methylthio-2-methylprop-2-ylamine, pale yellow oil, $^1$H NMR (CDCl$_3$) δ ppm: 1.48 (6H, s); 2.17 (3H, s); 2.19 (3H, s); 2.97 (2H, dd); 5.47 (1H, s); 6.63 (1H, s); 7.39 (1H, t); 8.30 (1H, d); 8.32 (1H, d).

Compound No. 52 of Table 70: using 2-cyano-1-methoxyprop-2-ylamine, gum, $^1$H NMR (CDCl$_3$) δ ppm: 1.81 (3H, 2×s); 2.18 (3H, 2×s); 3.52 (3H, 2×s); 2.64-3.80 (2H, 4×d); 5.59 & 5.60 (1H, 2×s); 7.02 & 7.07 (1H, 2×s); 7.39 (1H, m); 8.31 (1H, m); 8.35 (1H, m), data consistent with a 1:1 mixture of diastereoisomers.

EXAMPLE 4

This Example illustrates the preparation of 2-(benzothiazolyl-6-oxy)-2-(methylthio)-N-(2-methylprop-2-yl)acetamide (Compound No. 12 of Table 78)

Stage 1: Preparation of 6-hydroxybenzothiazole

Step 1: Preparation of 6-methoxybenzothiazole

2-Amino-6-methoxybenzothiazole (9.0 g) in dry DMF (10 ml) was added dropwise over 35 minutes to a stirred solution of t-butyl nitrite (9.9 ml) in DMF (40 ml) at 65° C. The temperature of the mixture was kept <73° C. during the addition. On complete addition of the solution of benzothiazole, the dark red solution was stirred for an additional 15 minutes, cooled to ambient temperature then poured into dilute hydrochloric acid (200 ml) and diluted with brine. The dark red suspension was extracted with diethyl ether and the solid filtered then washed with further water and diethyl ether. The diethyl ether extracts were combined and the aqueous fraction re-extracted with ethyl acetate. The organic fractions were combined, washed with water and dried over magnesium sulphate then evaporated to give a brown solid. The solid was purified by flash column chromatography on silica gel (40-60 mesh) eluting with hexane/ethyl acetate (4:1 by volume) to give 6-methoxybenzothiazole as a colourless solid (2.1 g).

$^1$H NMR (CDCl$_3$) δ ppm: 3.89 (3H, s); 7.12 (1H, dd); 7.40 (1H, d); 8.01 (1H, d); 8.82 (1H, s).

Step 2:
The product of Step 1 (1.2 g) in hydrobromic acid (10 ml, 48%) was heated at 120° C. with stirring for 6 hours then stored at ambient temperature for 2 days. The hot, pale yellow solution produced a suspension on cooling. The suspension was dissolved by the addition of water then the solution was adjusted to pH 6 by addition of sodium hydrogen carbonate and the solid that precipitated was filtered from solution, washed with water and sucked to dryness. The solid was dissolved in ethyl acetate, the solution dried over magnesium sulphate and evaporated to give 6-hydroxybenzothiazole as a colourless solid (1.05 g).

$^1$H NMR (CDCl$_3$) δ ppm: 7.07 (1H, dd); 7.91 (1H, d); 8.76 (1H, d); 9.18 (1H, s).

Stage 2: Preparation of 2-(benzothiazolyl-6-oxy)-2-methylthioacetic acid

Step 1: Preparation of 2-(benzothiazolyl-6-oxy)-2-(methylthio acetate

6-Hydroxybenzothiazole (1.10 g), ethyl 2-bromo-2-methylthioacetate (2.22 g, 73% pure) and anhydrous potassium carbonate (2.0 g) were stirred in dry DMF (5 ml) at 80° C. for 0.5 hours then cooled to ambient temperature. The mixture was poured into saturated aqueous ammonium chloride, made acidic with dilute hydrochloric acid then extracted with diethyl ether. The extract was washed with water, dried over magnesium sulphate and evaporated to give a brown gum. The gum was purified by flash column chromatography on silica gel (40-60 mesh) eluting with hexane/ethyl acetate (1:1 by volume) to give ethyl 2-(benzothiazolyl-6-oxy)-2-(methylthio)acetate as a yellow solid (0.50 g).

$^1$H NMR (CDCl$_3$) δ ppm: 1.37 (3H, t); 2.27 (3H, s); 4.30-4.42 (2H, m); 5.65 (1H, s); 7.28 (1H, m); 7.59 (1H, m); 8.08 (1H, d); 8.90 (1H, s).

Step 2: Preparation of 2-(benzothiazolyl-6-oxy)-2-(methylthio)acetic acid

To a stirred solution of ethyl 2-(benzothiazolyl-6-oxy)-2-(methylthio)acetate (0.50 g) in THF (4 ml) was added a solution of lithium hydroxide monohydrate (0.076 g) in water (1 ml) at ambient temperature. After 1 hour, the mixture was made acidic with dilute sulphuric acid, extracted with diethyl ether and the extract was dried over magnesium sulphate then evaporated to give 2-(benzothiazolyl-6-oxy)-2-(methylthio)-acetic acid as a pale yellow solid (0.45 g).

$^1$H NMR (CDCl$_3$) δ ppm: 2.28 (3H, s); 5.72 (1H, s); 7.28 (1H, dd); 7.60 (1H, m); 8.11 (1H, d); 8.99 (1H, s).

Step 3

In a similar procedure to Stage 2 of Example 1, 2-(benzothiazolyl-6-oxy)-2-(methylthio)acetic acid was condensed with tert-butylamine to give 2-(benzothiazolyl-6-oxy)-2-(methylthio)-N-2-methylprop-2-yl acetamide.

$^1$H NMR (CH$_3$CN) δ ppm: 1.34 (9H, s); 5.56 (1H, s); 6.69 (1H, s); 7.25 (1H, d); 7.66 (1H, s); 7.98 (1H, d); 8.96 (1H, s).

The following amides were prepared using a similar procedure.

Compound No. 70 of Table 78: using allylamine, $^1$H NMR (CH$_3$CN) δ ppm: 3.86 (2H, m); 5.56 (1H, s); 5.84 (1H, m); 7.26 (1H, d); 7.36 (1H, m); 7.36 (2H, d); 7.68 (1H, s); 7.99 (1H, d); 8.97 (1H, s).

Compound No. 189 of Table 78: using 2-phenyl-prop-2-ylamine, $^1$H NMR (CH$_3$CN) δ ppm: 1.60 (6H, s); 5.61 (1H, s); 7.17 (1H, t); 7.25 (5H, m); 7.36 (2H, d); 7.66 (1H, s); 8.00 (1H, d); 8.98 (1H, s).

Compound No. 35 of Table 78: using 2-cyano-prop-2-ylamine, $^1$H NMR (CH$_3$CN) δ ppm: 1.68 (6H, d); 5.71 (1H, s); 7.30 (1H, m); 7.34 (1H, s); 7.69 (1H, s); 7.99 (1H, d); 8.98 (1H, s).

Compound No. 133 of Table 78: using 4-fluoroaniline, $^1$H NMR (CDCl$_3$) δ ppm: 2.24 (3H, s); 5.74 (1H, s); 7.08 (2H, t); 7.28 (1H, m); 7.61 (3H, m); 8.10 (1H, d); 8.40 (1H, s); 8.94 (1H, s).

Compound No. 52 of Table 78: using 2-cyano-1-methoxy-prop-2-ylamine, $^1$H NMR (CDCl$_3$) δ ppm: 1.81 (3H, 2×s); 2.20 (3H, s); 3.52 (3H, 2×s); 3.68 (1H, m); 3.78 (1H, m); 5.63 (1H, 2×s); 7.15 (1H, 2×s); 7.24 (1H, m); 7.60 (1H, m); 8.10 (1H, d); 8.94 (1H, s).

EXAMPLE 5

This Example illustrates the preparation of 2-(3-chloroquinolinyl-6-oxy)-2-methylthio-N-(2-methylprop-2-yl)acetamide (Compound No. 12 of Table 58)

Stage 1: Preparation of 3-chloro-6-hydroxyquinoline

To a stirred solution of 3-bromo-6-hydroxyquinoline (1.0 g) in N-methylpyrrolidin-2-one (12 ml, deoxygenated by bubbling nitrogen through the solution) was added copper (1) chloride (1.10 g) and potassium chloride (1.66 g). The mixture was heated to 120° C. for 2 hours under an atmosphere of nitrogen then for 2 hours at 170° C. The reaction was diluted with saturated aqueous ammonium chloride solution, ethyl acetate was added and the mixture was stirred to dissolve the required product. The mixture was filtered to remove the insoluble material and the organic phase separated. The aqueous phase was extracted with ethyl acetate (three times) and the insoluble material washed with warm ethyl acetate. The ethyl acetate fractions were combined, washed with water, dried over magnesium sulphate then evaporated under reduced pressure to give a solid. The solid was fractionated by chromatography (silica; ethyl acetate/hexane 9:1 by volume) to give 3-chloro-6-hydroxyquinoline, 0.7 g, as a colourless solid.

$^1$H NMR (CDCl$_3$) δ ppm: 7.06 (1H, d); 7.35 (1H, dd); 7.91 (1H, d); 7.96 (1H, d); 8.59 (1H, d); 9.55 (1H, s).

Stage 2
Step 1

To a stirred solution of 3-chloro-6-hydroxyquinoline (8.98 g) in dry DMF (200 ml) containing anhydrous potassium carbonate (20.7 g) at ambient temperature was added dropwise a solution of ethyl 2-bromo-2-methylthioacetate (13.0 g) in N,N-dimethylformamide (50 ml) over 5 minutes. The mixture was heated for 2.5 hours at 70-75° C. then cooled to ambient temperature, diluted with water and extracted with ethyl acetate (four times). The extracts were combined, washed with brine, dried over magnesium sulfate, filtered and evaporated under reduced pressure to give a brown oil (21 g) containing the required product that was used in the next stage without further purification. A portion of the oil (0.5 g) was fractionated by chromatography (silica; hexane:ethyl acetate) to give ethyl 2(3-chloro-6-oxyquinoline)-2-methylthioacetate as a yellow oil, 0.18 g.

$^1$H NMR (CDCl$_3$) δ ppm: 1.34-1.38 (3H, t); 2.26 (3H, s); 4.30-4.38 (2H, m); 5.72 (1H, s) 7.16 (1H, d); 7.48-7.52 (1H, dd); 8.02-8.06 (2H, m); 8.72 (1H, s).

Step 2

To a stirred solution of the product from Stage 2 Step 1 (20.5 g) in tetrahydrofuran (150 ml) at ambient temperature was added a solution of sodium hydroxide (3.3 g) in water (15 ml). The mixture was stirred for 3 hours then evaporated under reduced pressure, the residue diluted with water, and washed with diethyl ether (twice). The aqueous fraction was acidified with concentrated hydrochloric acid to give a brown precipitate that was filtered from solution, washed with cold water and sucked to dryness to give 2(3-chloroquinolinyl-6-oxy)-2-methylthioacetic acid (8.5 g), m.p. 173-174° C.

$^1$H NMR (DMSO-d$_6$) δ ppm: 2.16 (3H, s); 6.10 (1H, s) 7.50 (1H, m); 7.54-7.58 (1H, dd); 7.98-8.02 (1H, d); 8.44 (1H, s); 8.76 (1H, s); 13.6 (1H, bs).

Step 3

In a similar procedure to Stage 2 of Example 1, 2-(3-chloroquinolinyl-6-oxy)-2-methylthioacetic acid was condensed with t-butylamine to give the required product.

$^1$H NMR (CH$_3$CN) δ ppm: 5.64 (1H, s); 6.71 (1H, s); 7.30 (1H, s); 7.51 (1H, d); 7.98 (1H, d); 8.16 (1H, s); 8.68 (1H, s).

The following amides were prepared using a similar procedure.

Compound No. 35 of Table 58: using 2-cyano-prop-2-ylamine, $^1$H NMR(CH$_3$CN) δ ppm: 5.80 (1H, s); 7.32 (1H, s); 7.36 (1H, s); 7.52 (1H, d); 7.99 (1H, d); 8.18 (1H, s); 8.68 (1H, s).

Compound No. 128 of Table 58: using 2-cyanoaniline, $^1$H NMR (CH$_3$CN) δ ppm: 6.03 (1H, s); 7.35 (1H, t); 7.46 (1H, s); 7.59 (1H, d); 7.68 (1H, t); 7.74 (1H, d); 7.88 (1H, d); 8.04 (1H, d); 8.23 (1H, s); 8.71 (1H, s); 9.18 (1H, s).

Compound No. 150 of Table 58: using benzylamine, $^1$H NMR (CH$_3$CN) δ ppm: 4.42 (2H, m); 5.81 (1H, s); 7.26 (6H, m); 7.50 (1H, d); 7.71 (1H, s); 7.98 (1H, d); 8.16 (1H, s); 8.68 (1H, s).

Compound No. 70 of Table 58: using allylamine, $^1$H NMR (CH$_3$CN) δ ppm: 3.86 (2H, m); 5.06 (1H, d); 5.14 (1H, d); 5.80 (1H, s); 5.86 (1H, m); 7.32 (1H, s); 7.36 (1H, s); 7.52 (1H, d); 7.99 (1H, d); 8.18 (1H, s); 8.68 (1H, s).

Compound No. 120 of Table 58: using thiazol-2-ylamine, $^1$H NMR (CH$_3$CN) δ ppm: 6.10 (1H, s); 7.14 (1H, d); 7.42 (1H, d); 7.48 (1H, d); 7.62 (1H, d); 8.04 (1H, d); 8.23 (1H, s); 8.72 (1H, s).

Compound No. 122 of Table 58: using furfurylamine, $^1$H NMR (CH$_3$CN) δ ppm: 4.40 (2H, m); 5.78 (1H, s); 6.21 (1H, s); 6.31 (1H, s); 7.30 (1H, s); 7.36 (1H, s); 7.50 (1H, d); 7.62 (1H, s); 7.98 (1H, d); 8.16 (1H, s); 8.68 (1H, s).

Compound No. 124 of Table 58: using thienylmethylamine, $^1$H NMR (CH$_3$CN) δ ppm: 4.58 (2H, m); 5.78 (1H, s); 6.90 (1H, s); 6.95 (1H, s); 7.12 (1H, d); 7.30 (1H, s); 7.50 (1H, d); 7.78 (1H, s); 7.96 (1H, s); 8.14 (1H, s); 8.66 (1H, s).

Compound No. 189 of Table 58: using 2-phenyl-prop-2-ylamine, $^1$H NMR (CH$_3$CN) δ ppm: 5.69 (1H, s); 7.29 (7H, m); 7.53 (1H, d); 8.00 (1H, d); 8.20 (1H, s); 8.70 (1H, s).

Compound No. 52 of Table 58: using 2-cyano-1-methoxy-prop-2-ylamine, $^1$H NMR (CH$_3$CN) δ ppm: 3.40 (3H, d); 3.62 (1H, m); 3.70 (1H, m); 5.82 (1H, s); 7.34 (1H, m); 7.36 (1H, d); 7.52 (1H, m); 8.00 (1H, d); 8.19 (1H, s); 8.69 (1H, s).

Compound No. 133 of Table 58: using 4-fluoroaniline, $^1$H NMR (CH$_3$CN) δ ppm: 5.91 (1H, s); 7.09 (2H, t); 7.40 (1H, s); 7.62 (3H, m); 8.02 (1H, d); 8.22 (1H, s); 8.70 (1H, s); 8.94 (1H, s).

Compound No. 38 of Table 58: using 2-cyano-3-methyl-but-2-ylamine, $^1$H NMR (CH$_3$CN) δ ppm: 1.00 (6H, 4×d); 1.57 (3H, 2×s); 2.36 (1H, m); 5.80 (1H, 2×s); 7.18 (1H, s); 7.32 (1H, m); 7.52 (1H, d); 8.00 (1H, d); 8.20 (1H, s); 8.70 (1H, s).

Compound No. 64 of Table 58: using trimethylsilylmethylamine, $^1$H NMR (CH$_3$CN) δ ppm: 2.76 (2H, m); 5.75 (1H, s); 6.98 (1H, s); 7.29 (1H, s); 7.50 (1H, d); 7.99 (1H, d); 8.17 (1H, s); 8.68 (1H, s).

Compound No. 84 of Table 58: using propargylamine, $^1$H NMR (CH$_3$CN) δ ppm: 2.43 (1H, s); 4.02 (2H, m); 5.80 (1H, s); 7.32 (1H, s); 7.52 (1H, d); 7.59 (1H, d); 7.99 (1H, d); 8.18 (1H, s); 8.68 (1H, s).

EXAMPLE 6

This Example illustrates the preparation of 2-(3,8-dibromoquinolinyl-6-oxy)-2-methylthio-N-(2-thienylmethyl)acetamide (Compound No. 124 of Table 61)

Stage 1: Preparation of
3,8-dibromo-6-hydroxyquinoline

Step 1: Preparation of
6-amino-3,8-dibromoquinoline 3,8-Dibromo-6-nitroquinoline (48.5 g, prepared as described in *J Am Chem Soc* (1955), 77, 4175-4176) was suspended in concentrated hydrochloric acid (400 ml) at ambient temperature and iron powder (27 g, reduced by hydrogen) was added in portions allowing the reaction temperature to rise to 73° C. during the additions. The bright yellow suspension that was initially produced became dark brown during the final stages of the reaction. The mixture was cooled to 0° C. and basified with aqueous sodium hydroxide (10M) until the reaction was at pH10. Ethyl acetate was added to the suspension and the mixture was thoroughly mixed then filtered through a bed of kieselguhr. The organic fraction was separated and the aqueous fraction re-extracted with further ethyl acetate. The insoluble material that was filtered from solution was further extracted with hot acetone and the organic fractions combined, washed with aqueous sodium hydrogen carbonate, dried over sodium sulphate and evaporated under reduced pressure to give 6-amino-3,8-dibromoquinoline as a brown solid, 34.7 g.

$^1$H NMR (CDCl$_3$) δ ppm: 4.09 (2H, s); 6.76 (1H, s); 7.52 (1H, s); 8.03 (1H, s); 8.71 (1H, s).

Step 2: Preparation of
3,8-dibromo-6-hydroxy-quinoline

6-Amino-3,8-dibromoquinoline (1.1 g) was suspended in phosphoric acid (10 ml) containing water (10 ml) and heated in a sealed glass tube at 180° C. for 4 days. The mixture was cooled to ambient temperature, poured into brine and extracted with ethyl acetate. The organic extract was dried over magnesium sulphate, evaporated under reduced pressure and the residual solid fractionated by chromatography (silica; hexane/ethyl acetate) to give 3,8-dibromo-6-hydroxy-quinoline, 0.4 g, as a pale brown solid.

$^1$H NMR (CDCl$_3$) δ ppm: 6.97 (1H, s); 7.69 (1H, s); 8.09 (1H, s); 8.72 (1H, s).

Stage 2

In a similar procedure to Stage 2, Step 1 of Example 5, 3,8-dibromo-6-hydroxyquinoline was reacted with ethyl 2-bromo-2-methylthioacetate to give ethyl 2-(3,8-dibromoquinolinyl-6-oxy)-2-methylthioacetate as a pale yellow gum.

$^1$H NMR (CDCl$_3$) δ ppm: 1.36 (3H, t); 2.24 (3H, s); 4.29-4.41 (2H, m); 5.69 (1H, s); 7.12 (1H, d); 7.88 (1H, d); 8.22 (1H, d); 8.89 (1H, d).

In a similar procedure to Stage 2, Step 2 of Example 5, ethyl 2-(3,8-dibromoquinolinyl-6-oxy)-2-methylthioacetate was hydrolysed to give 2-(3,8-dibromoquinolinyl-6-oxy)-2-methylthioacetic acid as a pale yellow solid.

$^1$H NMR (CDCl$_3$) δ ppm: 2.26 (3H, s); 5.71 (1H, s); 7.17 (1H, d); 7.89 (1H, d); 8.27 (1H, d); 8.88 (1H, d).

In a similar procedure to Stage 2 of Example 1, 2-(3,8-dibromoquinolinyl-6-oxy)-2-methylthioacetic acid was condensed with 2-aminomethylthiophene to give 2-(3,8-dibromoquinolinyl-6-oxy)-2-methylthio-N-(2-thienylmethyl) acetamide.

$^1$H NMR (CH$_3$CN) δ ppm: (some signals at high field obscured by NMR solvent) 4.41 (2H, m); 5.80 (1H, s); 7.23 (5H, m); 7.30 (1H, s); 7.68 (1H, s); 7.90 (1H, s); 8.36 (1H, s); 8.84 (1H, s).

The following amides were prepared using a similar procedure.

Compound No. 38 of Table 61: using 2-cyano-3-methyl-but-2-ylamine, $^1$H NMR (CH$_3$CN) δ ppm: 0.94-1.10 (6H, 4×d); 1.56-1.58 (3H, 2×s); 5.80 (1H, s); 7.15 (1H, s); 7.34 (1H, d); 7.94 (1H, d); 8.42 (1H, s); 8.85 (1H, s).

Compound No. 52 of Table 61: using 2-cyano-1-methoxy-prop-2-ylamine, $^1$H NMR (CH$_3$CN) δ ppm: 3.40 (3H, d); 3.65 (2H, m); 5.81 (1H, s); 7.34 (2H, m); 7.93 (1H, d); 8.39 (1H, s); 8.84 (1H, s).

Compound No. 12 of Table 61: using tert-butylamine, $^1$H NMR (CH$_3$CN) δ ppm: 5.63 (1H, s); 6.69 (1H, s); 7.30 (1H, s); 7.92 (1H, s); 8.39 (1H, s); 8.84 (1H, s).

Compound No. 150 of Table 61: using benzylamine, ¹H NMR (CH₃CN) δ ppm: 4.41 (2H, m); 5.80 (1H, s); 7.23 (5H, m); 7.30 (1H, s); 7.68 (1H, s); 7.90 (1H, s); 8.36 (1H, s); 8.84 (1H, s).

Compound No. 211 of Table 61: using N-morpholinohydrazine, ¹H NMR (CH₃CN) δ ppm: 3.59 (8H, m); 5.42 (1H, s); 6.09 (1H, s); 7.20 (1H, s); 7.86 (1H, s); 8.40 (1H, s); 8.83 (1H, s).

EXAMPLE 7

This Example illustrates the preparation of 2-(3-bromoquinolinyl-6-oxy)-2-methylthio-N-(1-methoxy-3-methylbut-3-yl)acetamide (Compound No. 48 of Table 57)

Stage 1: Preparation of 2-(3-bromoquinolinyl-6-oxy)-2-methylthioacetic acid

Step 1

In a similar procedure to Stage 2, Step 1 of Example 5, 3-bromo-6-hydroxy-quinoline (preparation described in *Liebigs Ann Chem* (1966), 98-106) was reacted with ethyl 2-bromo-2-methylthioacetate to give ethyl 2-(3-bromoquinolinyl-6-oxy)-2-methylthioacetate as a pale yellow gum.

¹H NMR (CDCl₃) δ ppm: 1.34 (3H, t); 2.24 (3H, s); 4.30-4.38 (2H, m); 5.70 (1H, s); 7.14 (1H, m); 7.48-7.52 (1H, dd); 8.02 (1H, d); 8.22 (1H, s); 8.80 (1H, s).

Step 2

In a similar procedure to Stage 2, Step 2 of Example 5, ethyl 2-(3-bromoquinolinyl-6-oxy)-2-methylthioacetate was hydrolysed to 2-(3-bromoquinolinyl-6-oxy)-2-methylthioacetic acid, colourless solid, m.p. 166-167° C.

¹H NMR (CDCl₃) δ ppm: 2.26 (3H, s); 5.76 (1H, s); 7.20 (1H, m); 7.50-7.54 (1H, dd); 8.01 (1H, d); 8.28 (1H, s); 8.78 (1H, s).

Stage 2: Preparation of 1-methoxy-3-methylbut-3-ylamine hydrochloride

To a stirred suspension of sodium hydride (0.30 g, 80% dispersion in mineral oil) in dry N,N-dimethylformamide (2 ml) under an atmosphere of nitrogen at ambient temperature was added dropwise a solution of 1-hydroxy-3-methylbut-3-ylamine (0.52 g) in N,N-dimethylformamide (5 ml). The mixture was stirred for 3 hours, methyl iodide (0.74 g) in N,N-dimethylformamide (5 ml) added over 5 minutes then stirred for another 2.25 hours and stored for 18 hours at ambient temperature. The solution was diluted with water, extracted into ethyl acetate (three times) and the extracts combined then extracted with dilute hydrochloric acid. The aqueous acidic extract was evaporated under reduced pressure and co-distilled with toluene to remove residual water to give 1-methoxy-3-methylbut-3-ylamine hydrochloride as a yellow gum.

¹H NMR (CDCl₃) δ ppm: 1.54 (6H, s); 1.96-2.00 (2H, t); 3.48 (3H, s); 3.62-3.66 (2H, t).

In a similar procedure, 1-hydroxy-3-methylbut-3-ylamine was reacted with ethyl iodide to give 1-ethoxy-3-methylbut-3-ylamine hydrochloride.

¹H NMR (CDCl₃) δ ppm: 1.20-1.24 (3H, t); 1.54 (6H, s); 1.96-2.00 (2H, t); 3.50 (2H, q); 3.66-3.70 (2H, t).

In a similar procedure, 1-hydroxy-2-methylprop-2-ylamine was reacted with methyl iodide to give 1-methoxy-2-methylprop-2-ylamine hydrochloride.

¹H NMR (CDCl₃) δ ppm: 1.47 (6H, s); 3.43 (3H, s); 3.44 (2H, s); 8.24 (3H bs).

In a similar procedure, 1-hydroxy-2-methylprop-2-ylamine was reacted with 4-fluorobenzyl bromide to give 1-(4-fluorobenzyloxy)-2-methylprop-2-ylamine hydrochloride.

¹H NMR (CDCl₃) δ ppm: 1.41 (6H, s); 3.46 (2H, s); 4.53 (2H, s); 7.00-7.04 (2H, m); 7.32-7.36 (2H, m); 8.30 (3H bs).

Stage 3

In a similar procedure to Stage 2 of Example 1, 2-(3-bromoquinolinyl-6-oxy)-2-methylthioacetic acid was condensed with 1-methoxy-3-methylbut-3-ylamine to give 2-(3-bromoquinolinyl-6-oxy)-2-methylthio-N-(1-methoxy-3-methylbut-3-yl)acetamide as a pale yellow solid, m.p. 88-90° C.

¹H NMR (CDCl₃) δ ppm: 1.46 (3H, s); 1.52 (3H, s); 1.80-1.84 (2H, q); 2.20 (3H, s); 3.30 (3H, s); 3.55-3.58 (2H, t); 5.55 (1H, s); 7.16 (1H, d); 7.43-7.46 (1H, dd); 7.90 (1H, s); 8.02-8.05 (1H, d); 8.24 (1H, s); 8.80 (1H, s).

The following amides were prepared using a similar procedure.

Compound No. 12 of Table 57: using t-butylamine, ¹H NMR (CDCl₃) δ ppm: 1.43 (9H, s); 2.20 (3H, s); 5.58 (1H, s); 6.43 (1H, s); 7.18 (1H, d); 7.44-7.48 (1H, dd); 8.03-8.05 (1H, d); 8.24 (1H, s); 8.82 (1H, s).

Compound No. 65 of Table 57: using 1-tert. butyldimethylsilyloxy-2-methylprop-2-ylamine, pale yellow oil, ¹H NMR (CDCl₃) δ ppm: 0.06 (3H, s); 0.08 (3H, s); 0.88 (9H, s); 1.38 (3H, s); 1.42 (3H, s); 2.18 (3H, s); 3.47-3.53 (2H, q); 5.59 (1H, s); 6.98 (1H, s); 7.16 (1H, d); 7.41-7.45 (1H, dd); 8.02-8.04 (1H, d); 8.24 (1H, s); 8.81 (1H, s).

Compound No. 50 of Table 57: using 1-methylthio-2-methylprop-2-ylamine, pale yellow oil, ¹H NMR (CDCl₃) δ ppm: 1.46 (3H, s); 1.48 (3H, s); 2.16 (3H, s); 2.22 (3H, s); 2.94-3.02 (2H, dd); 5.60 (1H, s); 6.72 (1H, s); 7.20 (1H, d); 7.46-7.48 (1H, dd); 8.04-8.06 (1H, d); 8.24 (1H, d); 8.81 (1H, d).

Compound No. 47 of Table 57: using 1-methoxy-2-methylprop-2-ylamine colourless solid, m.p. 90-91° C., ¹H NMR (CDCl₃) δ ppm: 1.40 (3H, s); 1.44 (3H, s); 2.20 (3H, s); 3.36-3.48 (2H, dd); 3.49 (3H, s); 5.59 (1H, s); 6.77 (1H, s); 7.18 (1H, d); 7.44-7.48 (1H, dd); 8.03-8.07 (1H, d); 8.26 (1H, d); 8.81 (1H, s).

Compound No. 49 of Table 57: using 1-ethoxy-3-methylbut-3-ylamine, colourless solid, m.p. 111-113° C., ¹H NMR (CDCl₃) δ ppm: 1.18-1.22 (3H, t); 1.46 (3H, s); 1.51 (3H, s); 1.78-1.84 (2H, m); 2.21 (3H, s); 3.44-3.50 (2H, q); 3.56-3.64 (2H, m); 5.53 (1H, s); 7.17 (1H, d); 7.44-7.46 (1H, dd); 7.82 (1H, s); 8.03-8.05 (1H, d); 8.25 (1H, s); 8.81 (1H, s).

Compound No. 40 of Table 57: using 1-hydroxy-3-methylbut-3-ylamine, colourless solid m.p. 124-126° C., ¹H NMR (CDCl₃) δ ppm: 1.48 (3H, s); 1.51 (3H, s); 1.84-1.92 (2H, m); 2.20 (3H, s); 3.86-3.89 (2H, t); 5.56 (1H, s); 7.14 (1H, d); 7.42-7.44 (1H, dd); 7.75 (1H, s); 8.00-8.03 (1H, d); 8.24 (1H, d); 8.80 (1H, d).

Compound No. 198 of Table 57: using 1-(4-fluorobenzyloxy)-2-methylprop-2-ylamine, colourless solid m.p. 124-126° C., ¹H NMR (CDCl₃) δ ppm: 1.42 (3H, s); 1.44 (3H, s); 2.16 (3H, s); 3.44-3.56 (2H, dd); 4.52 (2H, m); 5.58 (1H, s); 6.82 (1H, bs); 6.98-7.02 (2H, m); 7.13 (1H, d); 7.24-7.28 (2H, m); 7.34-7.38 (1H, dd); 8.00-8.02 (1H, d); 8.20 (1H, d); 8.80 (1H, d).

Compound No. 89 of Table 57: using 1-cyano-cyclopropylamine (O'Donnell et al, *Synthesis* (1984), 127), cream coloured solid, mp 178° C., ¹H NMR (CDCl₃) δ ppm: 2.13 (3H, s); 4.48-4.64 (2H, 4×d); 5.57 (1H, s); 6.86 (1H, s); 6.92 (1H, s); 7.08 (1H, t); 7.30-7.38 (5H, m).

Compound No. 4 of Table 57: using diethylamine, gum, ¹H NMR (CDCl₃) δ ppm: 1.15 (3H, t); 1.23 (3H, t); 2.29 (3H, s);

3.34 (1H, m); 3.50 (1H, m); 3.58 (2H, m); 5.83 (1H, s); 7.17 (1H, s); 7.51 (1H, d); 8.00 (1H, d); 8.22 (1H, s); 8.78 (1H, s).

Compound No. 2 of Table 57: using dimethylamine, cream coloured solid, m.p. 158-161° C.

Compound No. 27 of Table 57: using 3,3,3-trifluoro-2-methylprop-2-ylamine, pale yellow solid, mp 112° C.

Compound No. 88 of Table 57: using N,N-dicyclopropylamine, colourless solid, m.p. 122° C., $^1$H NMR (CDCl$_3$) δ ppm: 0.6-1.15 (8H, m); 2.21 (3H, s); 2.61 (1H, m); 2.80 (1H, m); 6.38 (1H, s); 7.17 (1H, d); 7.52 (1H, dd); 8.00 (1H, d); 8.20 (1H, d); 8.80 (1H, d).

Compound No. 60 of Table 57: using methyl 2-amino-2-methylpropionate, foamy solid, $^1$H NMR (CDCl$_3$) δ ppm: 1.69 (3H, s); 1.70 (3H, s); 2.26 (3H, s); 3.83 (3H, s); 5.70 (1H, s); 7.25 (1H, d); 7.35 (1H, s); 7.54 (1H, dd); 8.10 (1H, d); 8.30 (1H, d); 8.87 (1H, d).

Compound No. 64 of Table 57: using trimethylsilylmethylamine, $^1$H NMR (CH$_3$CN) δ ppm: 0.28 (9H, s); 3.04 (2H, s); 6.05 (1H, s); 7.28 (1H, s); 7.57 (1H, s); 7.79 (1H, d); 8.26 (1H, d); 8.64 (1H, s); 9.06 (1H, s).

Compound No. 124 of Table 57: using thienylmethylamine, $^1$H NMR (CH$_3$CN) δ ppm: 4.58 (2H, m); 5.78 (1H, s); 6.89 (1H, t); 6.96 (1H, d); 7.22 (1H, d); 7.27 (1H, s); 7.50 (1H, d); 7.78 (1H, s); 7.96 (1H, d); 8.32 (1H, s); 8.76 (1H, s).

Compound No. 35 of Table 57: using 2-cyano-prop-2-ylamine, $^1$H NMR (CH$_3$CN) δ ppm: 1.67 (3H, s); 1.69 (3H, s); 5.79 (1H, s); 7.31 (1H, s); 7.38 (1H, d); 7.55 (1H, d); 7.98 (1H, d); 8.37 (1H, s); 8.77 (1H, s).

Compound No. 133 of Table 57: using 4-fluoroaniline, $^1$H NMR (CDCl$_3$) δ ppm: 2.26 (3H, s); 5.82 (1H, s); 7.06 (2H, t); 7.26 (1H, m); 7.52 (1H, m); 7.60 (2H, m); 8.06 (1H, d); 8.26 (1H, d); 8.34 (1H, s); 8.82 (1H, s).

Compound No. 111 of Table 57: using 2-cyclohexenyl-ethylamine, $^1$H NMR (CH$_3$CN) δ ppm: 3.47 (4H, m); 5.58 (1H, s); 5.89 (1H, s); 7.25 (1H, m); 7.44 (1H, s); 7.66 (1H, d); 8.13 (1H, d); 8.51 (1H, s); 8.92 (1H, s).

Compound No. 150 of Table 57: using benzylamine, $^1$H NMR (CH$_3$CN) δ ppm: 4.42 (2H, m); 5.80 (2H, s); 7.25 (6H, m); 7.52 (1H, d); 7.71 (1H, s); 7.96 (1H, d); 8.32 (1H, s); 8.76 (1H, s).

Compound No. 38 of Table 57: using 2-cyano-3-methyl-but-2-ylamine, $^1$H NMR (CH$_3$CN) δ ppm: 1.00 (6H, 4×d); 1.57 (3H, 2×s); 2.38 (1H, m); 5.80 (1H, 2×s); 7.29 (1H, s); 7.31 (1H, m); 7.54 (1H, d); 7.99 (1H, d); 8.37 (1H, s); 8.77 (1H, s).

Compound No. 120 of Table 57: using thiazol-2-ylamine, $^1$H NMR (CH$_3$CN) δ ppm: 6.08 (1H, s); 7.12 (1H, s); 7.38 (1H, d); 7.46 (1H, s); 7.62 (1H, d); 8.00 (1H, d); 8.39 (1H, s); 8.78 (1H, s).

Compound No. 122 of Table 57: using furfurylamine, $^1$H NMR (CH$_3$CN) δ ppm: 4.42 (2H, m); 5.79 (1H, s); 6.22 (1H, s); 6.31 (1H, s); 7.28 (1H, s); 7.36 (1H, s); 7.50 (1H, d); 7.63 (1H, s); 7.95 (1H, d); 8.32 (1H, s); 8.75 (1H, s).

Compound No. 52 of Table 57: using 2-cyano-1-methoxy-prop-2-ylamine, $^1$H NMR (CDCl$_3$) δ ppm: 1.82 (3H, 2×s); 2.20 (3H, s); 3.52 (3H, 2×s); 3.66 (1H, m); 3.78 (1H, m); 5.72 (1H, 2×s); 7.15 (1H, 2×s); 7.20 (1H, m); 7.46 (1H, m); 8.06 (1H, d); 8.26 (1H, s); 8.82 (1H, d).

Compound No. 84 of Table 57: using propargylamine, $^1$H NMR (CH$_3$CN) δ ppm: 2.43 (1H, s); 4.00 (2H, m); 5.79 (1H, s); 7.30 (1H, s); 7.52 (1H, d); 7.60 (1H, s); 7.98 (1H, d); 8.36 (1H, s); 8.76 (1H, s).

Compound No. 189 of Table 57: using 2-phenyl-prop-2-ylamine, $^1$H NMR (CH$_3$CN) δ ppm: 1.60 (3H, s); 1.66 (3H, s); 5.69 (1H, s); 7.16 (1H, t); 7.27 (6H, m); 7.36 (1H, d); 7.54 (1H, d); 7.98 (1H, d); 8.36 (1H, s); 8.77 (1H, s).

Compound No. 70 of Table 57: using allylamine, $^1$H NMR (CH$_3$CN) δ ppm: 3.86 (2H, t); 5.06 (1H, d); 5.14 (1H, d); 5.79 (1H, s); 5.84 (1H, m); 7.32 (1H, s); 7.38 (1H, s); 7.52 (1H, d); 7.98 (1H, d); 8.35 (1H, s); 8.76 (1H, s).

EXAMPLE 8

This Example illustrates the preparation of 2-(3-fluoro-quinolinyl-6-oxy)-2-methylthio-N-(2-methylprop-2-yl)acetamide (Compound No. 12 of Table 59)

Stage 1: Preparation of 3-fluoro-6-hydroxyquinoline

Step 1: Preparation of 3-amino-6-methoxyquinoline

To a stirred mixture of 3-bromo-6-methoxyquinoline [synthesis given in Tetrahedron (1986), 42, 1475-1485] (2.38 g), tris(dibenzylideneacetone) dipalladium (0) (0.114 g) and tri t-butylphosphine tetrafluoroborate (0.116 g) in toluene (15 ml) under an atmosphere of nitrogen at ambient temperature was added a solution of lithium bistrimethylsilylamide (11.0 ml, 1.0M solution in hexanes). The mixture was stirred for 2 days and the brown suspension diluted with diethyl ether and extracted with 2M aqueous hydrochloric acid (twice) and the acidic fractions combined, washed with diethyl ether and made basic with 2M aqueous sodium hydroxide to give the required product as a brown solid that was used in the next Step without further purification.

$^1$H NMR (CDCl$_3$) δ ppm: 3.90 (3H, s); 6.87 (1H, d); 7.10 (1H, dd); 7.16 (1H, d); 7.85 (1H, d); 8.35 (1H, d).

Step 2: Preparation of 3-fluoro-6-methoxyquinoline

To boron trifluoride etherate (1.29 g) at −12° C. under an atmosphere of nitrogen was added with stirring a solution of 3-amino-6-methoxyquinoline (1.05 g) in dry dichloromethane (15 ml). The yellow suspension was stirred for 15 minutes then a solution of t-butylnitrite (0.74 g) in dichloromethane (5 ml) was added dropwise. The mixture was stirred for 2 hours at 0° C. then 1,2-dichlorobenzene was added and the mixture gradually heated to 73° C., allowing the dichloromethane to distil out from the reaction vessel and then increased to 90° C. to complete the reaction. The mixture was allowed to cool to ambient temperature, diluted with dichloromethane, washed with water, dried over magnesium sulfate, filtered then evaporated under reduced pressure to give a black oil that was fractionated by chromatography (silica; hexane/ethyl acetate) to give an oil, 0.54 g, containing the required product. MH$^+$178

Step 3

The product from Step 2 (0.45 g) and pyridine hydrochloride (4.5 g) were fused at 200° C. for 3 hour under an atmosphere of nitrogen. The mixture was cooled to ambient temperature, diluted with water and extracted with ethyl acetate. The extract was dried over magnesium sulfate, filtered and evaporated under reduced pressure to give the required product as a pale brown solid. MH$^+$ 164

Stage 2: Preparation of ethyl 3-fluoroquinolinyl-6-oxy-2-methylthioacetate

In a similar procedure to Stage 2, Step 1 of Example 5, 3-fluoro-6-hydroxy-quinoline was reacted with ethyl 2-bromo-2-methylthioacetate to give ethyl 2-(3-fluoro-quinolinyl-6-oxy)-2-methylthioacetate as a colourless solid.

$^1$H NMR (CDCl$_3$) δ ppm: 1.36 (3H, t); 2.25 (3H, s); 4.29-4.40 (2H, m); 5.71 (1H, s); 7.20 (1H, d); 7.47 (1H, dd); 7.71 (1H, dd); 8.11 (1H, d); 8.71 (1H, d).

In a similar procedure to Stage 2, Step 2 of Example 5, ethyl 2-(3-fluoro-quinolinyl-6-oxy)-2-methylthioacetate was hydrolysed to give 2-(3-fluoroquinolinyl-6-oxy)-2-methylthioacetic acid as a colourless solid.

$^1$H NMR (CDCl$_3$) δ ppm: 2.20 (3H, s); 4.0 (1H, bs); 5.69 (1H, s); 7.19 (1H, d); 7.39 (1H, dd); 7.68 (1H, dd); 7.96 (1H, d); 8.62 (d).

In a similar procedure to Stage 2 of Example 1, 2-(3-fluoroquinolinyl-6-oxy)-2-methylthioacetic acid was condensed with t-butylamine to give 2-(3-fluoroquinolinyl-6-oxy)-2-methylthio-N-(2-methylprop-2-yl)acetamide as a colourless gum.

$^1$H NMR (CDCl$_3$) δ ppm: 1.43 (9H, s); 2.20 (3H, s); 5.60 (1H, s); 6.45 (1H, s); 7.22 (1H, d); 7.41 (1H, dd); 7.71 (1H, dd); 8.08 (1H, d); 8.72 (1H, d).

Compound No. 52 of Table 59: In a similar procedure 2-(3-fluoroquinolinyl-6-oxy)-2-methylthioacetic acid was condensed with 2-cyano-1-methoxyprop-2-ylamine to give 2-(3-fluoroquinolinyl-6-oxy)-2-methylthio-N-(2-cyano-1-methoxyprop-2-yl)acetamide as a colourless gum.

$^1$H NMR (CDCl$_3$) δ ppm: 1.79 and 1.81 (3H, s); 2.22 (3H, s); 3.49 and 3.53 (3H, s); 3.67 (1H, d); 3.74 and 3.81 (1H, d); 5.71 and 5.74 (1H, s); 7.12 and 7.18 (1H, s); 7.26 (1H, d); 7.41 (1H, dd); 7.72 (1H, d); 8.10 (1H, d); 8.73 (1H, d) consistent with a 1:1 mixture of diasteroisomers.

EXAMPLE 9

This Example illustrates the preparation of 2-(methylthio)-2-(3-bromoquinolinyl-6-oxy)-N-E-(4-phenyl-2-methylpent-3-ene-2-yl)acetamide (Compound No. 82 of Table 57) and 2-(methylthio)-2-(3-phenylquinolinyl-6-oxy)-N-E-(4-phenyl-2-methylpent-3-ene-2-yl acetamide (Compound No. 82 of Table 65)

In a similar procedure to Stage 2 of Example 1, 2-(3-bromoquinolinyl-6-oxy)-2-methylthioacetic acid was condensed with 4-amino-4-methylpent-2-yne to give 2-(3-bromoquinolinyl-6-oxy)-2-methylthio-N-(2-methylpent-3-yn-2-yl)acetamide as a colourless solid, m.p. 135-137° C.

$^1$H NMR (CDCl$_3$) δ ppm: 1.70 (3H, s); 1.71 (3H, s); 1.83 (3H, s); 2.22 (3H, s); 5.62 (1H, s); 6.72 (1H, s); 7.18 (1H, d); 7.47 (1H, dd); 8.05 (1H, d); 8.24 (1H, d); 8.82 (1H, m).

A mixture of 2-(3-bromoquinolinyl-6-oxy)-2-methylthio-N-(2-methylpent-3-yn-2-yl)acetamide (0.200 g), tris-(dibenzylideneacetone) di-palladium (0) (0.007 g), phenylboronic acid (0.060 g), tri-tert.-butylphosphine tetrafluoroborate (0.006 g), cesium fluoride (0.245 g) in deoxygenated 1,4-dioxane (10 ml) were stirred at ambient temperature for 18 hours under an atmosphere of nitrogen. The mixture was filtered through kieselguhr then the filtrate was diluted with water, extracted with ethyl acetate and the organic phase separated, washed with brine, dried over magnesium sulfate and evaporated under reduced pressure to give a gum. The gum was fractionated by chromatography (silica; hexane:ethyl acetate 1:4 to 1:1 by volume) to give 2-(methylthio)-2-(3-bromoquinolinyl-6-oxy)-N-E-(4-phenyl-2-methylpent-3-ene-2-yl acetamide, 0.034 g as a colourless gum.

$^1$H NMR (CDCl$_3$) δ ppm: 1.67 (6H, s); 2.10 (3H, s); 2.24 (3H, s); 5.63 (1H, s); 5.91 (1H, s); 6.75 (1H, s); 7.25-7.35 (6H, m); 7.46 (1H, d); 8.06 (1H, d); 8.23 (1H, s); 8.81 (1H, s); And 2-(methylthio)-2-(3-phenylquinolinyl-6-oxy)-N-E-(4-phenyl-2-methylpent-3-ene-2-yl) acetamide, 0.012 g, as a colourless gum.

$^1$H NMR (CDCl$_3$) δ ppm: 1.67 (6H, s); 2.10 (3H, s); 2.26 (3H, s); 5.67 (1H, s); 5.92 (1H, s); 6.81 (1H, s); 7.25-7.35 (6H, m); 7.46 (2H, m); 7.53 (2H, m); 7.70 (2H, m); 8.10 (1H, d); 8.22 (1H, s); 9.10 (1H, s).

EXAMPLE 10

This Example illustrates the preparation of 2-(methylthio)-2-(3-[4-pyridyl]quinolinyl-6-oxy)-N-(2-methylprop-2-yl) acetamide (Compound No. 12 of Table 68)

A mixture of 2-(3-bromoquinolinyl-6-oxy)-2-methylthio-N-(2-methylprop-2-yl)acetamide (0.10 g), tris-(dibenzylideneacetone) di-palladium (0) (0.004 g), pyridine-4-boronic acid (0.032 g), tri-tert.-butylphosphine tetrafluoroborate (0.003 g), cesium fluoride (0.13 g) in deoxygenated 1,4-dioxane (10 ml) were stirred at ambient temperature for 18 hours under an atmosphere of nitrogen. To the mixture was added (tetrakis) triphenylphosphine palladium (0) (0.005 g) and sodium carbonate (0.100 g) and the reaction heated to 100° C. for 6 hours then stored at ambient temperature for 18 hours. The mixture was filtered through kieselguhr then the filtrate was diluted with water, extracted with ethyl acetate and the organic phase separated, washed with brine, dried over magnesium sulfate and evaporated under reduced pressure to give a gum. The gum was fractionated by chromatography (silica; hexane:ethyl acetate) to give the required product, 0.010 g, as a colourless solid m.p. 132-134° C.

$^1$H NMR (CDCl$_3$) δ ppm: 1.44 (9H, s); 2.22 (3H, s); 5.63 (1H, s); 6.46 (1H, s); 7.37 (1H, s); 7.54 (1H, d); 7.70 (2H, m); 8.17 (1H, d); 8.35 (1H, s); 8.79 (2H, m); 9.11 (1H, s).

Compound No. 12 of Table 65: In a similar procedure, 2-(3-bromoquinolinyl-6-oxy)-2-methylthio-N-(2-methylprop-2-yl)acetamide was reacted with phenyl boronic acid to give 2-(3-phenylquinolinyl-6-oxy)-2-methylthio-N-(2-methylprop-2-yl)acetamide as a cream coloured solid, m.p. 134-137° C.

$^1$H NMR (CDCl$_3$) δ ppm: 1.44 (9H, s); 2.22 (3H, s); 5.63 (1H, s); 6.49 (1H, s); 7.35-7.40 (2H, m); 7.46 (2H, m); 7.54 (2H, m); 7.72 (1H, d); 8.14 (1H, d); 8.26 (1H, s); 9.10 (1H, s).

EXAMPLE 11

This Example illustrates the preparation of 2-(3-bromoquinolinyl-6-oxy)-2-(methylthio)-N-(1-hydroxy-2-methylprop-2-yl) acetamide (Compound No. 39 of Table 57)

To a stirred solution of 2-(3-bromoquinolinyl-6-oxy)-2-(methylthio)-N-(1-(tert.butyldimethylsilyloxy)-2-methylprop-2-yl) acetamide (0.67 g) in tetrahydrofuran (10 ml) at 0-5° C. was added dropwise a solution of tetrabutylammonium fluoride (2.38 ml, 1M) in tetrahydrofuran. The mixture was stirred for 0.5 hours at 0° C. then allowed to warm to ambient temperature and stirred for a further 3 hours. The solvent was evaporated under reduced pressure and the residue treated with aqueous ammonium chloride solution, extracted into ethyl acetate and the organic phase washed with brine, dried over magnesium sulfate and evaporated under reduced pressure to give a solid. The solid was fractionated by chromatography (silica; ethyl acetate) to give the required product, 0.34 g, as a colourless solid, m.p. 155-157° C.

$^1$H NMR (CDCl$_3$) δ ppm: 1.36 (3H, s); 1.40 (3H, s); 2.20 (3H, s); 3.66-3.70 (2H, m); 3.89-3.92 (1H, t); 5.64 (1H, s); 6.70 (1H, s); 7.20 (1H, d); 7.44-7.48 (1H, dd); 8.02-8.06 (1H, d); 8.24 (1H, s); 8.82 (1H, s).

EXAMPLE 12

This Example illustrates the preparation of 2-(dibenzofuranyl-2-oxy)-2-methylthio-N-(2-methylprop-2-yl)acetamide (Compound No. 12 of Table 50)

Step 1: Preparation of ethyl 2-(dibenzofuranyl-2-oxy)-2-methylthioacetate

To a stirred suspension of sodium hydride (6.6 g, 80% dispersion in mineral oil) in dry N,N-dimethylformamide (25 ml) under an atmosphere of nitrogen at ambient temperature was added a solution of 2-hydroxydibenzofuran (36.8 g) in N,N-dimethylformamide (150 ml) over 40 minutes. The mixture was stirred for 3.25 hours then a solution of ethyl 2-bromo-2-methylthioacetate (54.2 g, 90% purity) in N,N-dimethylformamide (50 ml) was added dropwise over 20 minutes during which time the reaction temperature was allowed to rise to 47° C. On complete addition, the mixture was stirred for 21.5 hours, poured into water and extracted with diethyl ether (three times). The extracts were combined, washed with dilute aqueous sodium hydroxide (twice), water (three times) then dried over magnesium sulfate and evaporated under reduced pressure. The residue was fractionated by chromatography (silica; diethyl ether: hexane, 1:2 to 1:1 by volume) to give an orange oil, 33 g, containing the required product that was used in the next Stage without further purification. A sample of the oil was further purified by chromatography to provide an analytical sample.

$^1$H NMR (CDCl$_3$) δ ppm: 1.34-1.38 (3H, t); 2.26 (3H, s); 4.30-4.38 (2H, m); 5.64 (1H, s) 7.16-7.20 (1H, dd); 7.32-7.36 (1H, dd); 7.44-7.60 (4H, m); 7.92-7.94 (1H, d).

Step 2: Preparation of 2-(dibenzofuranyl-2-oxy)-2-methylthioacetic acid

To a stirred solution of ethyl 2-(dibenzofuranyl-2-oxy)-2-methylthioacetate (15.8 g) in tetrahydrofuran (250 ml) at ambient temperature was added a solution of sodium hydroxide (2.5 g) in water (25 ml). The mixture was stirred for 2 hours and evaporated under reduced pressure to remove the tetrahydrofuran. The residue was diluted with water, washed with diethyl ether (twice) and the aqueous phase acidified with concentrated hydrochloric acid then extracted with ethyl acetate (three times). The extracts were combined, washed with brine, dried over magnesium sulfate, filtered and evaporated under reduced pressure to give a yellow solid which was washed with a small volume of dichloromethane and filtered to provide 2-(dibenzofuranyl-2-oxy)-2-methylthioacetic acid, 5.90 g as a cream coloured solid.

$^1$H NMR (DMSO-d$_6$) δ ppm: 2.16 (3H, s); 6.02 (1H, s) 7.22-7.26 (1H, dd); 7.38-7.42 (1H, dd); 7.50-7.54 (1H, dd); 7.64-7.70 (2H, m); 7.90 (1H, m); 8.10-8.14 (1H, d).

Step 3

In a similar procedure to Stage 2 of Example 1, 2-(dibenzofuranyl-2-oxy)-2-methylthioacetic acid was condensed with t-butylamine to give the required product.

$^1$H NMR (CH$_3$CN) δ ppm: (some signals at high field obscured by NMR solvent) 5.56 (1H, s); 6.74 (1H, s); 7.20 (1H, d); 7.35 (1H, t); 7.48 (1H, t); 7.56 (2H, m); 7.70 (1H, s); 7.98 (1H, d).

The following amides were prepared using a similar procedure.

Compound No. 52 of Table 50: using 2-cyano-1-methoxyprop-2-ylamine, $^1$H NMR (CH$_3$CN) δ ppm: 3.40 (3H, 2×s); 3.64 (1H, m); 3.72 (1H, 2×s); 5.74 (1H, 2×s); 7.22 (1H, d); 7.36 (2H, m); 7.48 (1H, t); 7.56 (2H, m); 7.72 (1H, s); 8.00 (1H, d).

Compound No. 84 of Table 50: using propargylamine, $^1$H NMR (CH$_3$CN) δ ppm: 2.44 (1H, s); 4.03 (2H, m); 5.72 (1H, s); 7.22 (1H, dd); 7.36 (1H, t); 7.49 (1H, t); 7.56 (3H, m); 7.71 (1H, s); 8.00 (1H, d).

Compound No. 70 of Table 50: using allylamine, $^1$H NMR (CH$_3$CN) δ ppm: 3.88 (2H, t); 5.07 (1H, d); 5.16 (1H, d); 5.16 (1H, d); 5.72 (1H, s); 5.88 (1H, m); 7.22 (1H, dd); 7.36 (2H, t s); 7.49 (1H, t); 7.56 (3H, m); 7.71 (1H, s); 8.00 (1H, d).

Compound No. 189 of Table 50: using 2-phenyl-prop-2-ylamine, $^1$H NMR (CH$_3$CN) δ ppm: 5.62 (1H, s); 7.16 (1H, t); 7.25 (4H, m); 7.38 (3H, m); 7.50 (1H, t); 7.58 (2H, m); 7.71 (1H, s); 8.00 (1H, d).

Compound No. 120 of Table 50: using thiazol-2-ylamine, $^1$H NMR(CH$_3$CN) δ ppm: 6.00 (1H, s); 7.12 (1H, s); 7.31 (1H, d); 7.37 (1H, t); 7.48 (2H, m); 7.58 (2H, m); 7.80 (1H, s); 8.02 (1H, d).

Compound No. 122 of Table 50: using furfurylamine, $^1$H NMR (CH$_3$CN) δ ppm: 4.44 (2H, dq); 5.72 (1H, s); 6.24 (1H, s); 6.32 (1H, s); 7.20 (1H, d); 7.36 (2H, m); 7.54 (3H, m); 7.63 (1H, s); 7.70 (1H, s); 7.99 (1H, d).

Compound No. 133 of Table 50: using 4-fluoroaniline, $^1$H NMR (CH$_3$CN) δ ppm: 5.83 (1H, s); 7.09 (2H, t); 7.30 (1H, d); 7.36 (1H, t); 7.49 (1H, t); 7.58 (2H, m); 7.65 (2H, m); 7.80 (1H, s); 8.02 (1H, d); 8.96 (1H, s).

Compound No. 128 of Table 50: using 2-cyanoaniline, $^1$H NMR (CH$_3$CN) δ ppm: 5.94 (1H, s); 7.35 (4H, m); 7.50 (1H, t); 7.58 (1H, d); 7.68 (1H, t); 7.74 (1H, d); 7.83 (1H, s); 7.95 (1H, d); 8.02 (1H, s); 9.22 (1H, s).

Compound No. 38 of Table 50: using 2-cyano-3-methylbut-2-ylamine, $^1$H NMR (CH$_3$CN) δ ppm: 1.04 (6H, 4×d); 2.41 (1H, m); 5.72 (1H, s); 7.22 (2H, d); 7.36 (1H, t); 7.49 (1H, t); 7.56 (2H, m); 7.70 (1H, s); 8.01 (1H, d).

Compound No. 35 of Table 50: using 2-cyano-prop-2-ylamine, $^1$H NMR (CH$_3$CN) δ ppm: 5.72 (1H, s); 7.24 (1H, d); 7.37 (2H, m); 7.49 (1H, t); 7.56 (2H, m); 7.72 (1H, s); 8.00 (1H, d).

EXAMPLE 13

This Example illustrates the preparation of 2-(3-bromo-8-methylquinolinyl-6-oxy)-2-methylthio-N-(2-methylprop-2-yl)acetamide (Compound No. 12 of Table 72)

Stage 1: Preparation of 3-bromo-6-hydroxy-8-methylquinoline

6-Amino-3-bromo-8-methylquinoline (12 g) was suspended in a mixture of water (5 ml) and phosphoric acid (60 ml) and heated in a sealed glass tube to 180° C. for 3 days. The mixture was cooled to ambient temperature, diluted with water then taken to pH 3-4 with aqueous (2M) sodium hydroxide. The precipitate formed was filtered from solution, washed with cold water and sucked to dryness to give 3-bromo-6-hydroxy-8-methylquinoline, 11.0 g, as a grey solid.

$^1$H NMR (d6-DMSO) δ ppm: 2.56 (3H, s); 3.50 (1H, bs); 6.91 (1H, d); 7.15 (1H, d); 8.38 (1 h, d); 8.61 (1H, d).

Stage 2: Preparation of ethyl 2-(3-bromo-8-methylquinolinyl-6-oxy)-2-methylthioacetate In a similar procedure to Stage 2, Step 1 of Example 5, 3-bromo-8-methyl-6-hydroxyquinoline was reacted with ethyl 2-chloro-2-methylthioacetate to give ethyl 2-(3-bromo-8-methylquinolinyl-6-oxy)-2-methylthioacetate as a pale yellow oil.

$^1$H NMR (CDCl$_3$) δ ppm: 1.36 (3H, t); 2.23 (3H, s); 2.76 (3H, s); 4.27-4.40 (2H, m); 5.69 (1H, s); 6.97 (1H, d); 7.37 (1H, d); 8.18 (1H, d); 8.80 (1H, d).

In a similar procedure to Stage 2, Step 2 of Example 5, ethyl 2-(3-bromo-8-methylquinolinyl-6-oxy)-2-methylthioacetate was hydrolysed to give 2-(3-bromo-8-methylquinolinyl-6-oxy)-2-methylthioacetic acid as an off white solid.

$^1$H NMR (CDCl$_3$) δ ppm: 2.22 (3H, s); 2.71 (3H, s); 5.68 (1H, s); 6.97 (1H, d); 7.34 (1H, d); 8.17 (1H, d); 8.75 (1H, d).

In a similar procedure to Stage 2 of Example 1, 2-(3-bromo-8-methylquinolinyl-6-oxy)-2-methylthioacetic acid was condensed with tert. butylamine to give 2-(3-bromo-8-methylquinolinyl-6-oxy)-2-methylthio-N-(2-methylprop-2-yl)acetamide.

$^1$H NMR (CDCl$_3$) δ ppm: 1.43 (9H, s); 2.20 (3H, s); 2.78 (3H, s); 5.58 (1H, s); 6.42 (1H, s); 7.01 (1H, d); 7.32 (1H, d); 8.21 (1H, d); 8.82 (1H, d).

EXAMPLE 13A

This Example illustrates the preparation of 2-(3-iodo-quinolinyl-6-oxy)-2-methylthio-N-(2-methylprop-2-yl)acetamide (Compound No. 12 of Table 58A)

Step 1: Preparation of 3-iodo-6-hydroxyquinoline

To a stirred mixture of 3-bromo-6-hydroxyquinoline (preparation described in *Liebigs Ann Chem* (1966), 98-106) (1.0 g), sodium iodide (1.34 g) and copper iodide (0.09 g) in dioxane (6.5 ml) was added N,N,N',N'-tetramethyl-ethane-1,2-diamine (0.1 ml) in a sealed tube. The mixture was stirred at 120° C. for 12 h and upon cooling was treated with aqueous ammonia followed by aqueous hydrochloric acid. Extraction with ethyl acetate, drying of the organic phase over magnesium sulphate, filtration and evaporation under reduced pressure gave the required product (MH$^+$ 272) as a light brown coloured powder that was used as such in the next step.

Step 2: Preparation of N-tert-Butyl-2-(3-iodo-quinolin-6-yloxy)-2-methylsulfanyl-acetamide In a similar procedure to Stage 2, Step 1 of Example 5, 3-iodo-6-hydroxy-quinoline was reacted with chloro-methylsulfanyl-acetic acid ethyl ester to give (3-iodo-quinolin-6-yloxy)-methylsulfanyl-acetic acid ethyl ester as a yellow coloured solid.

In a similar procedure to Stage 2, Step 2 of Example 5, (3-iodo-quinolin-6-yloxy)-methylsulfanyl-acetic acid ethyl ester was hydrolysed to give (3-iodo-quinolin-6-yloxy)-methylsulfanyl-acetic acid as a yellow coloured solid (MH$^+$ 376).

In a similar procedure to Stage 2 of Example 1, (3-iodo-quinolin-6-yloxy)-methylsulfanyl-acetic acid was condensed with t-butylamine to give N-tert-butyl-2-(3-iodo-quinolin-6-yloxy)-2-methylsulfanyl-acetamide as a white solid (MH$^+$ 431).

$^1$H NMR (CDCl$_3$) δ ppm: 1.41 (9H, s); 2.20 (3H, s); 5.58 (1H, s); 6.42 (1H, s); 7.12 (1H, d); 7.45 (1H, dd); 8.02 (1H, d), 8.47 (1H, d); 8.92 (1H, d).

Compound No. 52 of Table 58A was prepared following a similar procedure using 2-cyano-1-methoxy-prop-2-ylamine.

EXAMPLE 13B

This Example illustrates the preparation of 2-(3-Bromo-8-fluoro-quinolin-6-yloxy)-N-tert-butyl-2-methylsulfanyl-acetamide (Compound No. 12 of Table 62B)

Stage 1: Preparation of 3-Bromo-8-fluoro-quinolin-6-ol

Step 1: Preparation of 3-Bromo-8-fluoro-6-methoxy-quinoline

A mixture of 3-bromo-6-methoxy-quinolin-8-ylamine (preparation described in Journal of Pharmaceutical Sciences (1984), 73(12), 1854-6) (5.0 g) in 20 ml fluoroboric acid, (50 wt % solution in water) at ~5° C. was treated with a solution of sodium nitrite (1.9 g in 3 ml of water) over a period of 40 minutes. The reaction mixture was stirred at room temperature for 2 hours after which time the precipitate was filtered and washed with cold diethyl ether. The resulting brown powder was added portionwise to hot dichlorobenzene over 1.5 hours. Stirring was then continued for an additional 30 min at 190° C. On cooling to room temperature, the mixture was treated with dilute hydrochloric acid and diluted with ethyl acetate. The organic phase was washed with dilute sodium hydroxide, dried over sodium sulphate, filtered and evaporated under reduced pressure to give a black oil that was fractionated by chromatography (silica; cyclohexane/ethyl acetate) to give the required product (M+256)

$^1$H NMR (CDCl$_3$) δ ppm: 3.88 (3H, s); 6.70 (1H, s); 7.04 (1H, dd); 8.10 (1H, s); 8.72 (1H, d).

Step 2

A mixture of the product from Step 1 (1.5 g) and hydrobromic acid (48 wt % solution in water) (6.8 ml) was refluxed for 62 hours. The mixture was cooled to ambient temperature, treated with sodium hydroxide (2M) and extracted with ethyl acetate. The extract was dried over sodium sulfate, filtered and evaporated under reduced pressure to give the required product, 3-bromo-8-fluoro-quinolin-6-ol, (M+242). $^1$H NMR (DMSO) δ ppm: 6.93 (1H, d); 7.05 (1H, dd); 8.52 (1H, dd); 8.66 (1H, d); 10.52 (1H, s).

Stage 2: Preparation of 2-(3-Bromo-8-fluoro-quinolin-6-yloxy)-N-tert-butyl-2-methylsulfanyl-acetamide In a similar procedure to Stage 2, Step 1 of Example 5, 3-bromo-8-fluoro-quinolin-6-ol was reacted with chloro-methylsulfanyl-acetic acid ethyl ester to give (3-Bromo-8-fluoro-quinolin-6-yloxy)-methylsulfanyl-acetic acid ethyl ester.

1H NMR (CDCl3) δ ppm: 1.35 (3H, t); 2.25 (3H, s); 4.30-4.40 (2H, m); 5.69 (1H, s); 6.96 (1H, d); 7.26 (1H, dd); 8.24 (1H, dd); 8.83 (1H, d).

In a similar procedure to Stage 2, Step 2 of Example 5, (3-Bromo-8-fluoro-quinolin-6-yloxy)-methylsulfanyl-acetic acid ethyl ester was hydrolysed to give 3-bromo-8-fluoro-quinolin-6-yloxy)-methylsulfanyl-acetic acid (M+348).

In a similar procedure to Stage 2 of Example 1, 3-bromo-8-fluoro-quinolin-6-yloxy)-methylsulfanyl-acetic acid was condensed with t-butylamine to give 2-(3-bromo-8-fluoro-quinolin-6-yloxy)-N-tert-butyl-2-methylsulfanyl-acetamide (M+403).

1H NMR (CDCl3) δ ppm: 1.42 (9H, s); 2.20 (3H, s); 5.58 (1H, s); 6.45 (1H, s); 6.99 (1H, d); 7.20 (1H, dd); 8.28 (1H, dd); 8.85 (1H, d).

Compound No. 52 of Table 62B was prepared following a similar procedure using 2-cyano-1-methoxy-prop-2-ylamine.

EXAMPLE 13C

This Example illustrates the preparation of N-tert-Butyl-2-(3-iodo-8-methyl-quinolin-6-yloxy)-2-methylsulfanyl-acetamide (Compound No. 12 of Table 72A)

Step 1: Preparation of 3-iodo-8-methyl-quinolin-6-ol

In a similar procedure to Step 1 of Example 13A, 3-bromo-8-methyl-quinolin-6-ol (preparation described in Example 13 Stage 1) was reacted sodium iodide, copper iodide and N,N,N',N'-tetramethyl-ethane-1,2-diamine to give the required product, 3-iodo-8-methyl-quinolin-6-ol, as a brown coloured solid ($MH^+$ 286).

$^1$H NMR (CDCl$_3$) δ ppm: 2.61 (3H, s); 6.92 (1H, d); 7.20 (1H, d); 8.60 (1H, dd); 8.79 (1H, d).

Step 2: Preparation of (3-Iodo-8-methyl-quinolin-6-yloxy)-methylsulfanyl-acetic acid ethyl ester In a similar procedure to Stage 2, Step 1 of Example 5, 3-iodo-8-methyl-quinolin-6-ol, was reacted with chloro-methylsulfanyl-acetic acid ethyl ester to give (3-iodo-8-methyl quinolin-6-yloxy)-methylsulfanyl-acetic acid ethyl ester as a yellow coloured solid ($MH^+$ 418).

In a similar procedure to Stage 2, Step 2 of Example 5, (3-iodo-8-methyl-quinolin-6-yloxy)-methylsulfanyl-acetic acid ethyl ester was hydrolysed to give (3-iodo-8-methyl-quinolin-6-yloxy)-methylsulfanyl-acetic acid as a yellow coloured solid ($[M-1]^+$ 388).

In a similar procedure to Stage 2 of Example 1, (3-iodo-8-methyl-quinolin-6-yloxy)-methylsulfanyl-acetic acid was condensed with t-butylamine to give N-tert-Butyl-2-(3-iodo-8-methyl-quinolin-6-yloxy)-2-methylsulfanyl-acetamide as a white solid ($[M+1]^+$ 445).

$^1$H NMR (CDCl$_3$) δ ppm: 1.41 (9H, s); 2.20 (3H, s); 2.54 (3H, s), 5.56 (1H, s); 6.42 (1H, s); 6.98 (1H, d); 7.32 (1H, dd); 8.42 (1H, d), 8.95 (1H, d).

Compound No. 52 of Table 72A was prepared following a similar procedure using 2-cyano-1-methoxy-prop-2-ylamine.

EXAMPLE 13D

This examples illustrates the preparation of 2-(3-bromo-8-chloro-quinolin-6-yloxy)-N-tert-butyl-2-methylsulfanyl-acetamide (Compound No. 12 of Table 62)

In a similar procedure to Step 2 of Example 6, 6-amino-3-bromo-8-chloroquinoline [preparation given in *J Am Chem Soc* (1955), 77, 4175-4176] was hydrolysed to give 3-bromo-8-chloro-6-hydroxyquinoline as a brown solid.

$^1$H NMR (CDCl$_3$) δ ppm: 7.00 (1H, d); 7.52 (1H, d); 8.17 (1H, d); 8.77 (1H, d); very broad signal at 7 ppm for OH.

In a similar procedure to Stage 2, Step 1 of Example 5, 3-bromo-8-chloro-6-hydroxyquinoline was reacted with ethyl 2-bromo-2-methylthioacetate to give ethyl 2-(3-bromo-8-chloroquinolinyl-6-oxy)-2-methylthioacetate as a yellow gum.

$^1$H NMR (CDCl$_3$) δ ppm: 1.37 (3H, t); 2.23 (3H, s); 4.28-4.40 (2H, m); 5.69 (1H, s); 7.08 (1H, d); 7.68 (1H, d); 8.25 (1H, d); 8.90 (1H, d).

In a similar procedure to Stage 2, Step 2 of Example 5, ethyl 2-(3-bromo-8-chloroquinolinyl-6-oxy)-2-methylthioacetate was hydrolysed to 2-(3-bromo-8-chloroquinolinyl-6-oxy)-2-methylthioacetic acid as a colourless solid.

$^1$H NMR (d6-DMSO) δ ppm: 2.17 (3H, s); 6.16 (1H, s); 7.52 (1H, d); 7.86 (1H, d); 8.68 (1H, d); 8.93 (1H, d).

In a similar procedure to Stage 2 of Example 1, 2-(3-bromo-8-chloroquinolinyl-6-oxy)-2-methylthioacetic acid was condensed with tert-butyl amine to give 2-(3-bromo-8-chloro-quinolin-6-yloxy)-N-tert-butyl-2-methylsulfanyl-acetamide (Compound No. 12 of Table 62) as a white solid, m.p. 160-161° C.

$^1$H NMR (CDCl$_3$) δ ppm: 1.43 (9H, s); 2.20 (3H, s); 5.57 (1H, s); 6.39 (1H, bs); 7.11 (1H, d); 7.62 (1H, d); 8.29 (1H, d); 8.92 (1H, d).

EXAMPLE 13E

This examples illustrates the preparation of 2-(3-bromo-8-iodo-quinolin-6-yloxy)-N-tert-butyl-2-methylsulfanyl-acetamide (Compound No. 12 of Table 62A).

Stage 1. Preparation of 3-bromo-8-iodo-quinolin-6-ol
Step 1

2-Iodo-4-nitroaniline (5.3 g) in acetic acid (40 ml) was treated with 2,2,3 tribromopropanal (5.9 g) and the mixture was heated at 110° C. for 2 h after which it was cooled to room temperature and filtered. The filtered solid was washed with diethyl ether, suspended in water and treated with saturated sodium hydrogen carbonate. Extraction with ethyl acetate, drying over sodium sulphate, filtration and evaporation under reduced pressure gave the desired product, 3-bromo-8-iodo-6-nitro-quinoline, as a yellow solid after chromatography (silica; hexane/ethyl acetate) (M+379).

$^1$H NMR (CDCl$_3$) δ ppm: 8.50 (1H, d); 8.72 (1H, d); 9.08 (1H, d); 8.62 (1H, d).
Step 2

In a similar procedure to Stage 1, Step 1 of Example 6, 3-bromo-8-iodo-6-nitro-quinoline was treated with concentrated hydrochloric acid and iron powder to give 3-bromo-8-iodo-quinolin-6-ylamine as a beige powder ($(M+1)^+$ 351).

$^1$H NMR (CDCl$_3$) δ ppm: $^1$H NMR (CDCl$_3$) δ ppm: 4.04 (1H, bs); 6.77 (1H, bs); 7.79 (1H, bs); 7.98 (1H, bs); 8.67 (1H, bs).
Step 3

In a procedure described into Step 2 of Example 6, 3-bromo-8-iodo-quinolin-6-ylamine from Step 2 was hydrolysed to give 3-bromo-8-iodo-quinolin-6-ol as a yellow solid ($(M+2)^+$ 352).

$^1$H NMR (DMSO-d$_6$) δ ppm: 7.20 (1H, d); 7.98 (1H, d); 8.52 (1H, d); 8.73 (1H, d); 40.50 (1H, s).
Stage 2
Step 1

In a similar procedure to Stage 2, Step 1 of Example 5, 3-bromo-8-iodo-quinolin-6-ol (from Stage 1, Step 3, Example 13E) was reacted with chloro-methylsulfanyl-acetic acid methyl ester to give (3-bromo-8-iodo-quinolin-6-yloxy)-methyl-sulfanyl-acetic acid methyl ester as a yellow solid ($(M+2)^+$ 470).

$^1$H NMR (CDCl$_3$) δ ppm: 2.22 (3H, s); 3.89 (3H, s); 5.70 (1H, s); 7.15 (1H, d); 8.15 (1H, d); 8.20 (1H, d); 8.86 (1H, d).

In a similar procedure to Stage 2, Step 2 of Example 5, (3-bromo-8-iodo-quinolin-6-yloxy)-methyl-sulfanyl-acetic acid methyl ester was hydrolysed to (3-bromo-8-iodo-quinolin-6-yloxy)-methyl-sulfanyl-acetic acid as a yellow solid ($(M+2)^+$ 456).

$^1$H NMR (d6-DMSO) δ ppm: 2.17 (3H, s); 6.13 (1H, s); 7.59 (1H, d); 8.20 (1H, d); 8.59 (1H, d); 8.89 (1H, d).

In a similar procedure to Stage 2 of Example 1, (3-bromo-8-iodo-quinolin-6-yloxy)-methyl-sulfanyl-acetic acid was condensed with tert-butyl amine to give 2-(3-Bromo-8-iodo-quinolin-6-yloxy)-N-tert-butyl-2-methylsulfanyl-acetamide (Compound No. 12 of Table 62A) as a white solid, m.p. 171-172° C.

$^1$H NMR (CDCl$_3$) δ ppm: 1.43 (9H, s); 2.19 (3H, s); 5.57 (1H, s); 6.39 (1H, bs); 7.19 (1H, d); 8.10 (1H, d); 8.20 (1H, d); 8.89 (1H, d).

EXAMPLE 14

This Example illustrates the fungicidal properties of compounds of formula (1).

The compounds were tested in a leaf disk assay, with methods described below. The test compounds were dissolved in DMSO and diluted into water to 200 ppm. In the case of the test on *Pythium ultimum*, they were dissolved in DMSO and diluted into water to 20 ppm.

*Erysiphe graminis* f.sp. *hordei* (barley powdery mildew): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Erysiphe graminis* f.sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f.sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia oryzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Septoria tritici* (leaf blotch): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 72 hrs.

*Fusarium culmorum* (root rot): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 48 hrs.

*Pythium ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added. The test plate was incubated at 24° C. and the inhibition of growth was determined photometrically after 48 hours.

The following compounds (number of compound first, followed by table number in brackets) gave at least 60% control of the following fungal infection at 200 ppm:

*Plasmopara viticola*, compounds 8 (57), 12 (1), 12 (13), 12 (15), 12(36), 12 (44), 12(47), 12 (55), 12 (57), 12 (58), 12 (58A), 12 (59), 12 (60), 12 (62), 12 (62B), 12 (72), 12 (72A), 12 (81), 13 (57), 16 (57), 42 (57), 43 (57), 47 (57), 47 (72), 48 (57), 52 (13), 52 (57), 52 (58), 52 (58A), 52 (59), 52 (60), 52 (61), 52 (72), 52 (81), 53 (1), 53 (62B), 60 (57), 62 (31), 63 (57), 68 (57), 68 (61), 68 (62), 68 (72), 82 (57), 133 (81), 144 (57), 152 (57), 153 (57), 155 (57), 164 (57), 171 (57), 180 (57), 183 (57), 187 (57), 189 (81), 210 (57), 220 (57), 220 (61), 220 (62), 224 (57), 224 (61), 227 (1), 226 (57), 227 (57), 230 (57), 231 (50), 235 (57);

*Phytophthora infestans*, compounds 12 (1), 12 (13), 12 (15), 12 (44), 12 (57), 12 (58), 12 (58A), 12 (59), 12 (60), 12 (62), 12 (62B), 12 (70), 12 (72), 12 (72A), 13 (57), 16 (57), 39 (57), 40 (57), 42 (57), 43 (57), 47 (57), 47 (62), 47 (72), 48 (57), 49 (57), 50 (57), 50 (62), 50 (72), 52 (13), 52 (57), 52 (58), 52 (58A), 52 (59), 52 (60), 52(72), 52 (72A), 52 (81), 53 (62B), 60 (57), 62 (57), 63 (57), 68 (57), 68 (61), 68 (72), 70 (58), 82 (57), 82 (65), 84 (58), 89 (57), 102 (57), 198 (57), 220 (57), 220 (61), 220 (62), 220 (72), 224 (57), 224 (62), 231 (57), 236 (57);

*Erysiphe graminis* f.sp. *tritici*, compounds 4 (57), 7 (57), 8 (57), 11 (57), 12 (1), 12 (13), 12 (44), 12 (50), 12 (57), 12 (58), 12 (58A), 12 (61), 12 (62), 12 (62B), 12 (72A), 13 (57), 16 (61), 16 (62), 27 (57), 35 (50), 35 (57), 35 (58), 39 (57), 42 (57), 43 (57), 45 (57), 46 (57), 47 (57), 47 (62), 47 (72), 48 (57), 49 (57), 50 (57), 50 (61), 50 (62), 50 (70), 50 (72), 52 (13), 52 (50), 52 (57), 52 (58), 52 (58A), 52 (61), 52 (70), 52 (72), 52 (72A), 53 (57), 53 (62B), 62 (57), 63 (57), 68 (61), 68 (62), 68 (72), 70 (57), 70 (58), 71 (57), 76 (57), 84 (57), 84 (58), 89 (57), 124 (57), 124 (58), 144 (57), 150 (61), 152 (57), 157 (57), 158 (57), 159 (57), 160 (57), 164 (57), 165 (57), 172 (57), 173 (57), 176 (57), 178 (57), 180 (57), 198 (57), 200 (57), 202 (57), 209 (57), 220 (62), 220 (82), 224 (61), 224 (83), 231 (57), 236 (57), 237 (57),

*Pyricularia oryzae*, compounds 12 (50), 12 (57), 12 (58), 35 (57), 35 (58), 38 (58), 46 (57), 47 (57), 52 (57), 84 (57), 120 (57), 166 (57), 189 (57), 200 (57);

*Botrytis cinerea*, compounds 8 (57), 16 (61), 38 (61), 12 (67), 47 (62), 12 (83a), 48 (57), 50 (57), 50 (62), 52 (50), 52 (57), 52 (67), 68 (62), 68 (61), 68 (72), 120 (58), 122 (50), 124 (58), 133 (57), 164 (57), 169 (57), 207 (57), 211 (61), 220 (61),

*Erysiphe graminis* f.sp. *hordei*, compounds 4 (57), 6 (57), 8 (57), 12 (1), 12 (13), 12 (15), 12 (50), 12 (57), 12 (58), 12 (61), 13 (57), 27 (57), 33 (57), 35 (50), 35 (57), 35 (58), 38 (50), 38 (58), 38 (61), 39 (57), 40 (57), 42 (57), 43 (57), 45 (57), 47 (57), 48 (57), 49 (57), 50 (57), 52 (13), 52 (50), 52 (57), 52 (58), 52 (61), 52 (67), 53 (57), 59 (57), 60 (57), 62 (57), 63 (57), 65 (57), 70 (13), 70 (50), 70 (57), 70 (58), 71 (57), 84 (50), 84 (57), 84 (58), 85 (57), 89 (57), 102 (57), 120 (58), 122 (57), 122 (58), 124 (58), 124 (61), 128 (58), 133 (81), 144 (57), 150 (58), 150 (61), 152 (57), 153 (57), 157 (57), 158 (57), 161 (57), 163 (57), 164 (57), 177 (57), 178 (57), 180 (57), 183 (57), 185 (57), 189 (57), 189 (58), 192 (57), 198 (57), 200 (57), 211 (61), 212 (57), 216 (57);

*Puccinia recondita* f.sp. *tritici*, compounds 12 (58A), 12 (72A), 35 (50), 47 (57), 47 (72), 52 (58A), 220 (72);

*Septoria nodorum*, compounds 12 (50), 12 (61), 47 (57), 52 (50), 84 (50), 84 (57), 120 (57), 133 (57), 198 (57);

*Septoria tritici*, compounds 12 (1), 12 (36), 12 (44), 12 (47), 12 (55), 12 (57), 12 (62), 12 (83A), 12 (83B), 16 (57), 16 (61), 16 (72), 47 (62), 12 (58A), 12 (60), 47 (62), 12 (62A), 12 (62B), 12 (72a), 47 (72), 50 (61), 50 (62), 50 (72), 52 (52), 52 (58A), 52 (61), 52 (62B), 52 (72), 52 (72A), 68 (57), 68 (61), 68 (72), 220 (57), 220 (61), 220 (62), 220 (72), 224 (57), 224 (61), 224 (62), 230 (50), 226 (57), 228 (57), 230 (57), 235 (57), 236 (57), 237 (57).

*Fusarium culmorum*, compounds 12 (58A), 12 (62), 12 (62A), 12 (62B), 12 (72A), 16 (57), 16 (61), 16 (62), 47 (62), 47 (72), 50 (62), 50 (72), 52 (58A), 52 (72A), 68 (62), 68 (57), 68 (61), 68 (72), 220 (57), 220 (61), 220 (62), 220 (72), 235 (57).

The following compounds (number of compound first, followed by table number in brackets) gave at least 60% control of the following fungal infection at 20 ppm:

*Pythium ultitnum*, compounds 2 (57), 12 (1), 12 (13), 12 (15), 12 (47), 12 (55), 12 (57), 12 (58), 12 (58A), 12 (59), 12 (60), 12 (62), 12 (62B), 12 (65), 12 (70), 12 (81), 12 (83b), 12 (36), 12 (44), 13 (57), 16 (72), 27 (57), 35 (57), 35 (58), 35 (81), 39 (57), 40 (57), 42 (57), 43 (57), 47 (57), 47 (62), 47 (72), 48 (57), 49 (57), 50 (57), 50 (62), 50 (72), 52 (57), 52 (58), 52 (58A), 52 (59), 52 (62B), 52 (72), 52 (72A), 52 (81), 59 (57), 60 (57), 62 (57), 63 (57), 65 (57), 68 (57), 68 (61), 68 (72), 70 (57), 70 (58), 70 (81), 82 (57), 84 (57), 84 (58), 89 (57), 120 (57), 122 (57), 122 (58), 124 (57), 133 (57), 133 (58), 133 (81), 185 (57), 189 (44), 189 (57), 189 (81), 220 (57), 220 (62), 224 (57), 231 (57), 235 (57), 236 (57).

The invention claimed is:

1. A compound of the general formula (1):

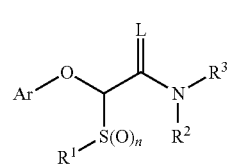

wherein Ar is quinolinyl optionally substituted with one, two or three substituents independently selected from halo, $C_{1-4}$ alkyl, halo($C_{1-4}$)alkyl, aryl and heteroaryl;

$R^1$ is methyl;

$R^2$ is H or methyl;

$R^3$ is tert-butyl, 1,1,1-trifluoro-2-methylprop-2-yl, 2-cyanoprop-2-yl, 1-methoxy-2-methylprop-2-yl, 1-methylthio-2-methylprop-2-yl, 1-methoxy-3-methylbut-3-yl, 2-cyano-1-methoxy-prop-2-yl, 2-methoxycarbonylprop-2-yl or 2-methylaminocarbonylprop-2-yl, 2-hydroxymethyl-1-methoxy-prop-2-yl or 1-methoxy-2-methoxymethyl-prop-2-yl, L is O or S; and n is 0, 1 or 2.

2. The compound according to claim 1 wherein Ar is 3-bromoquinolin-6-yl, 3-chloroquinolin-6-yl, 3-fluoroquinolin-6-yl, 3,8-dibromoquinolin-6-yl, 3-bromo-8-chloroquinolin-6-yl, 3-bromo-8-methylquinolin-6-yl, 3-phenylquinolin-6-yl or 3-pyrid-4-ylquinolin-6-yl.

3. The compound according to claim 1 wherein Ar is 3-bromoquinolin-6-yl, 3,8-dibromoquinolin-6-yl, 3-bromo-8-chloroquinolin-6-yl or 3-bromo-8-methylquinolin-6-yl.

4. The compound according to claim 1 wherein Ar is 3,8-difluoroquinolin-6-yl, 3-fluoro-8chloroquinolin-6yl, 3-fluoro-8-bromoquinolin-6-yl, 3-fluoro-8-iodoquinolin-6-yl, 3-fluoro-8-methylquinolin-6-yl, 3,8-dichloroquinolin-6-yl, 3-chloro-8-fluoroquinolin-6yl, 3-chloro-8-bromoquinolin-6-yl, 3-chloro-8-iodoquinolin-6-yl, 3-chloro-8-methylquinolin-6-yl, 3,8-bromoquinolin-6-yl, 3-bromo-8-chloroquinolin-6yl, 3-bromo-8-fluoroquinolin-6-yl, 3-bromo-8-iodoquinolin-6-yl, 3-bromo-8-methylquinolin-6-yl, 3,8-iodoquinolin-6-yl, 3-iodo-8-chloroquinolin-6yl, 3-iodo-8-bromoquinolin-6-yl, 3-iodo-8-fluoroquinolin-6-yl or 3-iodo-8-methylquinolin-6-yl.

5. The compound according to claim 1 wherein Ar is 8-haloquinolin-6-yl or 8-methylquinolin-6-yl.

6. The compound according to claim 1 wherein R3 is 2-hydroxymethyl-1-methoxy-prop-2-yl or 1-methoxy-2-methoxymethyl-prop-2-yl.

7. The compound according to claim 1 wherein L is O.

8. The compound according to claim 1 wherein n is 0.

9. A process for preparing a compound according to claim 1 wherein n is 0, which comprises (a) reacting the compound of the formula (4)

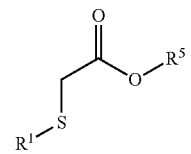

with a halogenating agent, (b) reacting the resulting compound of the formula (5)

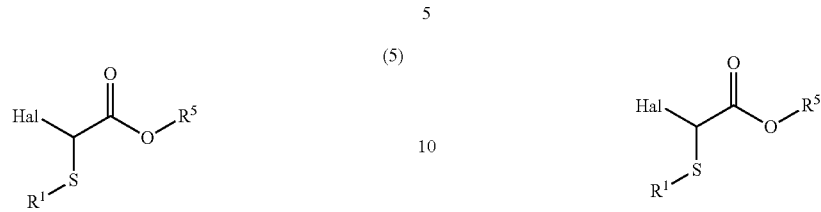
(5)

in the presence of a base with a compound Ar—OH, where R is as defined in claim 1, to yield the compound of the formula (6)

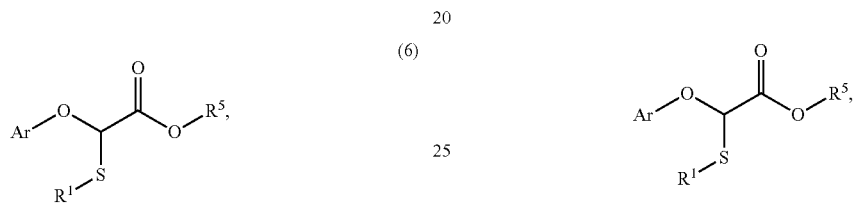
(6)

(c) converting this compound in the presence of a base to the corresponding acid of the formula (7)

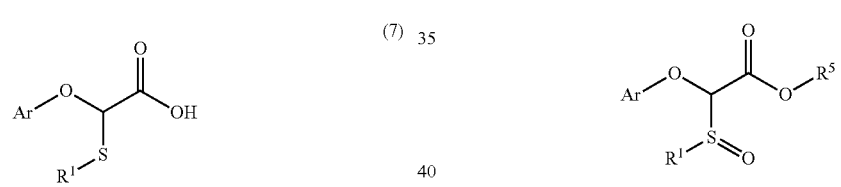
(7)

and (d) reacting this acid with an amine of the formula (8)

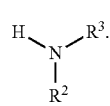
(8)

10. A process for preparing a compound according to claim 1 wherein n is 1 or 2, which comprises (a) reacting the compound of the formula (4)

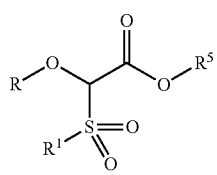
(4)

with a halogenating agent, (b) reacting the resulting compound of the formula (5)

(5)

in the presence of a base with a compound Ar—OH, where R is as defined in claim 1, to yield the compound of the formula (6)

(6)

(c) treating this compound with an oxidising agent to obtain the compounds of the formula (9)

(9)

or (10)

(10)

(d) converting this compound in the presence of a base to the corresponding acid of the formula (11)

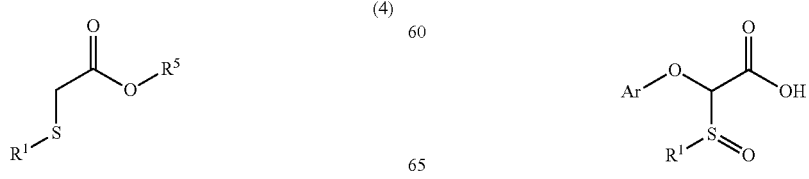
(11)

or (12)

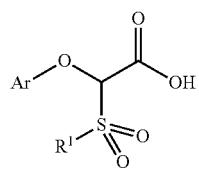
(12)

and (d) reacting the compound of the formula (11) or (12) with an amine of the formula (8)

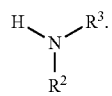
(8)

11. A process for preparing a compound according to claim 1 wherein n is 0, which comprises (a) reacting the compound of the formula (2)

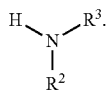
(2)

with a halogenating agent, (b) converting the compound thus obtained of the formula (3)

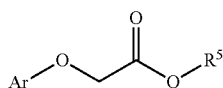
(3)

with an alkanethiol of the formula R1-SH, where R1 is as defined in claim 1, to the compound of the formula (6)

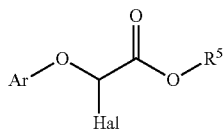
(6)

(c) converting this compound in the presence of a base to the corresponding acid of the formula (7)

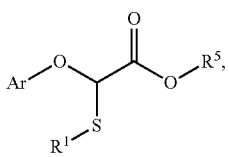
(7)

and (d) reacting this acid with an amine of the formula (8)

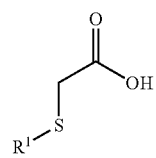
(8)

12. A process for preparing a compound according to claim 1 wherein n is 0, which comprises (a) reacting the compound of the formula (13)

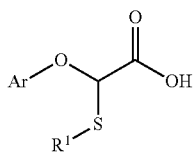
(13)

with an amine of the formula (8)

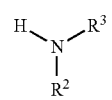
(8)

to form the compound of the formula (14)

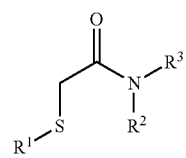
(14)

(b) treating this compound with a halogenating agent to yield the compound of the formula (16)

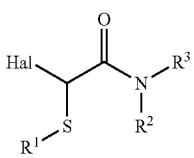
(16)

and (c) reacting this compound in the presence of a base with Ar—OH, where Ar is as defined in claim 1.

13. A process for preparing a compound according to claim 1 wherein n is 0, which comprises (a) reacting the compound of the formula (15)

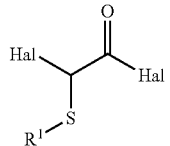
(15)

in the presence of a base with an amine of the formula (8)

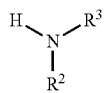
(8)

to form the compound of the formula (16)

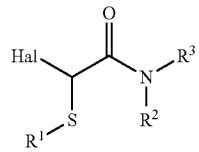
(16)

and (b) reacting this compound in the presence of a base with Ar—OH, where Ar is as defined in claim 1.

14. A fungicidal composition comprising a fungicidally effective amount of a compound of formula (1) according to claim 1 and a suitable carrier or diluent therefor.

15. A method of combating or controlling phytopathogenic fungi which comprises applying a fungicidally effective amount of a compound of formula (1) according to claim 14 to a plant, to a seed of a plant, to the locus of the plant or seed or to soil or any other plant growth medium.

* * * * *